(12) United States Patent
Grönberg et al.

(10) Patent No.: US 6,893,833 B2
(45) Date of Patent: May 17, 2005

(54) IDENTIFICATION OF AGENTS THAT INCREASE GLUCOSE UPTAKE

(75) Inventors: Alvar Grönberg, Knivsta (SE); Per Wikström, Upplands Väsby (SE)

(73) Assignee: Glucox AB, Stockholm (SE)

( * ) Notice: Subject to any disclaimer, the term of this patent is extended or adjusted under 35 U.S.C. 154(b) by 0 days.

(21) Appl. No.: 10/418,036

(22) Filed: Apr. 17, 2003

(65) Prior Publication Data

US 2003/0225117 A1 Dec. 4, 2003

Related U.S. Application Data

(60) Provisional application No. 60/410,626, filed on Sep. 13, 2002.

(30) Foreign Application Priority Data

Apr. 17, 2002 (SE) .............................................. 0201152

(51) Int. Cl.$^7$ ................................................ C12Q 1/54
(52) U.S. Cl. .......................................... 435/14; 435/25
(58) Field of Search ..................... 435/14, 25; 514/866; 600/347

(56) References Cited

U.S. PATENT DOCUMENTS

| | | | | |
|---|---|---|---|---|
| 4,954,445 A | * | 9/1990 | Yoshihama et al. | 435/191 |
| 5,250,416 A | * | 10/1993 | Ohno et al. | 435/15 |
| 5,763,496 A | * | 6/1998 | Holland | 514/689 |
| 5,902,831 A | * | 5/1999 | Holland et al. | 514/685 |
| 6,090,851 A | * | 7/2000 | Dodd-o et al. | 514/568 |
| 6,218,117 B1 | * | 4/2001 | Herrnstadt et al. | 435/6 |
| 2001/0019832 A1 | | 9/2001 | Luthman | |

FOREIGN PATENT DOCUMENTS

| | | |
|---|---|---|
| EP | 0 551 662 A1 | 7/1993 |
| WO | WO 99/12539 | 3/1999 |
| WO | WO 01/017533 | 3/2001 |

OTHER PUBLICATIONS

Gatley S. J. Some Aspects of the Pharmacology of Diphenyleneiodonium, A Bivalent Iodine Compound. Xenobiotica 9(9)539–546, 1979.*
Holland P. Mechanism of Action of the Hypoglycemic Agent Diphenyleneiodonium. J of Biological Chemistry 248(17)6050–6, 1973.*
Rudkowski R. Auranofin Inhibits the Activation Pathways of PMN Leukocytes at Multiple Sites. Biochemical Pharmacology 41(12)1921–1929, 1991.*
Mukherjee S. Reduced NADPH Oxidase in Adipocyte Plasma Membrane and Its Activation by Insulin. Arch of Biochem Biophys 184(1)69–76, 1977.*
Abo et al., "Reconstitution of Neutrophil NADPH Oxidase Activity in the Cell–free System by Four Components: p67–phox, p47–phox, p21racl, and Cytochrome b$_{-245}$" *Journal of Biological Chemistry,* 267: 16767–70 (1992).

Babior, "The Respiratory Burst Oxidase" *Advances in Enzymology & Related Areas of Molecular Biology* 65: 49–95 (1992).
Bayraktutan et al., "Expression of a Functional Neutrophil–type NADPH Oxidase in Cultured rat Coronary Microvascular Endothelial cells" *Cardiovascular Research,* 38: 256–62 (1998).
Blair et al., "Regulation of Glucose Transport and Glycogen Synthesis in L6 Muscle Cells During Oxidative Stress" *Journal of Biological Chemistry* 274: 36293–9 (1999).
Davis et al., "Similarities in the Metabolism of Alloxan and Dehydroascorbate in Human Erythrocytes" *Biochemical Pharmacology* 55: 1301–7 (1998).
Finkel et al., "Oxidants, Oxidative Stress and the Biology of Ageing" *Nature* 408: 239–47 (2000).
Gatley, S.J. & Martin, J.L, "Some Aspects of the Pharmacology of Diphenyleneiodonium, a Bivalent Iodine Compound" *Xenobiotica* 9: 539–546 (1979).
Holland et al. "Mechanism of Action of the Hypoglycemic Agent Diphenyleneiodonium" *J. Biol. Chem.* 248: 6050–6056 (1973).
Hotta et al., "Pancreatic β Cell–Specific Expression of Thioredoxin, an Antioxidative and Antiapoptotic Protein, Prevents Autoimmune and Streptozotocin–induced Diabetes" *Journal of Experimental Medicine* 188: 1445–51 (1998).
Inoguchi et al., "High Glucose Level and Free Fatty Acid Stimulate Reactive Oxygen Species Production Through Protein Kinase C–Dependent Activation of NAD(P)H Oxidase in Cultured Vascular Cells" *Diabetes* 49: 1939–1945 (2000).
Jones et al., "Expression of Phagocyte NADPH Oxidase Components in Human Endothelial Cells" *American Journal of Physiology* 271: H1626–34 (1996).
Knaus et al., "Purification and Characterization of Rac2" *Journal of Biological Chemistry,* 267: 23575–82 (1992).
Kozlovsky et al., "Reactive Oxygen Species Activate Glucose Transport in L6 Myotubes" *Free Radical Biology & Medicine* 23: 859–69 (1997).

(Continued)

Primary Examiner—Ralph Gitomer
(74) Attorney, Agent, or Firm—Fish & Richardson P.C.

(57) ABSTRACT

The present invention relates to the use of NAD(P)H oxidase inhibitors to increase cellular uptake of glucose and in the treatment and/or prevention of diseases caused by insulin resistance or diseases related thereto, such as type II diabetes. Specifically, the invention relates to a method for identifying an agent useful for the treatment or prophylaxis of a medical condition associated with elevated levels of blood glucose, the method comprising (i) contacting a candidate agent with a mammalian NAD(P)H oxidase or NAD(P)H oxidase complex; and (ii) determining whether said candidate agent inhibits the biological activities of the NAD(P)H oxidase or NAD(P)H oxidase complex.

8 Claims, 3 Drawing Sheets

OTHER PUBLICATIONS

Kozlovsky et al., "Transcriptional Activation of the Glut1 Gene in Response to Oxidative Stress in L6 Myotubes" *Journal of Biological Chemistry* 272: 33367–72 (1997).

Krieger–Brauer et al., "Insulin–Induced Activation of NADPH–dependent $H_2O_2$ Generation in Human Adipocyte Plasma Membranes in Mediated by $G\alpha_{i2}$" *Journal of Biological Chemistry*, 272: 10135–43 (1997).

Laight et al., "Pro–oxidant Challenge in vivo provokes the onset of NIDDM in the Insulin Resistant Obese Zuker rat" *British Journal of Pharmacology,* 128: 269–71 (1999).

May et al., "The Insulin–like Effect of Hydrogen Peroxide on Pathways of Lipid Synthesis in Rat Adipocytes" *Journal of Biological Chemistry* 254: 9017–21 (1979).

Paolisso et al., "Evidence for a Relationship Between Oxidative Stress and Insulin Active in Non–Insulin–Dependent (Type II) Diabetic Patients" *Metabolism: Clinical & Experimental* 43: 1426–29 (1994).

Rudich et al., "Oxidant Stress Reduces Insulin Responsiveness 3T3–L1 Adipocytes" *American Journal of Physiology* 272: E935–40 (1997).

Rudich et al., "Lipoic Acid Protects Against Oxidative Stress Induced Impairment in Insulin Stimulation of Protein Kinase B and Glucose Transport in 3T3–L1 Adipocytes" *Diabetologia* 42: 949–57 (1999).

Salonen et al., "Increase Risk of Non–insulin Dependent Diabetes Mellitus at Low Plasma Vitamin E Concentrations: A Four Year Follow up Study in Men" *BMJ* 311: 1124–27 (1995).

Segal et al., "The NADPH Oxidase of Phagocytic Leukocytes" *Journal of Ocular Pharmacology & Therapeutics Annals of the New York Academy of Sciences* 832: 215–22 (1997).

Spector, "Review: Oxidative Stress and Disease" 16: 193–201 (2000).

Sumimoto et al., "Cytochrome $b_{558}$, a Component of the Phagocyte NADPH Oxidase, is a Flavoprotein" *Biochemical & Biophysical Research Communications,* 186: 1368–75 (1992).

Tirosh et al., "Oxidative Stress Disrupts Insulin–Induced Cellular Redistribution of Insulin Receptor Substrate–1 and Phosphatidylinositol 3–Kinase in 3T3–L1 Adipocytes" *Journal of Biological Chemistry* 274: 10595–602 (1999).

\* cited by examiner

IDENTIFICATION OF AGENTS THAT INCREASE GLUCOSE UPTAKE

CROSS REFERENCE TO RELATED APPLICATIONS

This application claims priority from Swedish Patent Application No. 0201152-6, filed Apr. 17, 2002, and U.S. Provisional Patent Application Ser. No. 60/410,626, filed Sep. 13, 2002. These applications are incorporated herein by reference in their entirety.

TECHNICAL FIELD

The present invention relates to the use of NAD(P)H oxidase inhibitors to increase cellular uptake of glucose and in the treatment and/or prevention of diseases caused by insulin resistance or diseases related thereto, such as type II diabetes.

BACKGROUND ART

A large number of people suffer, or are predisposed to suffer from disturbances in their metabolism. One such disturbance includes insulin resistance, which is characteristic of the metabolic syndrome (syndrome X), polycystic ovary syndrome, obesity and type II diabetes, diseases that are rapidly growing in number in the western world. These diseases are multi-factorial and their mechanism or physiology are, in the majority of cases, not well characterized or understood. Type II diabetes includes the most prevalent form of diabetes, which results from insulin resistance with an insulin secretory defect. Pharmacological treatments such as metformin and rosiglitazone have an ameliorating effect on insulin resistance and are believed to increase the effectiveness of endogenous insulin and thereby contribute to the lowering of elevated blood glucose levels in type II diabetes patients.

One mechanism whereby insulin resistance may be induced is via elevation of reactive oxygen species (ROS). Although contrasting effects of ROS have been reported on the insulin signal transduction system and glucose transport, it has been shown that prolonged exposure of cells to ROS causes insulin resistance. Insulinomimetic effects of ROS have been reported using muscle cells and adipocytes. Acute exposure of adipocytes to $H_2O_2$ was shown to activate pyruvate dehydrogenase activity and lipid synthesis [May et al., Journal of Biological Chemistry, 254:9017–21 (1979)]. Some but not all aspects of insulin signaling appear to be activated by $H_2O_2$. Using L6 myocytes it was shown that $H_2O_2$ caused a P13K-dependent activation of PKB and inhibition of GSK3 within 30 min of treatment [Tirosh et al., Journal of Biological Chemistry, 274:10595–602 (1999)]. Prolonged treatment (24 h) of L6 muscle cells and 3T3-L1 adipocytes with a ROS generating system increased the expression of GLUT1 that resulted in elevated basal glucose transport [Kozlovsky et al., Free Radical Biology & Medicine, 23:859–69 (1997); Kozlovsky et al., Journal of Biological Chemistry, 272:33367–72 (1997)]. Treatment of these cell lines with $H_2O_2$ also interferes with insulin signaling [Rudich et al., American Journal of Physiology, 272:E935–40 (1997)]. Simultaneous treatment with insulin and $H_2O_2$ was shown to inhibit insulin stimulated glucose transport and glycogen synthesis in spite of intact PKB activation [Blair et al., Journal of Biological Chemistry, 274:36293–9 (1999)]. Pretreatment with ROS inhibited insulin stimulated IRS-1 and P13K cellular redistribution, PKB serine phosphorylation and glucose transport [Tirosh, Potashnik et al., Journal of Biological Chemistry, 274:10595–602 (1999)]. The antioxidant lipoic acid could prevent these effects [Rudich et al., Diabetologia, 42:949–57 (1999)]. Taken together, these results suggest that insulin signaling involve redox reactions, with some steps that can be mimicked and some that can be inhibited by $H_2O_2$. Integrating these findings with the demonstration that insulin can stimulate the production of $H_2O_2$, it can be hypothesized that ROS are involved in insulin signaling and may be responsible for the insulin resistance observed after prolonged treatment with insulin and other agents.

Oxidative stress is caused by excess free radical production in cellular metabolism. The free radicals derived from reaction products of oxygen are often termed reactive oxygen species (ROS). A reducing environment inside the cell prevents oxidative damage and can be maintained by the action of antioxidant enzymes and substances, such as superoxide dismutase (SOD), catalase, glutathione, selenium-dependent glutathione, thioredoxin hydroperoxidases, thioredoxin, vitamins C and E, and probably more unknown players.

Oxidative stress has been demonstrated in several different diseases and is implicated as an important driving force in the aging process [Finkel et al., Nature, 408:239–47 (2000); Spector, Journal of Ocular Pharmacology & Therapeutics, 16:193–201 (2000)]. A growing body of data demonstrate signs of increased oxidative stress in type II diabetes. It is likely that the oxidative stress is contributing to many of the vascular complications occurring in the late stages of the disease but the evidence for oxidative stress as causative factor in the development of insulin resistance and deterioration of beta cell function is still lacking. An inverse relationship between insulin action on glucose disposal and plasma superoxide ion, and a positive relationship between insulin action on glucose disposal and plasma GSH/GSSG ratio have been observed in type 2 diabetic patients during euglycemic hyperinsulinemic clamp [Paolisso et al., Metabolism: Clinical & Experimental, 43:1426–9 (1994)]. Decreased serum vitamin E content, a marker of impaired oxidant/antioxidant status, was reported to be associated with increased risk of developing type II diabetes [Salonen et al., BMJ, 311:1124–7 (1995)]. In animal experiments it was recently demonstrated that chemically induced oxidative stress exacerbated insulin resistance and hyperglycemia in obese Zucker rats [Laight et al., British Journal of Pharmacology, 128:269–71 (1999)]. There are also indications that beta cell toxic agents like alloxan and streptozotocin that are used to induce experimental animal diabetes act via oxidative stress [Davis et al., Biochemical Pharmacology, 55:1301–7 (1998); Hotta et al., Journal of Experimental Medicine, 188:1445–51 (1998)].

Superoxide can be produced by a number of cellular enzyme systems: NAD(P)H oxidases, xanthine oxidase, lipoxygenases, cyclooxygenase, P-450 monooxygenases, and the enzymes of mitochondrial oxidative phosphorylation. The majority of free radicals are produced by the mitochondria as unwanted by-products of the respiratory chain but the cell also purposely generates free radicals. The cellular defense system of the body utilizes oxygen radicals to kill invading microorganisms and the vascular system uses the nitric oxide radicals as an intermediate in the regulation of vascular tone. Originally, the NAD(P)H oxidase system responsible for production of superoxide that participates in bacterial killing was demonstrated in neutrophils and other phagocyte cells [Segal et al., Annals of the New York Academy of Sciences, 832:215–22 (1997)]. A growing number of experimental data from endothelial cells and other cell types show that ROS can be produced through activation of NAD(P)H-oxidase [Jones et al., American Journal of Physiology, 271:H1626–34 (1996); Krieger-Brauer et al., Journal of Biological Chemistry, 272:10135–43 (1997); Bayraktutan et al., Cardiovascular Research, 38:256–62 (1998)]. When activated, the NAD (P)H oxidase assembles at the plasma membrane and catalyses the single electron reduction of molecular $O_2$ to superoxide ($O_2^-$). In the presence of superoxide dismutase, $O_2^-$ dismutates to hydrogen peroxide ($H_2O_2$) that can be converted to a hydroxyl radical ($OH^-$) in the presence of ferrous ions. The list of other free radicals originating from $O_2^-$ that can be formed in the cell is longer, and will not be further discussed here. At least five proteins are required for the formation of an active NAD(P)H oxidase complex: the membrane bound cytochrome b558 and the cytosolic proteins, $p47^{phox}$, $p67^{phox}$, $p40^{phox}$ and a small GTP-binding protein, Rac-1 or Rac-2 [Abo et al., Journal of Biological Chemistry, 267:16767–70 (1992); Babior, Advances in Enzymology & Related Areas of Molecular Biology, 65:49–95 (1992); Knaus et al., Journal of Biological Chemistry, 267:23575–82 (1992)]. Cytochrome b558 is a flavoprotein with an NAD(P)H-binding site and consists of two subunits, $gp91^{phox}$ and $p22^{phox}$ [Sumimoto et al., Biochemical & Biophysical Research Communications, 186:1368–75 (1992)].

The hypoglycemic agent diphenylene iodinium (DPI) has been shown to diminish the rate of mitochondrial respiration by inhibiting NADH dehydrogenase. Holland et al. (1973; J. Biol. Chem. 248: 6050–6056) discloses that the enzyme inhibition causes the hypoglycemic action by decreasing mitochondrial oxidation and the hepatic and whole body ATP content (See also Gatley, S. J. & Martin, J. L. (1979) Xenobiotica 9: 539–546). However, it has not been previously shown that agents which inhibit NAD(P)H oxidase would be useful for increasing the activity of the insulin receptor and/or the intracellular insulin-signaling pathway, and thereby be useful against insulin resistance.

DISCLOSURE OF THE INVENTION

Figure 1:
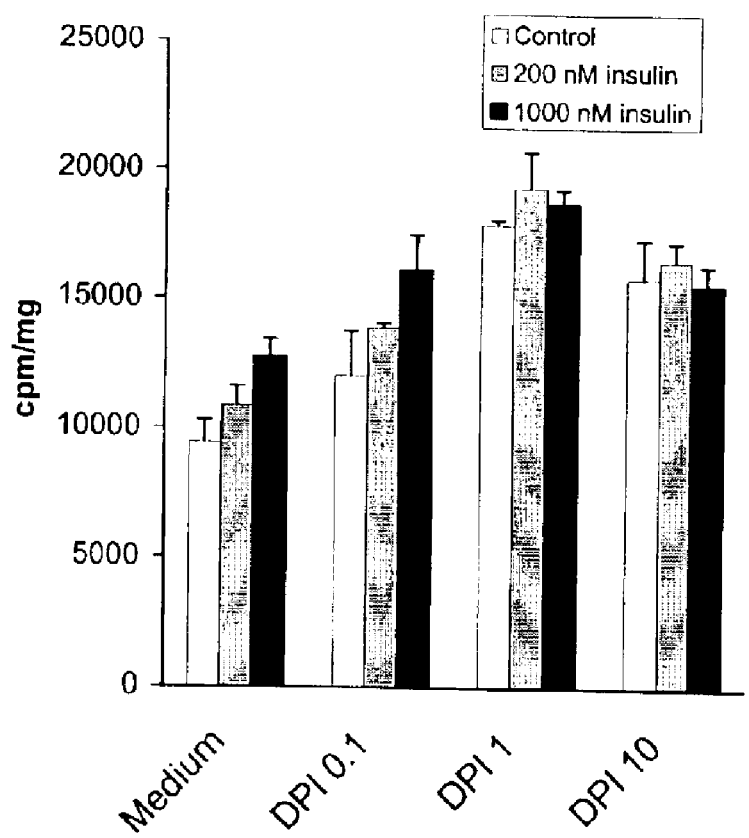
FIG. 1 is a graph depicting the effect of DPI on insulin stimulated glucose transport in L6 cells when treated with different concentrations (0.1–10 µM) of DPI alone for 30 min or together with insulin (200 or 1000 nM) for additional 30 min.

It has surprisingly been found that inhibition of NAD(P)H oxidase stimulates glucose uptake in rat skeletal muscle cells. A NAD(P)H oxidase complex is putatively involved in down-regulation of insulin signaling via generation of ROS. Thus, pharmacological inhibition of NAD(P)H oxidase activity should increase insulin signaling and restore insulin sensitivity. This surprising effect has not been seen previously and demonstrates the utility of the entire, or parts of, NAD(P)H oxidase complex, which generates ROS, as a tool for finding drugs that can be used for treating type II diabetes, specifically insulin resistance.

Consequently, in a first aspect this invention provides a method for identifying an agent useful for the treatment or prophylaxis of a medical condition associated with elevated levels of blood glucose, said method comprising (i) contacting a candidate agent with a mammalian NAD(P)H oxidase or NAD(P)H oxidase complex; and (ii) determining whether said candidate agent inhibits the biological activities of the NAD(P)H oxidase or NAD(P)H oxidase complex.

The said medical condition is preferably associated with insulin resistance, such as, in particular, type II diabetes. One clinical definition of diabetes is the so-called fasting glucose level. A patient is diagnosed with diabetes if the amount of glucose is above 126 milligrams per deciliter (mg/dl) measured on two occasions. Impaired fasting glucose and impaired glucose tolerance are associated with the insulin resistance syndrome. An individual can be insulin resistant in the absence of fasting hyperglycemia if an oral glucose tolerance test with 75 g anhydrous glucose dissolved in water gives a 2 h plasma glucose value $\geq$ 200 mg/dl in a test performed as described by WHO [World Health Organization, Tech. Rep. Ser., no. 727, (1985)].

In one embodiment of the invention, cells containing the NAD(P)H oxidase or the NAD(P)H oxidase complex may be brought into contact with inhibitors of the NAD(P)H oxidase or the NAD(P)H oxidase complex, followed by monitoring the glucose uptake by these cells, and comparing this activity with that of a the NAD(P)H oxidase or the NAD(P)H oxidase complex in the absence of inhibitor. Compounds that affect the glucose uptake of these cells are to be considered as potential drug candidates.

The NAD(P)H oxidase or NAD(P)H oxidase complex is preferably selected from the group consisting of gp91phox, p22phox, Mox2, Nox4, Nox5, DUOX1, DUOX2, (b5+b5R) oxidoreductase, p47phox, p67phox, p40phox, Rac-1, and Rac-2.

The proteins may be of any mammalian species, however, a preferred species is *Homo sapiens*. The nucleotide and amino acid sequences from *Homo sapiens* are disclosed in the enclosed sequence listing.

In one embodiment, the invention includes a method for identifying an agent that increases glucose uptake by a cell. The method includes the following steps: contacting a cell with a candidate agent that inhibits the activity of an NAD(P)H oxidase or an NAD(P)H oxidase complex; measuring glucose uptake by the cell in the presence of the candidate agent; and determining whether the candidate agent increases glucose uptake by the cell.

The method can optionally include an additional step of comparing glucose uptake by the cell in the presence of the candidate agent with glucose uptake by a cell in the absence of the candidate agent.

The method can optionally include a step of contacting the candidate agent with the NAD(P)H oxidase or the NAD(P)H oxidase complex and determining that the candidate agent inhibits the activity of the NAD(P)H oxidase or the NAD(P)H oxidase complex.

In one example, the NAD(P)H oxidase or the NAD(P)H oxidase complex is a human NAD(P)H oxidase or a human NAD(P)H oxidase complex. The NAD(P)H oxidase or the NAD(P)H oxidase complex can optionally be selected from the group consisting of gp91phox, p22phox, Mox2, Nox4, Nox5, DUOX1, DUOX2, (b5+b5R) oxidoreductase, p47phox, p67phox, p40phox, Rac-1, and Rac-2. The nucleic acid and amino acid sequences of exemplary NAD (P)H oxidases and NAD(P)H oxidase complexes are described herein.

The cell can be, for example, a muscle cell or an adipocyte.

In some embodiments, the candidate agent is selected from the group consisting of pyridine, imidazole, diethyl pyrocarbonate, chloromercuribenzoic acid, 4-(2-aminomethyl)-sulfonyl fluoride acetovanillone, and derivatives thereof.

In another aspect, the invention features a method for increasing glucose uptake in a cell by contacting a cell with an amount of an inhibitor of an NAD(P)H oxidase or an NAD(P)H oxidase complex effective to increase glucose uptake by the cell. The cell can be, for example, a muscle cell or an adipocyte. The method can optionally include an additional step of detecting an increase in glucose uptake by the cell in response to the contacting of the cell with the inhibitor.

In one example, the NAD(P)H oxidase or the NAD(P)H oxidase complex is a human NAD(P)H oxidase or a human NAD(P)H oxidase complex. The NAD(P)H oxidase or the NAD(P)H oxidase complex can optionally be selected from the group consisting of gp91phox, p22phox, Mox2, Nox4, Nox5, DUOX1, DUOX2, (b5+b5R) oxidoreductase, p47phox, p67phox, p4Ophox, Rac-1, and Rac-2. The nucleic acid and amino acid sequences of exemplary NAD(P)H oxidases and NAD(P)H oxidase complexes are described herein.

In some embodiments, the inhibitor is selected from the group consisting of pyridine, imidazole, diethyl pyrocarbonate, chloromercuribenzoic acid, 4-(2-aminomethyl)-sulfonyl fluoride acetovanillone, and derivatives thereof.

In another aspect, the invention provides a method for the treatment of a medical condition associated with elevated levels of blood glucose, comprising administering to a patient in need thereof an effective amount of an inhibitor or antagonist of NAD(P)H oxidase or NAD(P)H oxidase complex.

In one embodiment, the invention features a method for the treatment of a medical condition, including the following steps: selecting an individual diagnosed as having a medical condition characterized by elevated levels of blood glucose; and administering to the individual an amount of an inhibitor of an NAD(P)H oxidase or an NAD(P)H oxidase complex effective to reduce blood glucose levels in the individual.

The medical condition can be characterized by, for example, insulin resistance, a need for increased activity of the insulin receptor, and/or a need for increased activity of the intracellular insulin-signaling pathway.

In one example, the medical condition is diabetes, e.g., type II diabetes.

In some embodiments, the individual does not have and/or has not been diagnosed as having a disorder (e.g., atherosclerosis) characterized by a vascular injury, e.g., vascular hyperpermeability of endothelial cells. In addition, in some embodiments, the method does not include a step of evaluating a vascular injury (if present) in the individual before and/or after the administration of the inhibitor to the individual.

In some embodiments, the method includes an additional step of detecting a reduction in blood glucose levels in the individual in response to the administration of the inhibitor.

In one example, the NAD(P)H oxidase or the NAD(P)H oxidase complex is a human NAD(P)H oxidase or a human NAD(P)H oxidase complex. The NAD(P)H oxidase or the NAD(P)H oxidase complex can optionally be selected from the group consisting of gp91phox, p22phox, Mox2, Nox4, Nox5, DUOX1, DUOX2, (b5+b5R) oxidoreductase, p47phox, p67phox, p4Ophox, Rac-1, and Rac-2. The nucleic acid and amino acid sequences of exemplary NAD(P)H oxidases and NAD(P)H oxidase complexes are described herein.

In some embodiments, the inhibitor is selected from the group consisting of pyridine, imidazole, diethyl pyrocarbonate, chloromercuribenzoic acid, 4-(2-aminomethyl)-sulfonyl fluoride acetovanillone, and derivatives thereof.

The inhibitor or antagonist can be identified according to the method as described above. Examples of known inhibitors or antagonists are those selected from the group consisting of pyridine, imidazole, diethyl pyrocarbonate, chloromercuribenzoic acid, 4-(2-aminomethyl)-sulfonyl fluoride and acetovanillone, including derivatives thereof. The said inhibitor or antagonist is e.g. a compound having an inhibitory effect on the ROS generating activity of the NAD(P)H oxidase or the NAD(P)H oxidase complex. The inhibitor or antagonist could exert its effect by interacting with the active site or a regulatory site, or both sites, of the NAD(P)H oxidase.

A compound that shows the desirable characteristics with regards to inhibiting the activity of the NAD(P)H oxidase or the NAD(P)H oxidase complex will be further tested in an assay of insulin stimulated glucose uptake in differentiated L6-K1 cells or other skeletal muscle cells, muscle tissue biopsies, adipocytes or adipocyte cell lines. An active compound should stimulate basal and insulin stimulated glucose uptake in a manner similar to the NAD(P)H oxidase inhibitor diphenylene iodonium (DPI). The compounds will preferably be of such nature that they are suited for oral administration, but any route of administration, such as, intravenous, suppository or parental routes will be considered.

In yet another aspect, the invention provides the use of an NAD(P)H oxidase- or NAD(P)H oxidase complex inhibitor or antagonist, as described above, in the manufacture of a medicament for the treatment and/or prevention of a medical condition connected with elevated levels of blood glucose.

As defined herein, the term "prevent" or "treat" is not intended to exclusively mean the complete abolishment of the disease or condition, but is meant that there is complete or some amelioration, so that an improvement over the expected symptomology is clinically observed. An example of one such criterion could be the lowering of blood glucose levels by more than 25%. Other such criteria, well known in the art, could be envisioned.

As defined herein, the term "reactive oxygen species" means compounds selected from the group comprising compounds or compound species such as $H_2O_2$, $OH^-$ and $O_2^-$. Compounds such as these will be referred to as "ROS".

As defined herein, the term "NAD(P)H oxidase" or "NAD(P)H oxidase complex" means one of the proteins or any combination of two or more of the proteins selected from the group comprising the membrane bound cytochrome b558 consisting of $gp_{91}^{phox}$ (nucleotide sequence according to SEQ ID NO:1, amino acid sequence according to SEQ ID NO:2), $p_{22}^{phox}$ (nucleotide sequence according to SEQ ID NO:3, amino acid sequence according to SEQ ID NO:4), Mox2 (nucleotide sequence according to SEQ ID NO:5, amino acid sequence according to SEQ ID NO:6), Nox4 (nucleotide sequence according to SEQ ID NO:7, amino acid sequence according to SEQ ID NO:8), Nox5 (nucleotide sequence according to SEQ ID NO:9, amino acid sequence according to SEQ ID NO:10), DUOX1 (nucleotide sequence according to SEQ ID NO: 11, amino acid sequence according to SEQ ID NO:12), p138Tox (DUOX2) (nucleotide sequence according to SEQ ID NO: 13, amino acid sequence according to SEQ ID NO: 14), (b5+b5R) oxidoreductase (nucleotide sequence according to SEQ ID NO: 15, amino acid sequence according to SEQ ID NO: 16), and the cytosolic proteins, $p_{47}^{phox}$ (nucleotide sequence according to SEQ ID NO: 17, amino acid sequence according to SEQ ID NO: 18), $p67^{phox}$ (nucleotide sequence according to SEQ ID NO: 19, amino acid sequence according to SEQ ID NO:20), $p40^{phox}$ (nucleotide sequence according to SEQ ID NO:21, amino acid sequence according to SEQ ID NO:22),and a small GTP-binding protein, Rac-1, (which has two different amino acid variants), (nucleotide sequence according to SEQ ID NO:23, amino acid sequence according to SEQ ID NO:24 and SEQ ID NO:25, respectively), or Rac-2, (nucleotide sequence according to SEQ ID NO:26, amino acid sequence according to SEQ ID NO:27), which combination gives rise to reactive oxygen species, or other proteins or assemblies of proteins which essentially have NAD(P)H oxidase activity. Preferably, these enzymes contain consensus sequences for FAD- and/or NAD(P)H-binding sites.

In addition to the specific NAD(P)H oxidase amino acid and nucleotide sequences described herein, fragments or variants thereof that retain NAD(P)H oxidase activity (or fragments or variants thereof that encode polypeptides that retain such activity) can be used in the methods of the invention (e.g., screening methods).

In some embodiments, a polypeptide used in a method of the invention differs from an NAD(P)H oxidase amino acid sequence described herein at one or more residues and yet retains NAD(P)H oxidase activity. The differences are, preferably, differences or changes at a non-essential residue or a conservative substitution. In one embodiment, a polypeptide includes an amino acid sequence that is at least about 60% identical to an NAD(P)H oxidase amino acid sequence described herein or a fragment thereof. Preferably, the polypeptide is at least 65%, 70%, 75%, 80%, 85%, 90%, 95%, 98%, 99% or more identical to an NAD(P)H oxidase amino acid sequence described herein. Preferred polypeptide fragments are at least 10%, preferably at least 20%, 30%, 40%, 50%, 60%, 70%, or more, of the length of an NAD(P)H oxidase amino acid sequence described herein.

As used herein, "% identity" of two amino acid sequences, or of two nucleic acid sequences, is determined using the algorithm of Karlin and Altschul (PNAS USA 87:2264–2268, 1990), modified as in Karlin and Altschul, PNAS USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al (Nucleic Acids Res. 25:3389–3402, 1997). When utilizing BLAST and GappedBLAST programs the default parameters of the respective programs (e.g., XBLAST and NBLAST) are used to obtain nucleotide sequences homologous to a nucleic acid molecule described herein.

The term "NAD(P)H oxidase activity", as described herein, refers to enzymatic activity of either the NAD(P)H oxidase or the NAD(P)H oxidase complex, as defined herein, whereby reactive oxygen species (ROS) are produced. Such enzymatic activity is readily established and procedures for this are well known to a skilled person. This activity is well known in the art and methods whereby this can be monitored are well known.

The term "inhibiting" with regards to ROS generating activity of the NAD(P)H oxidase or the NAD(P)H oxidase complex is meant the lowering of said activity to the range between 20%–100% of normal activity when measured with said methods. A preferred value of the inhibitory constant $K_i$ is <10 $\mu$M, or more preferably <1 $\mu$M.

As defined herein, the term "NAD(P)H oxidase inhibitor" means any compound capable of lowering the activity of the NAD(P)H oxidase or the NAD(P)H oxidase complex, according to the above mentioned definition.

When activated, the NAD(P)H oxidase complex assembles at the plasma membrane and catalyses the single electron reduction of molecular $O_2$ to superoxide ($°O_2^-$). In the presence of superoxide dismutase, $O_2^-$ dismutates to hydrogen peroxide ($H_2O_2$) that can be converted to a hydroxyl radical ($OH^-$) in the presence of ferrous ions. The list of other free radicals originating from $O_2^-$ that can be formed in the cell is longer, and will not be further discussed here. Several proteins are required for the formation of an active NAD(P)H oxidase complex and may include: p22phox, Mox2, Nox4, Nox5, DUOX1, DUOX2, (b5+b5R) oxidoreductase, p47phox, p67phox, p40phox, Rac-1, Rac-2 [Lambeth et al. (2000) Trends Biochem. Sci. 25: 459–461].

A fully active complex producing oxygen radicals in the presence of NAD(P)H, FAD, GTP and amphiphilic compounds can be reconstituted in vitro with individual recombinant proteins [Rotrosen et al., Journal of Biological Chemistry, 268:14256–60 (1993)].

The invention will now be demonstrated by the following examples. These examples are for the purpose of illustration only and are not intended to limit the scope of the invention in any way. The information necessary for carrying out these experiments is supplied in the references. Any variations and adjustments that need to be made for correct function of these assays (variations in pH, concentration ranges, etc) will be apparent for a skilled person.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

The NAD(P)H Oxidase Inhibitor DPI Increases Glucose Uptake in Rat Skeletal Muscle Cells Cell culture medium, fetal bovine serum, antibiotics, trypsin-EDTA were purchased from Life Technologies. Diphenylene iodonium (DPI), cytidine, bovine insulin, bovine serum albumin, and glucose oxidase were purchased from Sigma. 2-Deoxy-[$^3$H] glucose (specific activity 1102.6 GBq/mmol) was purchased from NEN Life Science Products and 2-Deoxy-[$^{14}$C] glucose from Amersham Pharmacia Biotech. Tissue culture plastics were purchased from Becton Dickinson.

Rat skeletal muscle L6-K cells were grown in minimal essential medium (α-MEM Glutamax I) containing 10% fetal bovine serum at 37° C., 5% $CO_2$. The cells were passaged twice weekly by treatment with trypsin-EDTA and transfer of ⅓ of the cells to new flasks with fresh culture medium. For differentiation into myotubes, 30,000 cells were seeded in 1 ml in 24-well plates. When the cells were confluent, usually after 3 days, the medium was replaced by differentiation medium consisting of α-MEM, 2% fetal bovine serum and penicillin/streptomycin at a concentration of 100 U/ml and 100 μg/ml, respectively. The medium was replaced every 2–3 days. Between days 4–7, differentiation medium containing 1 mM cytidine was used. The cells were differentiated for 8–10 days before being used in experiments.

On the day before the glucose transport assay, the wells of the culture plate were emptied and 1 ml serum free DMEM containing 5 mM glucose and penicillin/streptomycin was added. In some experiments the cells were treated over night with test compounds in 1 ml and additional treatments were added the next day to give a total volume of 2 ml. In these experiments, insulin (100–1000 nM) was added in 0.2 ml. When all treatments were performed after 20–24 h in serum free medium, a total volume of 1 ml was used. The wells were emptied and 0.5 ml prewarmed PBS without $Ca^{2+}$/$Mg^{2+}$ containing 1 μCi/ml radioactive 2-deoxy-glucose added. After 10 min at 37° C., the wells were emptied and washed three times with cold PBS. The cell monolayer was solubilized in 0.5 ml 0.5 M NaOH for 3 h at room temperature. 400 μl was mixed with 8 ml scintillation fluid (Optiphase, Wallac) and counted in a scintillation counter (Packard TriCarb). Two 10-μl aliquots were used for determination of protein concentration using the method according to Bradford (Anal. Biochem., 1976, 72:248–54) from BioRad.

When differentiated L6 cells are incubated with the NAD(P)H oxidase inhibitor DPI [O'Donnell V.B. et al. (1993) Biochem. J. 290: 41–49] a significant increase in glucose uptake can be observed (FIG. 1). This increase is comparable to or greater than that caused by insulin. This effect is seen when cells are stimulated with 0.1–10 μM DPI for 1 h. A bell-shaped dose response curve for DPI with an optimum at 1 μM is recorded. The effect of suboptimal concentrations of DPI during a 1 h treatment could be stimulated further if insulin is added 30 min after DPI. However, insulin has little additional effect when the maximum effect of DPI is reached in the 1 h protocol (FIG. 1). The effective concentrations at which DPI stimulates glucose transport corresponds well to the concentrations inhibiting NAD(P)H oxidase activity in cell free systems [O'Donnell et al., Biochemical Journal, 290:41–9 (1993)]. These results suggest that DPI stimulates glucose transport via activation of the same mechanism as insulin. On the basis of the above results it is postulated that DPI enhances a constitutive activity of the insulin receptor and/or the intracellular insulin-signaling pathway. The existence of such a constitutive activity is suggested from experiments in which adipocytes have been transfected with the tyrosine phosphatase PTP 1B [Chen et al., Journal of Biological Chemistry, 272:8026–31 (1997)]. These data are compatible with DPI augmenting constitutive intracellular signaling via the same pathway that is used by insulin.

Example 2

Glucose Oxidase Reduces the Effect of DPI on Glucose Uptake

Assuming that the enhancing effect of DPI on insulin signaling was due to inhibition of ROS production, it was investigated whether an exogenous source of $H_2O_2$ could counteract the effect of DPI. To this end, L6 cells were treated with 25 mU/ml of glucose oxidase for 30 min before addition of DPI. Such a treatment has previously been shown to result in a steady production of micromolar concentrations of $H_2O_2$ that can freely pass the cell membrane and cause inhibition of insulin signaling [Tirosh, Potashnik et al., Journal of Biological Chemistry, 274:10595–602 (1999)].

Figure 2:
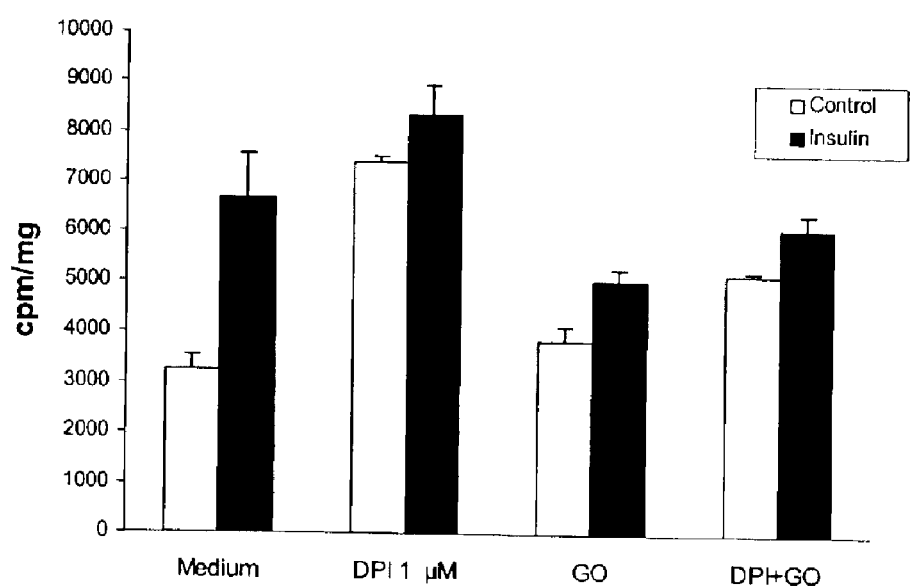
FIG. 2 is a graph depicting the effect of $H_2O_2$ generated by glucose oxidase (GO) DPI stimulated glucose transport. Differentiated L6 cells were treated with 25 mU/ml GO for 30 min before addition of DPI. After additional 30 min, 200 nM insulin was added and glucose transport was measured after 30 min.

It was found that glucose oxidase reduced the stimulatory effect of DPI by 68% and insulin stimulated glucose transport by 65% (FIG. 2). The available results suggest that $H_2O_2$ can counteract the effect of DPI in addition to inducing insulin resistance. This further strengthens the similarity between the effects of insulin and DPI and shows that DPI acts by inhibiting $H_2O_2$ production. In spite of superoxide being the primary product of NAD(P)H oxidase, $H_2O_2$ is the main effector in the cell since superoxide is converted to $H_2O_2$ by superoxide dismutase.

Example 3

DPI Decreases Blood Glucose Levels in Ob/Ob Mice

Studies were conducted in vivo, in an animal model of obesity characterized by insulin resistance. Eight-month old C57BL/6J ob/ob mice (M&B A/S, Denmark) were matched for sex, weight and fasting blood glucose concentrations. The animals were injected intraperitoneally once daily with DPI (1 mg/kg) or water for 4 days. On day 5, the animals were fasted for 2.5 h and then given an i.p. injection of human insulin 0.5 U/kg (Actrapid, Novo Nordisk, Denmark) and their blood glucose levels were monitored for 4 h by sampling from the tail. The glucose concentration was determined using a Glucometer Accutrend Sensor (Roche).

Figure 3:
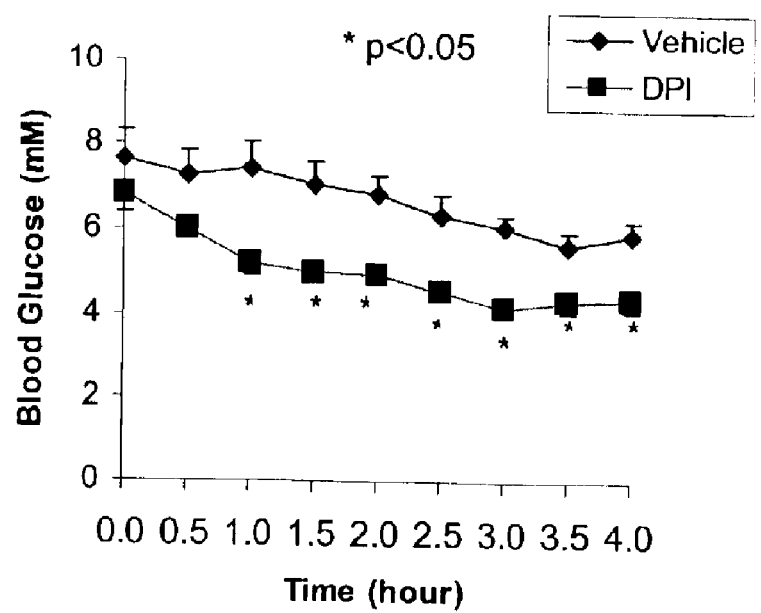
FIG. 3 is a graph depicting blood glucose concentrations during an insulin tolerance test in ob/ob mice treated for 4 days with daily i.p. injections of DPI, 1 mg/kg (n=7), or vehicle (n=8).

Without any overt side effects of the DPI treatment, the treated animals exhibited significantly lower blood glucose levels than the control group 1–4 h after injection of insulin, suggesting a decreased insulin resistance (FIG. 3).

Example 4

Identification of Agents Inhibiting NAD(P)H Oxidase

Methods to be used for identifying compounds that inhibit the activity of the NAD(P)H oxidase complex are illustrated.

(A) Neutrophil membrane and cytosol assay for superoxide mediated cytochrome c reduction (Diatchuk, V. et al. (1997) J. Biol. Chem. 272: 13292–13301). Sources of neutrophil membranes and cytosol from buffy coats of normal donors are obtainable from the Blood Bank. Enzyme cofactors and cytochrome c for detection of superoxide-mediated reduction are commercially available. The assay is based on a color change that occurs upon reduction of cytochrome c. This change can be measured as a change in light absorbance using a standard microplate spectrophotometer.

(B) Neutrophil membrane+recombinant $p_{47}^{phox}$, $p67^{phox}$ and rac1 for superoxide mediated cytochrome c reduction (absorbance) (Nisimoto, Y. et al. (1997) J. Biol. Chem. 272: 18834–18841).

(C) Fully recombinant NAD(P)H oxidase assay for superoxide mediated cytochrome c reduction [Rotrosen, D. et al, (1993) J. Biol. Chem. 268: 14256–14260].

(D) Fluorescence assay, which measures the interaction between rac and $p67^{phox}$ [Nisimoto, Y. et al. (1997) J. Biol.

Chem. 272: 18834–18841]. This assay would limit the screening to detection of compounds interfering with this particular step in the activation of the oxidase. The fluorescent GTP analog 2'-(or-3')-O-(N-methylanthraniloyl)-βγ-imidoguanosine 5'-triphosphate (MANT-GMPPNP, available from Molecular Probes), binds tightly to Rac, and shows an increase in fluorescence when p67$^{phox}$ is added, indicating complex formation. Rac1 and Rac2 bind to p67$^{phox}$ with a 1:1 stoichiometry and with Kd values of 120 nM and 60 nM, respectively.

(E) Binding assay utilizing $^{125}$I- or fluorescence labeled mastoparan. Mastoparan is a peptide present in wasp venom that has been shown to inhibit NAD(P)H oxidase activation, most likely via its ability to bind to p67$^{phox}$ [Tisch-Idelson, D., et al.(2001) Biochemical Pharmacology 61: 1063–1071].

(F) Test compounds can be analyzed in a nitroblue tetrazolium reduction assay utilizing a thioredoxin-gp91$^{phox}$ fusion protein. This protein has weak diaphorase activity in the presence of NAD(P)H and FAD and is inhibited by DPI.

(G) Test compounds can be added in appropriate amounts to cultured cells. The reactive oxygen species released from said cells may be measured with the use of a probe, resorufin, which becomes fluorescent in the presence of hydrogen peroxide and a peroxidase [Zhou, M. et al., (1997) Anal. Biochem., 253: 162–168].

Intracellular production of ROS can be measured with the use of various cell permeable analogs of dichlorofluorescin acetate as described by Xie, J. I. et al.[(1999) J. Biol. Chem. 274: 19323–19328].

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method for identifying an agent that increases glucose uptake by a cell, the method comprising:

contacting a cell with a candidate agent that inhibits the activity of an NAD(P)H oxidase or an NAD(P)H oxidase complex;

measuring glucose uptake by the cell in the presence of the candidate agent; and determining whether the candidate agent increases glucose uptake by the cell.

2. The method of claim 1, wherein the NAD(P)H oxidase or the NAD(P)H oxidase complex is a human NAD(P)H oxidase or a human NAD(P)H oxidase complex.

3. The method of claim 1, wherein the cell is a muscle cell.

4. The method of claim 1, wherein the cell is an adipocyte.

5. The method of claim 1, wherein the NAD(P)H oxidase or the NAD(P)H oxidase complex is selected from the group consisting of gp91phox, p22phox, Mox2, Nox4, Nox5, DUOX1, DUOX2, (b5+b5R) oxidoreductase, p47phox, p67phox, p40phox, Rac-1, and Rac-2.

6. The method of claim 1, wherein the candidate agent is selected from the group consisting of pyridine, imidazole, diethyl pyrocarbonate, chloromercuribenzoic acid, 4-(2-aminomethyl)-sulfonyl fluoride acetovanillone, and derivatives thereof.

7. The method of claim 1, further comprising comparing glucose uptake by the cell in the presence of the candidate agent with glucose uptake by a cell in the absence of the candidate agent.

8. The method of claim 1, further comprising contacting the candidate agent with the NAD(P)H oxidase or the NAD(P)H oxidase complex and determining that the candidate agent inhibits the activity of the NAD(P)H oxidase or the NAD(P)H oxidase complex.

* * * * *

SEQUENCE LISTING

<160> NUMBER OF SEQ ID NOS: 27

<210> SEQ ID NO 1
<211> LENGTH: 4266
<212> TYPE: DNA
<213> ORGANISM: Homo sapiens

<400> SEQUENCE: 1

```
cttcctctgc caccatgggg aactgggctg tgaatgaggg gctctccatt tttgtcattc      60
tggtttggct ggggttgaac gtcttcctct ttgtctggta ttaccgggtt tatgatattc     120
cacctaagtt cttttacaca agaaaacttc ttgggtcagc actggcactg gccagggccc     180
ctgcagcctg cctgaatttc aactgcatgc tgattctctt gccagtctgt cgaaatctgc     240
tgtccttcct caggggttcc agtgcgtgct gctcaacaag agttcgaaga caactggaca     300
ggaatctcac ctttcataaa atggtggcat ggatgattgc acttcactct gcgattcaca     360
ccattgcaca tctatttaat gtggaatggt gtgtgaatgc ccgagtcaat aattctgatc     420
cttattcagt agcactctct gaacttggag acaggcaaaa tgaaagttat ctcaattttg     480
ctcgaaagag aataaagaac cctgaaggag gcctgtacct ggctgtgacc ctgttggcag     540
gcatcactgg agttgtcatc acgctgtgcc tcatattaat tatcacttcc tccaccaaaa     600
ccatccggag gtcttacttt gaagtctttt ggtacacaca tcatctcttt gtgatcttct     660
tcattggcct tgccatccat ggagctgaac gaattgtacg tgggcagacc gcagagagtt     720
tggctgtgca taatataaca gtttgtgaac aaaaaatctc agaatgggga aaaataaagg     780
aatgcccaat ccctcagttt gctggaaacc ctcctatgac ttggaaatgg atagtgggtc     840
ccatgtttct gtatctctgt gagaggttgg tgcggttttg gcgatctcaa cagaaggtgg     900
tcatcaccaa ggtggtcact caccctttca aaaccatcga gctacagatg aagaagaagg     960
ggttcaaaat ggaagtggga caatacattt ttgtcaagtg cccaaaggtg tccaagctgg    1020
agtggcaccc ttttacactg acatccgccc ctgaggaaga cttctttagt atccatatcc    1080
gcatcgttgg ggactggaca gagggctgt tcaatgcttg tggctgtgat aagcaggagt    1140
ttcaagatgc gtggaaacta cctaagatag cggttgatgg gccctttggc actgccagtg    1200
aagatgtgtt cagctatgag gtggtgatgt tagtgggagc agggattggg gtcacaccct    1260
```

```
tcgcatccat tctcaagtca gtctggtaca aatattgcaa taacgccacc aatctgaagc    1320
tcaaaaagat ctacttctac tggctgtgcc gggacacaca tgcctttgag tggtttgcag    1380
atctgctgca actgctggag agccagatgc aggaaaggaa caatgccggc ttcctcagct    1440
acaacatcta cctcactggc tgggatgagt ctcaggccaa tcactttgct gtgcaccatg    1500
atgaggagaa agatgtgatc acaggcctga acaaaagac tttgtatgga cggcccaact    1560
gggataatga attcaagaca attgcaagtc aacaccctaa taccagaata ggagttttcc    1620
tctgtggacc tgaagccttg gctgaaaccc tgagtaaaca aagcatctcc aactctgagt    1680
ctggccctcg gggagtgcat ttcatttca acaaggaaaa cttctaactt gtctcttcca    1740
tgaggaaata aatgtgggtt gtgctgccaa atgctcaaat aatgctaatt gataatataa    1800
ataccccctg cttaaaaatg gacaaaaaga aactataatg taatggtttt cccttaaagg    1860
aatgtcaaag attgtttgat agtgataagt tacatttatg tggagctcta tggttttgag    1920
agcactttta caaacattat ttcattttt tcctctcagt aatgtcagtg gaagttaggg    1980
aaaagattct tggactcaat tttagaatca aagggaaag gatcaaaagg ttcagtaact    2040
tccctaagat tatgaaactg tgaccagatc tagcccatct tactccaggt ttgatactct    2100
ttccacaata ctgagctgcc tcagaatcct caaaatcagt ttttatattc cccaaaagaa    2160
gaaggaaacc aaggagtagc tatatatttc tactttgtgt catttttgcc atcattatta    2220
tcatactgaa ggaaattttc cagatcatta ggacataata catgttgaga gtgtctcaac    2280
acttattagt gacagtattg acatctgagc atactccagt ttactaatac agcagggtaa    2340
ctgggccaga tgttctttct acagaagaat attggattga ttggagttaa tgtaatactc    2400
atcatttacc actgtgcttg gcagagagcg gatactcaag taagttttgt taaatgaatg    2460
aatgaattta gaaccacaca atgccaagat agaattaatt taaagcctta aacaaaattt    2520
atctaaagaa ataacttcta ttactgtcat agaccaaagg aatctgattc tccctagggt    2580
caagaacagg ctaaggatac taaccaatag gattgcctga agggttctgc acattcttat    2640
ttgaagcatg aaaaaagagg gttggaggtg gagaattaac ctcctgccat gactctggct    2700
catctagtcc tgctccttgt gctataaaat aaatgcagac taatttcctg cccaaagtgg    2760
tcttctccag ctagccctta tgaatattga acttaggaat tgtgacaaat atgtatctga    2820
tatggtcatt tgttttaaat aacacccacc ccttattttc cgtaaataca cacacaaaat    2880
ggatcgcatc tgtgtgacta atggtttatt tgtattatat catcatcatc atcctaaaat    2940
taacaaccca gaaacaaaaa tctctataca gagatcaaat tcacactcaa tagtatgttc    3000
tgaatatatg ttcaagagag agtctctaaa tcactgttag tgtggccaag agcagggttt    3060
tctttttgtt cttagaactg ctcccatttc tgggaactaa aaccagtttt atttgcccca    3120 cccttggag ccacaaatgt ttagaactct tcaacttcgg taatgaggaa gaaggagaaa    3180 gagctgggg aagggcagaa gactggttta ggaggaaaag gaaataagga gaaagagaa    3240 tgggagagtg agagaaaata aaaaaggcaa aagggagaga gagggaagg gggtctcata    3300 ttggtcattc cctgccccag atttcttaaa gtttgatatg tatagaatat aattgaagga    3360
ggtatacaca tactgatgtt gttttgatta tctatggtat tgaatctttt aaaatctggt    3420
cacaaatttt gatgctgagg gggattattc aaggactag gatgaactaa ataagaactc    3480
agttgttctt tgtcatacta ctattccttt cgtctcccag aatcctcagg gcactgaggg    3540
taggtctgac aaaataaggcc tgctgtgcga atatagcctt tctgaaatgt accaggatgg    3600
tttctgctta gagacactta ggtccagcct gttcacactg cacctcaggt atcaattcat    3660
```

-continued

```
ctattcaaca gatatttatt gtgttattac tatgagtcag gctctgttta ttgtttcaat    3720
tctttacacc aaagtatgaa ctggagaggg tacctcagtt ataaggagtc tgagaatatt    3780
ggccctttct aacctatgtg cataattaaa accagcttca tttgttgctc cgagagtgtt    3840
tctccaaggt tttctatctt caaaaccaac taagttatga aagtagagag atctgccctg    3900
tgttatccag ttatgagata aaaaatgaat ataagagtgc ttgtcattat aaaagtttcc    3960
tttttatctc tcaagccacc agctgccagc caccacgagc cagctgccag cctagctttt    4020
tttttttttt ttttttttagc acttagtatt tagcatttat taacaggtac tctaagaatg    4080
atgaagcatt gttttaatc ttaagactat gaaggttttt cttagttctt ctgcttttgc      4140
aattgtgttt gtgaaatttg aatacttgca ggctttgtat gtgaataatt ctagcggggg    4200
acctgggaga taattctacg gggaattctt aaaactgtgc tcaactatta aaatgaatga    4260
gctttc                                                              4266
```

<210> SEQ ID NO 2
<211> LENGTH: 570
<212> TYPE: PRT
<213> ORGANISM: Homo sapiens

<400> SEQUENCE: 2

```
Met Gly Asn Trp Ala Val Asn Glu Gly Leu Ser Ile Phe Val Ile Leu
1               5                   10                  15

Val Trp Leu Gly Leu Asn Val Phe Leu Phe Val Trp Tyr Tyr Arg Val
                20                  25                  30

Tyr Asp Ile Pro Pro Lys Phe Phe Tyr Thr Arg Lys Leu Leu Gly Ser
            35                  40                  45

Ala Leu Ala Leu Ala Arg Ala Pro Ala Ala Cys Leu Asn Phe Asn Cys
        50                  55                  60

Met Leu Ile Leu Leu Pro Val Cys Arg Asn Leu Leu Ser Phe Leu Arg
65                  70                  75                  80

Gly Ser Ser Ala Cys Cys Ser Thr Arg Val Arg Arg Gln Leu Asp Arg
                85                  90                  95

Asn Leu Thr Phe His Lys Met Val Ala Trp Met Ile Ala Leu His Ser
            100                 105                 110

Ala Ile His Thr Ile Ala His Leu Phe Asn Val Glu Trp Cys Val Asn
        115                 120                 125

Ala Arg Val Asn Asn Ser Asp Pro Tyr Ser Val Ala Leu Ser Glu Leu
    130                 135                 140

Gly Asp Arg Gln Asn Glu Ser Tyr Leu Asn Phe Ala Arg Lys Arg Ile
145                 150                 155                 160

Lys Asn Pro Glu Gly Gly Leu Tyr Leu Ala Val Thr Leu Leu Ala Gly
                165                 170                 175

Ile Thr Gly Val Val Ile Thr Leu Cys Leu Ile Leu Ile Thr Ser
            180                 185                 190

Ser Thr Lys Thr Ile Arg Arg Ser Tyr Phe Glu Val Phe Trp Tyr Thr
        195                 200                 205

His His Leu Phe Val Ile Phe Phe Ile Gly Leu Ala Ile His Gly Ala
    210                 215                 220

Glu Arg Ile Val Arg Gly Gln Thr Ala Glu Ser Leu Ala Val His Asn
225                 230                 235                 240

Ile Thr Val Cys Glu Gln Lys Ile Ser Glu Trp Gly Lys Ile Lys Glu
                245                 250                 255
```

```
Cys Pro Ile Pro Gln Phe Ala Gly Asn Pro Pro Met Thr Trp Lys Trp
                260                 265                 270
Ile Val Gly Pro Met Phe Leu Tyr Leu Cys Glu Arg Leu Val Arg Phe
            275                 280                 285
Trp Arg Ser Gln Gln Lys Val Val Ile Thr Lys Val Val Thr His Pro
        290                 295                 300
Phe Lys Thr Ile Glu Leu Gln Met Lys Lys Gly Phe Lys Met Glu
305                 310                 315                 320
Val Gly Gln Tyr Ile Phe Val Lys Cys Pro Lys Val Ser Lys Leu Glu
                325                 330                 335
Trp His Pro Phe Thr Leu Thr Ser Ala Pro Glu Asp Phe Ser
            340                 345                 350
Ile His Ile Arg Ile Val Gly Asp Trp Thr Glu Gly Leu Phe Asn Ala
        355                 360                 365
Cys Gly Cys Asp Lys Gln Glu Phe Gln Asp Ala Trp Lys Leu Pro Lys
370                 375                 380
Ile Ala Val Asp Gly Pro Phe Gly Thr Ala Ser Glu Asp Val Phe Ser
385                 390                 395                 400
Tyr Glu Val Val Met Leu Val Gly Ala Gly Ile Gly Val Thr Pro Phe
                405                 410                 415
Ala Ser Ile Leu Lys Ser Val Trp Tyr Lys Tyr Cys Asn Asn Ala Thr
            420                 425                 430
Asn Leu Lys Leu Lys Lys Ile Tyr Phe Tyr Trp Leu Cys Arg Asp Thr
        435                 440                 445
His Ala Phe Glu Trp Phe Ala Asp Leu Leu Gln Leu Leu Glu Ser Gln
    450                 455                 460
Met Gln Glu Arg Asn Asn Ala Gly Phe Leu Ser Tyr Asn Ile Tyr Leu
465                 470                 475                 480
Thr Gly Trp Asp Glu Ser Gln Ala Asn His Phe Ala Val His Asp
            485                 490                 495
Glu Glu Lys Asp Val Ile Thr Gly Leu Lys Gln Lys Thr Leu Tyr Gly
            500                 505                 510
Arg Pro Asn Trp Asp Asn Glu Phe Lys Thr Ile Ala Ser Gln His Pro
        515                 520                 525
Asn Thr Arg Ile Gly Val Phe Leu Cys Gly Pro Glu Ala Leu Ala Glu
    530                 535                 540
Thr Leu Ser Lys Gln Ser Ile Ser Asn Ser Glu Ser Gly Pro Arg Gly
545                 550                 555                 560
Val His Phe Ile Phe Asn Lys Glu Asn Phe
                565                 570

<210> SEQ ID NO 3
<211> LENGTH: 687
<212> TYPE: DNA
<213> ORGANISM: Homo sapiens

<400> SEQUENCE: 3
gcagtgtccc agccgggttc gtgtcgccat ggggcagatc gagtgggcca tgtgggccaa      60
cgagcaggcg ctggcgtccg gcctgatcct catcaccggg gcatcgtgg ccacagctgg     120
gcgcttcacc cagtggtact ttggtgccta ctccattgtg gcgggcgtgt ttgtgtgcct     180
gctggagtac ccccggggga agaggaagaa gggctccacc atggagcgct ggggacagaa     240
gcacatgacc gccgtggtga agctgttcgg gcccttacc aggaattact atgttcgggc     300
cgtcctgcat ctcctgctct cggtgcccgc cggcttcctg ctggccacca tccttgggac     360
```

-continued

```
cgcctgcctg gccattgcga gcggcatcta cctactggcg gctgtgcgtg gcgagcagtg      420
gacgcccatc gagcccaagc cccgggagcg gccgcagatc ggaggcacca tcaagcagcc      480
gcccagcaac ccccgccgc ggccccggc cgaggcccgc aagaagccca gcgaggagga        540
ggctgcggcg gcggcggggg gaccccgg aggtccccag gtcaacccca tcccggtgac        600
cgacgaggtc gtgtgacctc gccccggacc tgccctccca ccaggtgcac ccacctgcaa      660
taaacgcagc gaaggccggg aaaaaaa                                          687
```

<210> SEQ ID NO 4
<211> LENGTH: 195
<212> TYPE: PRT
<213> ORGANISM: Homo sapiens

<400> SEQUENCE: 4

```
Met Gly Gln Ile Glu Trp Ala Met Trp Ala Asn Glu Gln Ala Leu Ala
1               5                   10                  15

Ser Gly Leu Ile Leu Ile Thr Gly Gly Ile Val Ala Thr Ala Gly Arg
            20                  25                  30

Phe Thr Gln Trp Tyr Phe Gly Ala Tyr Ser Ile Val Ala Gly Val Phe
        35                  40                  45

Val Cys Leu Leu Glu Tyr Pro Arg Gly Lys Arg Lys Gly Ser Thr
    50                  55                  60

Met Glu Arg Trp Gly Gln Lys His Met Thr Ala Val Val Lys Leu Phe
65                  70                  75                  80

Gly Pro Phe Thr Arg Asn Tyr Tyr Val Arg Ala Val Leu His Leu Leu
                85                  90                  95

Leu Ser Val Pro Ala Gly Phe Leu Leu Ala Thr Ile Leu Gly Thr Ala
            100                 105                 110

Cys Leu Ala Ile Ala Ser Gly Ile Tyr Leu Leu Ala Ala Val Arg Gly
        115                 120                 125

Glu Gln Trp Thr Pro Ile Glu Pro Lys Pro Arg Glu Arg Pro Gln Ile
    130                 135                 140

Gly Gly Thr Ile Lys Gln Pro Pro Ser Asn Pro Pro Arg Pro Pro
145                 150                 155                 160

Ala Glu Ala Arg Lys Lys Pro Ser Glu Glu Ala Ala Ala Ala
                165                 170                 175

Gly Gly Pro Pro Gly Gly Pro Gln Val Asn Pro Ile Pro Val Thr Asp
            180                 185                 190

Glu Val Val
        195
```

<210> SEQ ID NO 5
<211> LENGTH: 2044
<212> TYPE: DNA
<213> ORGANISM: Homo sapiens

<400> SEQUENCE: 5

```
caaagacaaa ataatttact agggaagccc ttactaacga cccaacatcc agacacaggt       60
gagggagaag aaatttcctg acagccgaag agcaacaagt atcatgatgg ggtgctggat      120
tttgaatgag ggtctctcca ccatattagt actctcatgg ctgggaataa atttttatct      180
gtttattgac acgttctact ggtatgaaga ggaggagtct ttccattaca cacgagttat      240
tttgggttca acactggctt gggcacgagc atccgcactg tgcctgaatt ttaactgcat      300
gctaattcta atacctgtca gtcgaaacct tatttcattc ataagaggaa caagtatttg      360
```

-continued

```
ctgcagagga ccgtggagga ggcaattaga caaaaacctc agatttcaca aactggtcgc    420
ctatgggata gctgttaatg caaccatcca catcgtggcg catttcttca acctggaacg    480
ctaccactgg agccagtccg aggaggccca gggacttctg ccgcactttt ccaagctggg    540
caacacccct aacgagagct acctcaaccc tgtccggacc ttccccacaa acacaaccac    600
tgaattgcta aggacaatag caggcgtcac cggtctggtg atctctctgg ctttagtctt    660
gatcatgacc tcgtcaactg agttcatcag acaggcctcc tatgagttgt tctggtacac    720
acaccatgtt ttcatcgtct tctttctcag cctggccatc catgggacgg tcggattgt     780
tcgaggccaa acccaagaca gtctctctct gcacaacatc accttctgta gagaccgcta    840
tgcagaatgg cagacagtgg cccaatgccc cgtgcctcaa ttttctggca aggaaccctc    900
ggcttggaaa tggattttag gccctgtggt cttgtatgca tgtgaaagaa taattaggtt    960
ctggcgattt caacaagaag ttgtcattac caaggtggta agccaccct ctggagtcct    1020
ggaacttcac atgaaaaagc gtggctttaa atggcgccca gggcagtaca tcttggtgca   1080
gtgcccagcc atatcttcgc tggagtggca ccccttcacc cttacctctg ccccccagga   1140
agactttttc agcgtgcaca tccgggcagc aggagactgg acagcagcgc tactggaggc   1200
ctttggggca gagggacagg ccctccagga gccctggagc ctgccaaggc tggcagtgga   1260
cgggcccttt ggaactgccc tgacagatgt atttcactac ccagtgtgtg tgtgcgttgc   1320
cgcggggatc ggagtcactc ccttcgctgc tcttctgaaa tctatatggt acaaatgcag   1380
tgaggcacag accccactga agctgagcaa ggtgtatttc tactggattt gccgggatgc   1440
aagagctttt gagtggtttg ctgatctctt actctccctg gaaacacgga tgagtgagca   1500
ggggaaaact cactttctga gttatcatat atttcttacc ggctgggatg aaaatcaggc   1560
tcttcacata gctttacact gggacgaaaa tactgacgtg attacaggct aaagcagaa    1620
gaccttctat ggggaggccca actgaacaa tgagttcaag cagattgcct acaatcaccc   1680
cagcagcagt attggcgtgt cttctgtgg acctaaagct ctctcgagga cacttcaaaa   1740
gatgtgccac ttgtattcat cagctgaccc cagaggtgtt catttctatt acaacaagga   1800
gagcttctag actttggagg tcaagtccag gcattgtgtt tcaatcaag ttattgattc    1860
caaagaactc caccaggaat tcctgtgacg gcctgttgat atgagctccc agttgggaac   1920
tggtgaataa taattaacta ttgtgaacag tacactatac catacttcct tagcttataa   1980
ataacatgtc atatacaaca gaacaaaaac atttactgaa attaaaatat attatgtttc   2040
tcca                                                               2044
```

<210> SEQ ID NO 6
<211> LENGTH: 568
<212> TYPE: PRT
<213> ORGANISM: Homo sapiens

<400> SEQUENCE: 6

Met Met Gly Cys Trp Ile Leu Asn Glu Gly Leu Ser Thr Ile Leu Val
1               5                   10                  15

Leu Ser Trp Leu Gly Ile Asn Phe Tyr Leu Phe Ile Asp Thr Phe Tyr
            20                  25                  30

Trp Tyr Glu Glu Glu Glu Ser Phe His Tyr Thr Arg Val Ile Leu Gly
        35                  40                  45

Ser Thr Leu Ala Trp Ala Arg Ala Ser Ala Leu Cys Leu Asn Phe Asn
    50                  55                  60

-continued

```
Cys Met Leu Ile Leu Ile Pro Val Ser Arg Asn Leu Ile Ser Phe Ile
 65                  70                  75                  80

Arg Gly Thr Ser Ile Cys Cys Arg Gly Pro Trp Arg Arg Gln Leu Asp
                 85                  90                  95

Lys Asn Leu Arg Phe His Lys Leu Val Ala Tyr Gly Ile Ala Val Asn
            100                 105                 110

Ala Thr Ile His Ile Val Ala His Phe Phe Asn Leu Glu Arg Tyr His
        115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
                180                 185                 190

Glu Phe Ile Arg Gln Ala Ser Tyr Glu Leu Phe Trp Tyr Thr His His
            195                 200                 205

Val Phe Ile Val Phe Phe Leu Ser Leu Ala Ile His Gly Thr Gly Arg
210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
            260                 265                 270

Gly Pro Val Val Leu Tyr Ala Cys Glu Arg Ile Ile Arg Phe Trp Arg
        275                 280                 285

Phe Gln Gln Glu Val Val Ile Thr Lys Val Val Ser His Pro Ser Gly
    290                 295                 300

Val Leu Glu Leu His Met Lys Lys Arg Gly Phe Lys Met Ala Pro Gly
305                 310                 315                 320

Gln Tyr Ile Leu Val Gln Cys Pro Ala Ile Ser Ser Leu Glu Trp His
                325                 330                 335

Pro Phe Thr Leu Thr Ser Ala Pro Gln Glu Asp Phe Phe Ser Val His
            340                 345                 350

Ile Arg Ala Ala Gly Asp Trp Thr Ala Leu Leu Glu Ala Phe Gly
        355                 360                 365

Ala Glu Gly Gln Ala Leu Gln Glu Pro Trp Ser Leu Pro Arg Leu Ala
    370                 375                 380

Val Asp Gly Pro Phe Gly Thr Ala Leu Thr Asp Val Phe His Tyr Pro
385                 390                 395                 400

Val Cys Val Cys Val Ala Ala Gly Ile Gly Val Thr Pro Phe Ala Ala
                405                 410                 415

Leu Leu Lys Ser Ile Trp Tyr Lys Cys Ser Glu Ala Gln Thr Pro Leu
            420                 425                 430

Lys Leu Ser Lys Val Tyr Phe Tyr Trp Ile Cys Arg Asp Ala Arg Ala
        435                 440                 445

Phe Glu Trp Phe Ala Asp Leu Leu Ser Leu Glu Thr Arg Met Ser
    450                 455                 460

Glu Gln Gly Lys Thr His Phe Leu Ser Tyr His Ile Phe Leu Thr Gly
465                 470                 475                 480
```

-continued

```
Trp Asp Glu Asn Gln Ala Leu His Ile Ala Leu His Trp Asp Glu Asn
            485                 490                 495

Thr Asp Val Ile Thr Gly Leu Lys Gln Lys Thr Phe Tyr Gly Arg Pro
        500                 505                 510

Asn Trp Asn Asn Glu Phe Lys Gln Ile Ala Tyr Asn His Pro Ser Ser
        515                 520                 525

Ser Ile Gly Val Phe Cys Gly Pro Lys Ala Leu Ser Arg Thr Leu
    530                 535                 540

Gln Lys Met Cys His Leu Tyr Ser Ser Ala Asp Pro Arg Gly Val His
545                 550                 555                 560

Phe Tyr Tyr Asn Lys Glu Ser Phe
                565

<210> SEQ ID NO 7
<211> LENGTH: 2232
<212> TYPE: DNA
<213> ORGANISM: Homo sapiens

<400> SEQUENCE: 7
ccgcacaact gtaaccgctg ccccggccgc cgcccgctcc ttctcgggcc ggcgggcaca      60
gagcgcagcg cggcggggcc ggcggcatgg ctgtgtcctg gaggagctgg ctcgccaacg     120
aaggggttaa acacctctgc ctgttcatct ggctctccat gaatgtcctg cttttctgga     180 aaccttctt gctgtataac aagggccag agtatcacta cctccaccag atgttggggc      240
taggattgtg tctaagcaga gcctcagcat ctgttcttaa cctcaactgc agccttatcc     300
ttttacccat gtgccgaaca ctcttggctt acctccgagg atcacagaag gttccaagca     360
ggagaaccag gagattgttg gataaaagca gaacattcca tattacctgt ggtgttacta     420
tctgtatttt ctcaggcgtg catgtggctg cccatctggt gaatgccctc aacttctcag     480
tgaattacag tgaagacttt gttgaactga atgcagcaag ataccgagat gaggatccta     540
gaaaacttct cttcacaact gttcctggcc tgacagggt ctgcatggtg gtggtgctat      600
tcctcatgat cacagcctct acatatgcaa taagagtttc taactatgat atcttctggt     660
atactcataa cctcttcttt gtcttctaca tgctgctgac gttgcatgtt tcaggagggc     720
tgctgaagta tcaaactaat ttagataccc accctcccgg ctgcatcagt cttaaccgaa     780
ccagctctca gaatatttcc ttaccagagt atttctcaga cattttcat gaacctttcc      840 ctgaaggatt tcaaaaccg gcagagttta cccagcacaa atttgtgaag atttgtatgg      900
aagagcccag attccaagct aattttccac agacttggct ttggatttct ggacctttgt     960
gcctgtactg tgccgaaaga ctttacaggt atatccggag caataagcca gtcaccatca    1020
tttcggtcat aagtcatccc tcagatgtca tggaaatccg aatggtcaaa gaaaatttta    1080 agcaagacc tggtcagtat attactctac attgtccag tgtatctgca ttagaaaatc     1140
atccatttac cctcacaatg tgtccaactg aaaccaaagc aacatttggg gttcatctta    1200
aaatagtagg agactggaca gaacgatttc gagatttact actgcctcca tctagtcaag    1260
actccgaaat tctgcccttc attcaatcta gaattatcc caagctgtat attgatggtc    1320
cttttggaag tccatttgag gaatcactga actatgaggt cagcctctgc gtggctggag    1380
gcattggagt aactccattt gcatcaatac tcaacaccct gttggatgac tggaaaccat    1440
acaagcttag aagactatac tttatttggg tatgcagaga tatccagtcc ttccgttggt    1500
ttgcagattt actctgtatg ttgcataaca agtttggca agagaacaga cctgactatg     1560
tcaacatcca gctgtaccct agtcaaacag atgggataca aagataatt ggagaaaaat     1620
```

-continued

```
atcatgcact gaattcaaga ctgtttatag gacgtcctcg gtggaaactt ttgtttgatg    1680
aaatagcaaa atataacaga ggaaaaacag ttggtgtttt ctgttgtgga cccaattcac    1740
tatccaagac tcttcataaa ctgagtaacc agaacaactc atatgggaca agatttgaat    1800
acaataaaga gtctttcagc tgaaaacttt tgccatgaag caggactcta aagaaggaat    1860
gagtgcaatt tctaagactt tgaaactcag cggaatcaat cagctgtgtt atgccaaaga    1920
atagtaaggt tttcttattt atgattattt gaaaatggaa atgtgagaat gtggcaacat    1980
gaccgtcaca ttacatgttt aatctggaaa ccaagagac cctgaagaat atttgatgtg    2040
atgattcatt ttcagttctc aaattaaaag aaaactgtta gatgcacact gttgattttc    2100
atggtggatt caagaactcc ctagtgagga gctgaacttg ctcaatctaa ggctgattgt    2160
cgtgttcctc tttaaattgt ttttggttga acaaatgcaa gattgaacaa aattaaaaat    2220
tcattgaagc tg                                                       2232
```

<210> SEQ ID NO 8
<211> LENGTH: 578
<212> TYPE: PRT
<213> ORGANISM: Homo sapiens

<400> SEQUENCE: 8

```
Met Ala Val Ser Trp Arg Ser Trp Leu Ala Asn Glu Gly Val Lys His
1               5                   10                  15

Leu Cys Leu Phe Ile Trp Leu Ser Met Asn Val Leu Phe Trp Lys
                20                  25                  30

Thr Phe Leu Leu Tyr Asn Gln Gly Pro Glu Tyr His Tyr Leu His Gln
            35                  40                  45

Met Leu Gly Leu Gly Leu Cys Leu Ser Arg Ala Ser Ala Ser Val Leu
        50                  55                  60

Asn Leu Asn Cys Ser Leu Ile Leu Pro Met Cys Arg Thr Leu Leu
65                  70                  75                  80

Ala Tyr Leu Arg Gly Ser Gln Lys Val Pro Ser Arg Arg Thr Arg Arg
                85                  90                  95

Leu Leu Asp Lys Ser Arg Thr Phe His Ile Thr Cys Gly Val Thr Ile
            100                 105                 110

Cys Ile Phe Ser Gly Val His Val Ala Ala His Leu Val Asn Ala Leu
        115                 120                 125

Asn Phe Ser Val Asn Tyr Ser Glu Asp Phe Val Glu Leu Asn Ala Ala
    130                 135                 140

Arg Tyr Arg Asp Glu Asp Pro Arg Lys Leu Leu Phe Thr Thr Val Pro
145                 150                 155                 160

Gly Leu Thr Gly Val Cys Met Val Val Leu Phe Leu Met Ile Thr
                165                 170                 175

Ala Ser Thr Tyr Ala Ile Arg Val Ser Asn Tyr Asp Ile Phe Trp Tyr
            180                 185                 190

Thr His Asn Leu Phe Phe Val Phe Tyr Met Leu Leu Thr Leu His Val
        195                 200                 205

Ser Gly Gly Leu Leu Lys Tyr Gln Thr Asn Leu Asp Thr His Pro Pro
    210                 215                 220

Gly Cys Ile Ser Leu Asn Arg Thr Ser Ser Gln Asn Ile Ser Leu Pro
225                 230                 235                 240

Glu Tyr Phe Ser Glu His Phe His Glu Pro Phe Pro Glu Gly Phe Ser
                245                 250                 255
```

```
Lys Pro Ala Glu Phe Thr Gln His Lys Phe Val Lys Ile Cys Met Glu
            260                 265                 270

Glu Pro Arg Phe Gln Ala Asn Phe Pro Gln Thr Trp Leu Trp Ile Ser
        275                 280                 285

Gly Pro Leu Cys Leu Tyr Cys Ala Glu Arg Leu Tyr Arg Tyr Ile Arg
    290                 295                 300

Ser Asn Lys Pro Val Thr Ile Ile Ser Val Ile Ser His Pro Ser Asp
305                 310                 315                 320

Val Met Glu Ile Arg Met Val Lys Glu Asn Phe Lys Ala Arg Pro Gly
                325                 330                 335

Gln Tyr Ile Thr Leu His Cys Pro Ser Val Ser Ala Leu Glu Asn His
            340                 345                 350

Pro Phe Thr Leu Thr Met Cys Pro Thr Glu Thr Lys Ala Thr Phe Gly
        355                 360                 365

Val His Leu Lys Ile Val Gly Asp Trp Thr Glu Arg Phe Arg Asp Leu
    370                 375                 380

Leu Leu Pro Pro Ser Ser Gln Asp Ser Glu Ile Leu Pro Phe Ile Gln
385                 390                 395                 400

Ser Arg Asn Tyr Pro Lys Leu Tyr Ile Asp Gly Pro Phe Gly Ser Pro
                405                 410                 415

Phe Glu Glu Ser Leu Asn Tyr Glu Val Ser Leu Cys Val Ala Gly Gly
            420                 425                 430

Ile Gly Val Thr Pro Phe Ala Ser Ile Leu Asn Thr Leu Leu Asp Asp
        435                 440                 445

Trp Lys Pro Tyr Lys Leu Arg Arg Leu Tyr Phe Ile Trp Val Cys Arg
    450                 455                 460

Asp Ile Gln Ser Phe Arg Trp Phe Ala Asp Leu Leu Cys Met Leu His
465                 470                 475                 480

Asn Lys Phe Trp Gln Glu Asn Arg Pro Asp Tyr Val Asn Ile Gln Leu
                485                 490                 495

Tyr Leu Ser Gln Thr Asp Gly Ile Gln Lys Ile Ile Gly Glu Lys Tyr
            500                 505                 510

His Ala Leu Asn Ser Arg Leu Phe Ile Gly Arg Pro Arg Trp Lys Leu
        515                 520                 525

Leu Phe Asp Glu Ile Ala Lys Tyr Asn Arg Gly Lys Thr Val Gly Val
    530                 535                 540

Phe Cys Cys Gly Pro Asn Ser Leu Ser Lys Thr Leu His Lys Leu Ser
545                 550                 555                 560

Asn Gln Asn Asn Ser Tyr Gly Thr Arg Phe Glu Tyr Asn Lys Glu Ser
                565                 570                 575

Phe Ser
```

<210> SEQ ID NO 9
<211> LENGTH: 2223
<212> TYPE: DNA
<213> ORGANISM: Homo sapiens

<400> SEQUENCE: 9

```
gccgacgcgg acggcaacgg ggccatcacc ttcgaggagc tccgggacga gctgcagcgc    60
ttccccggag tcatggagaa cctgaccatc agcactgccc actggctgac ggccccgcc   120 ccccgcccac gcccgcgccg ccgcgccag ctgacccgcg cctactggca caaccaccgc   180
agccagctgt tctgcctggc cacctatgca ggcctccacg tgctgctctt cgggctggcg   240
gccagcgcgc accgggacct cggcgccagc gtcatggtgg ccaagggctg tggccagtgc   300
```

```
ctcaacttcg actgcagctt catcgcggtg ctgatgctca gacgctgcct cacctggctg    360
cgggccacgt ggctggctca agtcctacca ctggaccaga acatccagtt ccaccagctt    420
atgggctacg tggtagtggg gctgtccctc gtgcacactg tggctcacac tgtgaacttt    480
gtactccagg ctcaggcgga ggccagccct tccagttct gggagctgct gctcaccacg     540
aggcctggca ttggctgggt acacggttcg gcctccccga caggtgtcgc tctgctgctg    600
ctgctcctcc tcatgttcat ctgctccagt cctgcatcc gcaggagtgg ccactttgag     660
gtgttctatt ggactcacct gtcctacctc ctcgtgtggc ttctgctcat ctttcatggg    720
cccaacttct ggaagtggct gctggtgcct ggaatcttgt ttttcctgga aaggccatc    780
ggactggcag tgtcccgcat ggcagccgtg tgcatcatgg aagtcaacct cctcccctcc    840
aaggtcactc atctcctcat caagcggccc ccttttttc actatagacc tggtgactac    900
ttgtatctga acatccccac cattgctcgc tatgagtggc accccttcac catcagcagt    960
gctcctgagc agaaagacac tatctggctg cacattcggt cccaaggcca gtggacaaac   1020
aggctgtatg agtccttcaa ggcatcagac ccactgggcc gtggttctaa gaggctgtcg   1080
aggagtgtga caatgagaaa gagtcaaagg tcgtccaagg gctctgagat acttttggag   1140
aaacacaaat tctgtaacat caagtgctac atcgatgggc cttatgggac ccccacccgc   1200
aggatctttg cctctgagca tgccgtgctc atcggggcag gcatcggcat caccccctt    1260
gcttccattc tgcagagtat catgtacagg caccagaaaa gaaagcatac ttgccccagc   1320
tgccagcact cctggatcga aggtgtccaa gacaacatga agctccataa ggtggacttt   1380
atctggatca acagagacca gcggtctttc gagtggtttg tgagcctgct gactaaactg   1440
gagatggacc aggccgagga ggctcaatac ggccgcttcc tggagctgca tatgtacatg   1500
acatctgcac tgggcaagaa tgacatgaag gccattggcc tgcagatggc ccttgacctc   1560
ctggccaaca aggagaagaa agactccatc acggggctgc agacgcgcac ccagcctggg   1620
cggcctgact ggagcaaggt gttccagaaa gtggctgctg agaagaaggg caaggtgcag   1680
gtcttcttct gtggctcccc agctctggcc aaggtgctga aggccattg tgagaagttc   1740
ggcttcagat ttttccaaga gaatttctag cctcacctct ccaagtctg ccccaagtcc    1800
acaccatggg tctgcttcat cgcattagta taaatgcccc cacagggacc agcctcagat   1860
gacccaccca ataagacaaa gcctagggac cccctaatcc tgctcaacag agagaacagg   1920
agacccaag gggcagatga acttcctcta gaacccaggg gaaggggcag tgccttgttc    1980
agtctgctgt agattctggg gtttctgtga aagtgaggga accagaggct ggtcacggga   2040
gcttgggggt ggggttcgag ggggcagagg gcaaccactc ctccaaacat tttccgacgg   2100
agccttcccc cacatccatg gtcccaaacc tgccaatca tcacagtcat ttggaagctt    2160
atttctccgg catcttataa aattgttcaa acctacagta aaaaaaaaa aaaaaaaaa     2220
aaa                                                                 2223
```

<210> SEQ ID NO 10
<211> LENGTH: 565
<212> TYPE: PRT
<213> ORGANISM: Homo sapiens

<400> SEQUENCE: 10

Met Glu Asn Leu Thr Ile Ser Thr Ala His Trp Leu Thr Ala Pro Ala
1               5                   10                  15

Pro Arg Pro Arg Pro Arg Pro Arg Gln Leu Thr Arg Ala Tyr Trp
            20                  25                  30

```
His Asn His Arg Ser Gln Leu Phe Cys Leu Ala Thr Tyr Ala Gly Leu
        35                  40                  45

His Val Leu Leu Phe Gly Leu Ala Ala Ser Ala His Arg Asp Leu Gly
    50                  55                  60

Ala Ser Val Met Val Ala Lys Gly Cys Gly Gln Cys Leu Asn Phe Asp
65                  70                  75                  80

Cys Ser Phe Ile Ala Val Leu Met Leu Arg Arg Cys Leu Thr Trp Leu
                85                  90                  95

Arg Ala Thr Trp Leu Ala Gln Val Leu Pro Leu Asp Gln Asn Ile Gln
                100                 105                 110

Phe His Gln Leu Met Gly Tyr Val Val Gly Leu Ser Leu Val His
        115                 120                 125

Thr Val Ala His Thr Val Asn Phe Val Leu Gln Ala Gln Ala Glu Ala
    130                 135                 140

Ser Pro Phe Gln Phe Trp Glu Leu Leu Leu Thr Thr Arg Pro Gly Ile
145                 150                 155                 160

Gly Trp Val His Gly Ser Ala Ser Pro Thr Gly Val Ala Leu Leu Leu
                165                 170                 175

Leu Leu Leu Leu Met Phe Ile Cys Ser Ser Cys Ile Arg Arg Ser
                180                 185                 190

Gly His Phe Glu Val Phe Tyr Trp Thr His Leu Ser Tyr Leu Leu Val
        195                 200                 205

Trp Leu Leu Leu Ile Phe His Gly Pro Asn Phe Trp Lys Trp Leu Leu
        210                 215                 220

Val Pro Gly Ile Leu Phe Phe Leu Glu Lys Ala Ile Gly Leu Ala Val
225                 230                 235                 240

Ser Arg Met Ala Ala Val Cys Ile Met Glu Val Asn Leu Leu Pro Ser
                245                 250                 255

Lys Val Thr His Leu Leu Ile Lys Arg Pro Pro Phe Phe His Tyr Arg
                260                 265                 270

Pro Gly Asp Tyr Leu Tyr Leu Asn Ile Pro Thr Ile Ala Arg Tyr Glu
        275                 280                 285

Trp His Pro Phe Thr Ile Ser Ser Ala Pro Glu Gln Lys Asp Thr Ile
        290                 295                 300

Trp Leu His Ile Arg Ser Gln Gly Gln Trp Thr Asn Arg Leu Tyr Glu
305                 310                 315                 320

Ser Phe Lys Ala Ser Asp Pro Leu Gly Arg Gly Ser Lys Arg Leu Ser
                325                 330                 335

Arg Ser Val Thr Met Arg Lys Ser Gln Arg Ser Ser Lys Gly Ser Glu
                340                 345                 350

Ile Leu Leu Glu Lys His Lys Phe Cys Asn Ile Lys Cys Tyr Ile Asp
                355                 360                 365

Gly Pro Tyr Gly Thr Pro Thr Arg Arg Ile Phe Ala Ser Glu His Ala
        370                 375                 380

Val Leu Ile Gly Ala Gly Ile Gly Ile Thr Pro Phe Ala Ser Ile Leu
385                 390                 395                 400

Gln Ser Ile Met Tyr Arg His Gln Lys Arg Lys His Thr Cys Pro Ser
                405                 410                 415

Cys Gln His Ser Trp Ile Glu Gly Val Gln Asp Asn Met Lys Leu His
                420                 425                 430

Lys Val Asp Phe Ile Trp Ile Asn Arg Asp Gln Arg Ser Phe Glu Trp
                435                 440                 445
```

-continued

```
Phe Val Ser Leu Leu Thr Lys Leu Glu Met Asp Gln Ala Glu Glu Ala
    450                 455                 460
Gln Tyr Gly Arg Phe Leu Glu Leu His Met Tyr Met Thr Ser Ala Leu
465                 470                 475                 480
Gly Lys Asn Asp Met Lys Ala Ile Gly Leu Gln Met Ala Leu Asp Leu
                485                 490                 495
Leu Ala Asn Lys Glu Lys Lys Asp Ser Ile Thr Gly Leu Gln Thr Arg
            500                 505                 510
Thr Gln Pro Gly Arg Pro Asp Trp Ser Lys Val Phe Gln Lys Val Ala
        515                 520                 525
Ala Glu Lys Lys Gly Lys Val Gln Val Phe Phe Cys Gly Ser Pro Ala
    530                 535                 540
Leu Ala Lys Val Leu Lys Gly His Cys Glu Lys Phe Gly Phe Arg Phe
545                 550                 555                 560
Phe Gln Glu Asn Phe
                565

<210> SEQ ID NO 11
<211> LENGTH: 5494
<212> TYPE: DNA
<213> ORGANISM: Homo sapiens

<400> SEQUENCE: 11
```

| | | | | | |
|---|---|---|---|---|---|
| gcagagctgc | agaggcaccg | gacgagagag | ggctccgcgg | gcccagctgg | cagccaggcc | 60 |
| ggagacaagt | tgcagtcccg | ggctctggtg | acgccgtggc | cgcagggtct | ccattttggg | 120 |
| acattctaat | ccctgagccc | ctattatttt | catcatgggc | ttctgcctgg | ctctagcatg | 180 |
| gacacttctg | gttggggcat | ggaccccctct | gggagctcag | aacccatttt | cgtgggaggt | 240 |
| gcagcgattt | gatgggtggt | acaacaacct | catggagcac | agatggggca | gcaaaggctc | 300 |
| ccggctgcag | cgcctggtcc | cagccagcta | tgcagatggc | gtgtaccagc | ccttgggaga | 360 |
| accccacctg | cccaaccccc | gagaccttag | caacaccatc | tcaaggggcc | ctgcagggct | 420 |
| ggcctccctg | agaaaccgca | cagtgttggg | ggtcttcttt | ggctatcacg | tgctttcaga | 480 |
| cctggtgagc | gtggaaactc | ccggctgccc | cgccgagttc | ctcaacattc | gcatcccgcc | 540 |
| cggagacccc | atgttcgacc | ccgaccagcc | cggggacgtg | gtgctgcctt | tccagagaag | 600 |
| ccgctgggac | cccgagaccg | gacggagtcc | cagcaatccc | cgggacccgg | ccaaccaggt | 660 |
| gacgggctgg | ctggacggca | cgccatctta | tggttcctcg | cattcctgga | gcgacgcgct | 720 |
| gcggagcttc | tccaggggac | agctggcgtc | ggggcccgac | cccgcttttc | cccgagactc | 780 |
| gcagaacccc | ctgctcatgt | gggcggcgcc | cgaccccgcc | accgggcaga | acgggcccccg | 840 |
| ggggctgtac | gccttcgggg | cagagagagg | gaaccgggaa | cccttcctgc | aggcgctggg | 900 |
| cctgctctgg | ttccgctacc | acaacctgtg | ggcgcagagg | ctggcccgcc | agcacccaga | 960 |
| ctgggaggac | gaggagctgt | tccagcacgc | acgcaagagg | gtcatcgcca | cctaccagaa | 1020 |
| catcgctgtg | tatgagtggc | tgcccagctt | cctgcagaaa | acactcccgg | agtatacagg | 1080 |
| ataccggcca | tttctggacc | ccagcatctc | ctcagagttc | gtggcggcct | ctgagcagtt | 1140 |
| cctgtccacc | atggtgcccc | ctggcgtcta | catgagaaat | gccagctgcc | acttccaggg | 1200 |
| ggtcatcaat | cggaactcaa | gtgtctccag | agctctccgg | gtctgcaaca | gctactggag | 1260 |
| ccgtgagcac | ccaagcctac | aaagtgctga | agatgtggat | gcactgctgc | tgggcatggc | 1320 |
| ctcccagatc | gcagagcgag | aggaccatgt | gttggttgaa | gatgtgcggg | atttctggcc | 1380 |
| tgggccactg | aagttttccc | gcacagacca | cctggccagc | tgcctgcagc | ggggccggga | 1440 |

-continued

```
tctgggcctg ccctcttaca ccaaggccag ggcagcactg ggcttgtctc ccattacccg   1500
ctggcaggac atcaaccctg cactctcccg gagcaatgac actgtactgg aggccacagc   1560
tgccctgtac aaccaggact tatcctggct agagctgctc cctgggggac tcctggagag   1620
ccaccgggac cctggacctc tgttcagcac catcgtcctt gaacaatttg tgcggctacg   1680
ggatggtgac cgctactggt ttgagaacac caggaatggg ctgttctcca agaaggagat   1740
tgaagaaatc cgaaatacca ccctgcagga cgtgctggtc gctgttatca acattgaccc   1800
cagtgctctg cagcccaatg tctttgtctg gcataaagga gaccctgtc cgcagccgag   1860 acagctcagc actgaaggcc tgccagcgtg tgctccctct gttgttcgtg actattttga   1920
gggcagtgga tttggcttcg gggtcaccat cgggaccctc tgttgcttcc ctttggtgag   1980
cctgctcagt gcctggattg ttgcccggct ccggatgaga aatttcaaga ggctccaggg   2040
ccaggaccgc cagagcatcg tgtctgagaa gctcgtggga ggcatggaag ctttggaatg   2100
gcaaggccac aaggagccct gccggcccgt gcttgtgtac ctgcagcccg ggcagatccg   2160
tgtggtagat ggcaggctca ccgtgctccg caccatccag ctgcagcctc acagaaggt   2220 caacttcgtc ctgtccagca accgtggacg ccgcactctg ctgctcaaga tccccaagga   2280
gtatgacctg gtgctgctgt ttaacttgga ggaagagcgg caggcgctgg tggaaaatct   2340
ccggggagct ctgaaggaga gcgggttgag catccaggag tgggagctgc gggagcagga   2400
gctgatgaga gcagctgtga cacgggagca gcggaggcac ctcctggaga ccttttttcag   2460 gcacctttc tcccaggtgc tggacatcaa ccaggccgac gcagggaccc tgcccctgga   2520
ctcctcccag aaggtgcggg aggccctgac ctgtgagctg agcagggccg agtttgccga   2580
gtccctgggc ctcaagcccc aggacatgtt tgtggagtcc atgttctctc tggctgacaa   2640
ggatggcaat ggctacctgt ccttccgaga gttcctggac atcctggtgg tcttcatgaa   2700
aggctctcct gaggaaaagt ctcgcctat gttccgcatg tacgactttg atgggaatgg   2760 cctcattcc aaggatgagt tcatcaggat gctgagatcc ttcatcgaga tctccaacaa   2820
ctgcctgtcc aaggcccagc tggctgaggt ggtggagtcc atgttccggg agtcgggatt   2880
ccaggacaag gaggaactga catgggaaga ttttcacttc atgctgcggg accacaatag   2940
cgagctccgc ttcacgcagc tctgtgtcaa aggggtggag gtgcctgaag tcatcaagga   3000
cctctgccgg cgagcctcct acatcagcca ggatatgatc tgtccctctc ccagagtgag   3060
tgcccgctgt tcccgcagcg acattgagac tgagttgaca cctcagagac tgcagtgccc   3120
catggacaca gaccctcccc aggagattcg gcggaggttt ggcaagaagg taacgtcatt   3180
ccagcccttg ctgttcactg aggcgcaccg agagaagttc caacgcagct gtctccacca   3240
gacggtgcaa cagttcaagc gcttcattga gaactaccgg cgccacatcg gctgcgtggc   3300
cgtgttctac gccatcgctg gggggctttt cctggagagg gcctactact acgcctttgc   3360
cgcacatcac acgggcatca cggacaccac ccgcgtggga atcatcctgt cgcggggcac   3420
agcagccagc atctctttca tgttctccta catcttgctc accatgtgcc gcaacctcat   3480
caccttcctg cgagaaacct tcctcaaccg ctacgtgccc ttcgacgccg ccgtggactt   3540
ccatcgcctc attgcctcca ccgccatcgt cctcacagtc ttacacagtg tgggccatgt   3600
ggtgaatgtg tacctgttct ccatcagccc cctcagcgtc ctctcttgcc tctttcctgg   3660
cctcttccat gatgatgggt ctgagttccc ccagaagtat tactggtggt cttccagac   3720 cgtaccaggc ctcacggggg ttgtgctgct cctgatcctg gccatcatgt atgtctttgc   3780
ctcccaccac ttccgccgcc gcagtttccg gggcttctgg ctgacccacc acctctacat   3840
```

-continued

```
cctgctctat gtcctgctca tcatccatgg tagctttgcc ctgatccagc tgccccgttt    3900
ccacatcttc ttcctggtcc cagcaatcat ctatgggggc acaagctgg tgagcctgag     3960
ccggaagaag gtggagatca gcgtggtgaa ggcggagctg ctgccctcag gagtgaccca    4020
cctgcggttc cagcggcccc agggctttga gtacaagtca gggcagtggg tgcggatcgc    4080
ttgcctggct ctggggacca ccgagtacca ccccttcaca ctgacctctg cgccccatga    4140
ggacacgctt agcctgcaca tccgggcagc agggccctgg accactcgcc tcagggagat    4200
ctactcagcc ccgacggggtg acagatgtgc cagatacccca aagctgtacc ttgatggacc   4260
atttggagag ggccaccagg agtggcataa gtttgaggtg tcagtgttag tgggagggggg   4320
cattggggtc accccttttg cctccatcct caaagacctg gtcttcaagt catccgtcag    4380
ctgccaagtg ttctgtaaga agatctactt catctgggtg acgcggaccc agcgtcagtt    4440
tgagtggctg gctgacatca tccgagaggt ggaggagaat gaccaccagg acctggtgtc    4500
tgtgcacatc tacatcaccc agctggctga gaagttcgac ctcaggacca ctatgctgta    4560
catctgtgag cggcacttcc agaaggttct gaaccggagt ctattcacag gcctgcgctc    4620
catcacccac tttggccgtc ccccctttga gcccttcttc aactcccctgc aggaggtcca   4680
cccccaggtc cggaagatcg gggtgtttag ctgtggcccc cctggcatga ccaagaatgt    4740
ggaaaaggcc tgtcagctca tcaacaggca ggaccggact cacttctccc accattatga    4800
gaacttctag gccctgccc gggggttctg cccactgtcc agttgagcag aggtttgagc     4860
ccacacctca cctctgttct tcctatttct ggctgcctca gccttctctg atttcccacc    4920
tcccaacctt gttccaggtg ccatagtca gtcaccatgt gtgggctcag ggaccccag     4980
gaccaggatg tgtctcagcc tggagaaatg gtggggggc agtgtctagg actagagtg     5040
agaagtaggg gagctactga tttggggcaa agtgaaacct ctgcttcaga cttcagaaac    5100
aaatctcaga agacaagctg acctgacaag tactatgtgt gtgcatgtct gtatgtgtgt    5160
tggggcggtg agtgtaagga tgcagtggga gcatggatgc tggcatctta gaaccctccc    5220
tactcccata cctcctcctc ttctgggctc cccactgtca gacgggctgg caaatgcctt    5280
gcaggaggta gaggctggac ccatggcaag ccatttacag aaacccactc ggcacccag    5340
tctaacacca caactaattt cacccaaggt tttaagcacg ttctttcatc agaccctggc    5400
ccaataccta tgtatgcaat gctcctcagc cctcttctcc ctgctccagt agtctccctt    5460
ccaaataaat cacttttctg ccaaaaaaaa aaaa                                5494
```

<210> SEQ ID NO 12
<211> LENGTH: 1551
<212> TYPE: PRT
<213> ORGANISM: Homo sapiens

<400> SEQUENCE: 12

```
Met Gly Phe Cys Leu Ala Leu Ala Trp Thr Leu Leu Val Gly Ala Trp
1               5                   10                  15

Thr Pro Leu Gly Ala Gln Asn Pro Ile Ser Trp Glu Val Gln Arg Phe
            20                  25                  30

Asp Gly Trp Tyr Asn Asn Leu Met Glu His Arg Trp Gly Ser Lys Gly
        35                  40                  45

Ser Arg Leu Gln Arg Leu Val Pro Ala Ser Tyr Ala Asp Gly Val Tyr
    50                  55                  60

Gln Pro Leu Gly Glu Pro His Leu Pro Asn Pro Arg Asp Leu Ser Asn
65                  70                  75                  80
```

```
Thr Ile Ser Arg Gly Pro Ala Gly Leu Ala Ser Leu Arg Asn Arg Thr
                85                  90                  95

Val Leu Gly Val Phe Gly Tyr His Val Leu Ser Asp Leu Val Ser
            100                 105                 110

Val Glu Thr Pro Gly Cys Pro Ala Glu Phe Leu Asn Ile Arg Ile Pro
        115                 120                 125

Pro Gly Asp Pro Met Phe Asp Pro Asp Gln Arg Gly Asp Val Val Leu
    130                 135                 140

Pro Phe Gln Arg Ser Arg Trp Asp Pro Glu Thr Gly Arg Ser Pro Ser
145                 150                 155                 160

Asn Pro Arg Asp Pro Ala Asn Gln Val Thr Gly Trp Leu Asp Gly Ser
                165                 170                 175

Ala Ile Tyr Gly Ser Ser His Ser Trp Ser Asp Ala Leu Arg Ser Phe
            180                 185                 190

Ser Arg Gly Gln Leu Ala Ser Gly Pro Asp Pro Ala Phe Pro Arg Asp
        195                 200                 205

Ser Gln Asn Pro Leu Leu Met Trp Ala Ala Pro Asp Pro Ala Thr Gly
    210                 215                 220

Gln Asn Gly Pro Arg Gly Leu Tyr Ala Phe Gly Ala Glu Arg Gly Asn
225                 230                 235                 240

Arg Glu Pro Phe Leu Gln Ala Leu Gly Leu Leu Trp Phe Arg Tyr His
                245                 250                 255

Asn Leu Trp Ala Gln Arg Leu Ala Arg Gln His Pro Asp Trp Glu Asp
            260                 265                 270

Glu Glu Leu Phe Gln His Ala Arg Lys Arg Val Ile Ala Thr Tyr Gln
        275                 280                 285

Asn Ile Ala Val Tyr Glu Trp Leu Pro Ser Phe Leu Gln Lys Thr Leu
    290                 295                 300

Pro Glu Tyr Thr Gly Tyr Arg Pro Phe Leu Asp Pro Ser Ile Ser Ser
305                 310                 315                 320

Glu Phe Val Ala Ala Ser Glu Gln Phe Leu Ser Thr Met Val Pro Pro
                325                 330                 335

Gly Val Tyr Met Arg Asn Ala Ser Cys His Phe Gln Gly Val Ile Asn
            340                 345                 350

Arg Asn Ser Ser Val Ser Arg Ala Leu Arg Val Cys Asn Ser Tyr Trp
        355                 360                 365

Ser Arg Glu His Pro Ser Leu Gln Ser Ala Glu Asp Val Asp Ala Leu
    370                 375                 380

Leu Leu Gly Met Ala Ser Gln Ile Ala Glu Arg Glu Asp His Val Leu
385                 390                 395                 400

Val Glu Asp Val Arg Asp Phe Trp Pro Gly Pro Leu Lys Phe Ser Arg
                405                 410                 415

Thr Asp His Leu Ala Ser Cys Leu Gln Arg Gly Arg Asp Leu Gly Leu
            420                 425                 430

Pro Ser Tyr Thr Lys Ala Arg Ala Leu Gly Leu Ser Pro Ile Thr
        435                 440                 445

Arg Trp Gln Asp Ile Asn Pro Ala Leu Ser Arg Ser Asn Asp Thr Val
    450                 455                 460

Leu Glu Ala Thr Ala Ala Leu Tyr Asn Gln Asp Leu Ser Trp Leu Glu
465                 470                 475                 480

Leu Leu Pro Gly Gly Leu Leu Glu Ser His Arg Asp Pro Gly Pro Leu
                485                 490                 495
```

-continued

```
Phe Ser Thr Ile Val Leu Glu Gln Phe Val Arg Leu Arg Asp Gly Asp
            500                 505                 510

Arg Tyr Trp Phe Glu Asn Thr Arg Asn Gly Leu Phe Ser Lys Lys Glu
            515                 520                 525

Ile Glu Glu Ile Arg Asn Thr Thr Leu Gln Asp Val Leu Val Ala Val
            530                 535                 540

Ile Asn Ile Asp Pro Ser Ala Leu Gln Pro Asn Val Phe Val Trp His
545                 550                 555                 560

Lys Gly Asp Pro Cys Pro Gln Pro Arg Gln Leu Ser Thr Glu Gly Leu
                565                 570                 575

Pro Ala Cys Ala Pro Ser Val Val Arg Asp Tyr Phe Glu Gly Ser Gly
                580                 585                 590

Phe Gly Phe Gly Val Thr Ile Gly Thr Leu Cys Cys Phe Pro Leu Val
            595                 600                 605

Ser Leu Leu Ser Ala Trp Ile Val Ala Arg Leu Arg Met Arg Asn Phe
            610                 615                 620

Lys Arg Leu Gln Gly Gln Asp Arg Gln Ser Ile Val Ser Glu Lys Leu
625                 630                 635                 640

Val Gly Gly Met Glu Ala Leu Glu Trp Gln Gly His Lys Glu Pro Cys
                645                 650                 655

Arg Pro Val Leu Val Tyr Leu Gln Pro Gly Gln Ile Arg Val Val Asp
                660                 665                 670

Gly Arg Leu Thr Val Leu Arg Thr Ile Gln Leu Gln Pro Pro Gln Lys
            675                 680                 685

Val Asn Phe Val Leu Ser Ser Asn Arg Gly Arg Thr Leu Leu Leu
            690                 695                 700

Lys Ile Pro Lys Glu Tyr Asp Leu Val Leu Leu Phe Asn Leu Glu Glu
705                 710                 715                 720

Glu Arg Gln Ala Leu Val Glu Asn Leu Arg Gly Ala Leu Lys Glu Ser
                725                 730                 735

Gly Leu Ser Ile Gln Glu Trp Glu Leu Arg Glu Gln Glu Leu Met Arg
            740                 745                 750

Ala Ala Val Thr Arg Glu Gln Arg Arg His Leu Leu Glu Thr Phe Phe
            755                 760                 765

Arg His Leu Phe Ser Gln Val Leu Asp Ile Asn Gln Ala Asp Ala Gly
            770                 775                 780

Thr Leu Pro Leu Asp Ser Ser Gln Lys Val Arg Glu Ala Leu Thr Cys
785                 790                 795                 800

Glu Leu Ser Arg Ala Glu Phe Ala Glu Ser Leu Gly Leu Lys Pro Gln
                805                 810                 815

Asp Met Phe Val Glu Ser Met Phe Ser Leu Ala Asp Lys Asp Gly Asn
                820                 825                 830

Gly Tyr Leu Ser Phe Arg Glu Phe Leu Asp Ile Leu Val Val Phe Met
            835                 840                 845

Lys Gly Ser Pro Glu Glu Lys Ser Arg Leu Met Phe Arg Met Tyr Asp
850                 855                 860

Phe Asp Gly Asn Gly Leu Ile Ser Lys Asp Glu Phe Ile Arg Met Leu
865                 870                 875                 880

Arg Ser Phe Ile Glu Ile Ser Asn Asn Cys Leu Ser Lys Ala Gln Leu
                885                 890                 895

Ala Glu Val Val Glu Ser Met Phe Arg Glu Ser Gly Phe Gln Asp Lys
                900                 905                 910
```

-continued

```
Glu Glu Leu Thr Trp Glu Asp Phe His Phe Met Leu Arg Asp His Asn
        915                 920                 925
Ser Glu Leu Arg Phe Thr Gln Leu Cys Val Lys Gly Val Glu Val Pro
        930                 935                 940
Glu Val Ile Lys Asp Leu Cys Arg Arg Ala Ser Tyr Ile Ser Gln Asp
945                 950                 955                 960
Met Ile Cys Pro Ser Pro Arg Val Ser Ala Arg Cys Ser Arg Ser Asp
                965                 970                 975
Ile Glu Thr Glu Leu Thr Pro Gln Arg Leu Gln Cys Pro Met Asp Thr
                980                 985                 990
Asp Pro Pro Gln Glu Ile Arg Arg Phe Gly Lys Lys Val Thr Ser
            995                 1000                1005
Phe Gln Pro Leu Leu Phe Thr Glu Ala His Arg Glu Lys Phe Gln Arg
            1010                1015                1020
Ser Cys Leu His Gln Thr Val Gln Gln Phe Lys Arg Phe Ile Glu Asn
1025                1030                1035                1040
Tyr Arg Arg His Ile Gly Cys Val Ala Val Phe Tyr Ala Ile Ala Gly
                1045                1050                1055
Gly Leu Phe Leu Glu Arg Ala Tyr Tyr Tyr Ala Phe Ala Ala His His
            1060                1065                1070
Thr Gly Ile Thr Asp Thr Thr Arg Val Gly Ile Ile Leu Ser Arg Gly
            1075                1080                1085
Thr Ala Ala Ser Ile Ser Phe Met Phe Ser Tyr Ile Leu Leu Thr Met
            1090                1095                1100
Cys Arg Asn Leu Ile Thr Phe Leu Arg Glu Thr Phe Leu Asn Arg Tyr
1105                1110                1115                1120
Val Pro Phe Asp Ala Ala Val Asp Phe His Arg Leu Ile Ala Ser Thr
                1125                1130                1135
Ala Ile Val Leu Thr Val Leu His Ser Val Gly His Val Val Asn Val
            1140                1145                1150
Tyr Leu Phe Ser Ile Ser Pro Leu Ser Val Leu Ser Cys Leu Phe Pro
            1155                1160                1165
Gly Leu Phe His Asp Asp Gly Ser Glu Phe Pro Gln Lys Tyr Tyr Trp
            1170                1175                1180
Trp Phe Phe Gln Thr Val Pro Gly Leu Thr Gly Val Val Leu Leu Leu
1185                1190                1195                1200
Ile Leu Ala Ile Met Tyr Val Phe Ala Ser His His Phe Arg Arg Arg
                1205                1210                1215
Ser Phe Arg Gly Phe Trp Leu Thr His His Leu Tyr Ile Leu Leu Tyr
            1220                1225                1230
Val Leu Leu Ile Ile His Gly Ser Phe Ala Leu Ile Gln Leu Pro Arg
            1235                1240                1245
Phe His Ile Phe Phe Leu Val Pro Ala Ile Ile Tyr Gly Gly Asp Lys
            1250                1255                1260
Leu Val Ser Leu Ser Arg Lys Lys Val Glu Ile Ser Val Val Lys Ala
1265                1270                1275                1280
Glu Leu Leu Pro Ser Gly Val Thr His Leu Arg Phe Gln Arg Pro Gln
            1285                1290                1295
Gly Phe Glu Tyr Lys Ser Gly Gln Trp Val Arg Ile Ala Cys Leu Ala
            1300                1305                1310
Leu Gly Thr Thr Glu Tyr His Pro Phe Thr Leu Thr Ser Ala Pro His
            1315                1320                1325
```

-continued

Glu Asp Thr Leu Ser Leu His Ile Arg Ala Ala Gly Pro Trp Thr Thr
    1330                1335                1340
Arg Leu Arg Glu Ile Tyr Ser Ala Pro Thr Gly Asp Arg Cys Ala Arg
1345                1350                1355                1360
Tyr Pro Lys Leu Tyr Leu Asp Gly Pro Phe Gly Glu Gly His Gln Glu
            1365                1370                1375
Trp His Lys Phe Glu Val Ser Val Leu Val Gly Gly Gly Ile Gly Val
        1380                1385                1390
Thr Pro Phe Ala Ser Ile Leu Lys Asp Leu Val Phe Lys Ser Ser Val
    1395                1400                1405
Ser Cys Gln Val Phe Cys Lys Lys Ile Tyr Phe Ile Trp Val Thr Arg
    1410                1415                1420
Thr Gln Arg Gln Phe Glu Trp Leu Ala Asp Ile Ile Arg Glu Val Glu
1425                1430                1435                1440
Glu Asn Asp His Gln Asp Leu Val Ser Val His Ile Tyr Ile Thr Gln
            1445                1450                1455
Leu Ala Glu Lys Phe Asp Leu Arg Thr Thr Met Leu Tyr Ile Cys Glu
        1460                1465                1470
Arg His Phe Gln Lys Val Leu Asn Arg Ser Leu Phe Thr Gly Leu Arg
    1475                1480                1485
Ser Ile Thr His Phe Gly Arg Pro Pro Phe Glu Pro Phe Asn Ser
    1490                1495                1500
Leu Gln Glu Val His Pro Gln Val Arg Lys Ile Gly Val Phe Ser Cys
1505                1510                1515                1520
Gly Pro Pro Gly Met Thr Lys Asn Val Glu Lys Ala Cys Gln Leu Ile
            1525                1530                1535
Asn Arg Gln Asp Arg Thr His Phe Ser His His Tyr Glu Asn Phe
        1540                1545                1550

<210> SEQ ID NO 13
<211> LENGTH: 6375
<212> TYPE: DNA
<213> ORGANISM: Homo sapiens

<400> SEQUENCE: 13

```
ggtctgtcct gagccgacac ctgcacagtg gcgagaccaa ggacccagag agaaaggtga      60
gagtgcagcc ggggaggctg aggatcggcg gagctggaag agtgagggtg aaggcaagaa     120
gtagagcaca gaagcaaaga ttttaagagg aaagaagaca tttgaaccca acaccaccct     180
aaaccacagg ctgcagggtt ggcatgctcc gtgcaagacc agaggcactg atgctcctgg     240
gagctcttct gactggatcc ctgggtccat cgggcagtca ggacgcactc tcactgccct     300
gggaagtgca gcgctatgac ggctggttta caaacctgag gcaccacgag cgtggtgctg     360
ttggctgccg gttgcagcgc gcgtaccag ccaattacgc cgacggtgtg tatcaggctc     420
tggaggagcc gcagctgccc aaccgcgcc ggctcagcaa cgcagccacg cggggcatag     480
ccggcctgcc gtcgctccac aaccgcaccg tactgggggt cttctttggc taccatgttc     540
tttccgacgt ggtgagcgtg gaaacgcccg gttgccccgc cgagttcctc aacatccgca     600
tcccacctgg agacctcgtg ttcgaccccg accagcgcgg ggacgtggtg ctgcccttcc     660
agaggagccc ctgggacccc gagaccggac ggagtcccag caaccccgg gacctggcca     720
accaggtgac gggctggctg acggcagcg ccatctatgg ctcctcgcac tcctggagcg     780
acgcgctgcg gagcttctcg gggggacagc tggcgtcggg gcccgacccc gctttccccc     840
gagactcgca gaaccccctg ctcatgtggg cggcgcccga ccccgccacc gggcagaacg     900
```

-continued

| | |
|---|---|
| ggccccgggg gctgtacgcc ttcggggcag agagagggaa ccgggaaccc ttcctgcagg | 960 |
| cgctgggcct gctctggttc cgctaccaca acctgtgggc gcagaggctg gcccgccagc | 1020 |
| acccagactg ggaggacgag gagctgttcc agcacgcacg caagagggtc atcgccacct | 1080 |
| accagaacat cgctgtgtat gagtggctgc ccagcttcct gcagaaaaca ctcccggagt | 1140 |
| atacaggata ccgtcctttc ctagacccca gcatctcccc ggaatttgtg gtggcctctg | 1200 |
| agcagttctt ctctaccatg gtgcccctg tgtctacat gagaaatgcc agctgtcatt | 1260 |
| tccggaaggt cctgaacaag ggttttcaaa gctcccaagc tctcagggtc tgcaacaact | 1320 |
| actggattcg ggagaacccc aatctgaaca gtacccagga ggtgaatgag ctgctgctgg | 1380 |
| gaatggcctc ccagatttcg gagttggagg acaacatagt ggttgaagat ctgagggatt | 1440 |
| actggcctgg ccctggcaaa ttctcccgta cagactatgt ggccagcagc atccaacgtg | 1500 |
| gccgagatat ggggctgccc agctatagcc aggccctgct ggcctttggg ctggacatcc | 1560 |
| caaggaactg gagtgatctc aaccctaatg tggaccccca ggtgctggag ccacagctg | 1620 |
| ccctgtacaa ccaggaccta tcccagctag agctgctcct tggcgggctc ctggagagcc | 1680 |
| atggggaccc tggaccctg ttcagtgcca ttgtcctcga ccagtttgta cggctgcggg | 1740 |
| atggtgaccg ctactggttt gagaacacca ggaatgggct gttctccaag aaggagattg | 1800 |
| aagacatccg aaataccacc ctgcgggacg tgctggtcgc tgttatcaac attgacccca | 1860 |
| gtgccctgca gcccaatgtc tttgtctggc ataaaggtgc accctgccct caacctaagc | 1920 |
| agctcacaac tgacggcctg ccccagtgtg caccctgac tgtgcttgac ttctttgaag | 1980 |
| gcagcagccc tggttttgcc atcaccatca ttgctctctg ctgccttccc ttagtgagtc | 2040 |
| tgcttctctc tggagtggtg gcctatttcc ggggccgaga acacaagaag ctacaaaaga | 2100 |
| aactcaaaga gagcgtgaag aaggaagcag ccaaagatgg agtgccagcg atggagtggc | 2160 |
| caggcccccaa ggagaggagc agtcccatca tcatccagct gctgtcagac aggtgtctgc | 2220 |
| aggtcctgaa caggcatctc actgtgctcc gtgtggtcca gctgcagcct ctgcagcagg | 2280 |
| tcaacctcat cctgtccaac aaccgaggat gccgcaccct gctgctcaag atccctaagg | 2340 |
| agtatgacct ggtgctgctg tttagttctg aagaggaacg gggcgccttt gtgcagcagc | 2400 |
| tatgggactt ctgcgtgcgc tgggctctgg gcctccatgt ggctgagatg agcgagaagg | 2460 |
| agctatttag gaaggctgtg acaaagcagc agcgggaacg catcctggag atcttcttca | 2520 |
| gacaccttt tgctcaggtg ctggacatca accaggccga cgcagggacc ctgcccctgg | 2580 |
| actcctccca gaaggtgcgg gaggccctga cctgcgagct gagcagggcc gagtttgccg | 2640 |
| agtccctggg cctcaagccc caggacatgt tgtggagtc catgttctct ctggctgaca | 2700 |
| aggatggcaa tggctacctg tccttccgag agttcctgga catcctggtg gtcttcatga | 2760 |
| aaggctcccc agaggataag tcccgtctaa tgtttaccat gtatgacctg gatgagaatg | 2820 |
| gcttcctctc caaggacgaa ttcttcacca tgatgcgatc cttcatcgag atctccaaca | 2880 |
| actgcctgtc caaggcccag ctggccgagg tggtggagtc tatgttccgg gagtcgggat | 2940 |
| tccaggacaa ggaggagctg acatgggagg attttcactt catgctgcgg gaccatgaca | 3000 |
| gcgagctccg cttcacgcag ctctgtgtca aggtggagg tggaggtgga aatggtatta | 3060 |
| gagatatctt taaacaaaac atcagctgtc gagtctcgtt catcactcgg acacctgggg | 3120 |
| agcgctccca ccccaggga ctggggcccc ctgtcccaga agccccagag ctggaggcc | 3180 |
| ctggactgaa gaagaggttt ggcaaaaagg cagcagtgcc cactcccgg ctgtacacag | 3240 |
| aggcgctgca agagaagatg cagcgaggct tcctagccca aaagctgcag cagtacaagc | 3300 |

```
gcttcgtgga gaactaccgg aggcacatcg tgtgtgtggc aatcttctcg gccatctgtg    3360
ttggcgtgtt tgcagatcgt gcttactact atggctttgc cttgccaccc tcggacattg    3420
cacagaccac cctcgtgggc atcatcctgt cacgaggcac ggcggccagc gtctccttca    3480
tgttctctta tatcttgctc accatgtgcc gcaacctcat aaccttcctg cgagagactt    3540
tcctcaaccg ctatgtgcct tttgatgccg cagtggactt ccaccgctgg atcgccatgg    3600
ctgctgttgt cctggccatt ttgcacagtg ctggccacga gtcaatgtc tacatcttct    3660 cagtcagccc actcagcctg ctggcctgca tattccccaa cgtctttgtg aatgatgggt    3720
ccaagcttcc ccagaagttc tattggtggt cttccagac cgtcccaggt atgacaggtg    3780
tgcttctgct cctggtcctg gccatcatgt atgtcttcgc ctcccaccac ttccgccgcc    3840
gcagcttccg gggcttctgg ctgacccacc acctctacat cctgctctat gccctgctca    3900
tcatccatgg cagctatgct ctgatccagc tgcccacttt ccacatctac ttcctggtcc    3960
cggcaatcat ctatggaggt gacaagctgg tgagcctgag ccggaagaag gtggagatca    4020
gcgtggtgaa ggcggagctg ctgccctcag gagtgaccta cctgcaattc cagaggcccc    4080 aaggcttttga gtacaagtca ggacagtggg tgcggatcgc ctgcctggct ctggggacca    4140
ccgagtacca ccccttcaca ctgacctccg cgccccatga ggacacactc agcctgcaca    4200
tccgggcagt ggggccctgg accactcgcc tcagggagat ctactcatcc ccaaagggca    4260
atggctgtgc tggataccca aagctgtacc ttgatggacc gtttggagag ggccatcagg    4320
agtggcataa atttgaggtg tcagtgttgg tgggaggggg cattgggtc acccccttg     4380 cctccatcct caaagacctg gtcttcaagt catccttggg cagccaaatg ctgtgtaaga    4440
agatctactt catctgggtg acacggaccc agcgtcagtt tgagtggctg gctgacatca    4500
tccaagaggt ggaggagaac gaccaccagg acctggtgtc tgtgcacatt tatgtcaccc    4560
agctggctga agttcgac ctcaggacca ccatgctata catctgcgag cggcacttcc     4620
agaaagtgct gaaccggagt ctgttcacgg gcctgcgctc catcacccac tttggccgtc    4680 ccccccttcga gcccttcttc aactcccctgc aggaggtcca cccacaggtg cgcaagatcg    4740
gggtgttcag ctgcggccct ccaggaatga ccaagaatgt agagaaggcc tgtcagctcg    4800
tcaacaggca ggaccgagcc cacttcatgc accactatga aacttctga gcctgtcctc    4860 cctggctgct gcttccagta tcctgccttc tcttctgtgc acctaagttg cccagccctg    4920
ctggcaatct ctccatcaga atccacctta ggcctcagct ggagggctgc agagcccctc    4980
ccaatattgg gagaatattg acccagacaa ttatacaaat gagaaaaggc aggagactat    5040
gttctacaat tgcagtgcat gatgattata agtccacctg tttatcaacg gcaccattcc    5100
tgcagccctc cagacttcct gcccttagca agtgcgcaac cagtcaggat ctcccaaaga    5160
agataaagac cactcctcac cccagctcaa gccatggcag gcgtggcaag caaagtgggg    5220
aggagacagt ccctgcttgt gacaagtgtg gaggtgaaaa ggtcaatagt gcttgtctcc    5280
gatagctccc cacatctcta attgacttcc acaaaatcga tgcgttgctt tggtatttgc    5340
ttggactgac atttgaggga ggaggaggct gggatcctct ggctgagaat ctcctcagag    5400
cccagtgcag aagctgtgat gcttagaacc tggacagccc gactgcctca actctgtctc    5460
caggtctatt ccctccagct ccaaaaggag cagcccact tctaccccctt cccgtcccca    5520 aagtgtcagc aactttgagg agggcaccag gaaacaaaga tgccttccca gccctgatat    5580
tcttgatgtc accagtgata cccactgccc tgaccctgg gcaggcccct ctctgcatct    5640
actggagtgg tccctgggct cttggggctg aaggattcca gcctctctgc cagatattca    5700
```

-continued

```
gtactcgatc tcaattcccc tcttccacaa gagttgggtg accagctgtc ctagtttgcc    5760
caggactctc cctgttttag cactgaaagt ctcttgcccc aggaaacccc atcagtccca    5820
ggcagattgg gacagctggt caccttacgc aagagccagg ctgaaacatc ccctccatac    5880
tcagctcttt aacttttctt ttcctttttc atcgggctct ttcctaaaaa gctgagctgt    5940
aaaatatttt acatcgaggt ataataaata atcatgtaca tgttttacca ccacccaggt    6000
caagacatag aatgtttcaa catttccatc accccagaaa ctccccttgt accccttcc     6060
cttcgtctcc cctagctcct agaagcaacc actgatgtga tttctaccaa atccagtttt    6120
ggtcctacta aatatactct tttgagactg gcctctttta ctcaccataa tgcctttgta    6180
attcatccat gctgttgtgt gtatcagcag tttgttcctt ttcattgctg agtagtattc    6240
tattgtagag atgtaccaca gtttgtttat tcttctgttg atggacgttt gggttgtttc    6300
taattttgaa tgattataaa taaaaattct gtgagtgttc ttgtaaaaaa aaaaaaaaaa    6360
aaaaaaaaaa aaaaa                                                    6375
```

<210> SEQ ID NO 14
<211> LENGTH: 1548
<212> TYPE: PRT
<213> ORGANISM: Homo sapiens

<400> SEQUENCE: 14

```
Met Leu Arg Ala Arg Pro Glu Ala Leu Met Leu Leu Gly Ala Leu Leu
1               5                   10                  15

Thr Gly Ser Leu Gly Pro Ser Gly Ser Gln Asp Ala Leu Ser Leu Pro
            20                  25                  30

Trp Glu Val Gln Arg Tyr Asp Gly Trp Phe Asn Asn Leu Arg His His
        35                  40                  45

Glu Arg Gly Ala Val Gly Cys Arg Leu Gln Arg Val Pro Ala Asn
    50                  55                  60

Tyr Ala Asp Gly Val Tyr Gln Ala Leu Glu Glu Pro Gln Leu Pro Asn
65                  70                  75                  80

Pro Arg Arg Leu Ser Asn Ala Ala Thr Arg Gly Ile Ala Gly Leu Pro
                85                  90                  95

Ser Leu His Asn Arg Thr Val Leu Gly Val Phe Phe Gly Tyr His Val
            100                 105                 110

Leu Ser Asp Val Val Ser Val Glu Thr Pro Gly Cys Pro Ala Glu Phe
        115                 120                 125

Leu Asn Ile Arg Ile Pro Pro Gly Asp Leu Val Phe Asp Pro Asp Gln
    130                 135                 140

Arg Gly Asp Val Val Leu Pro Phe Gln Arg Ser Arg Trp Asp Pro Glu
145                 150                 155                 160

Thr Gly Arg Ser Pro Ser Asn Pro Arg Asp Leu Ala Asn Gln Val Thr
                165                 170                 175

Gly Trp Leu Asp Gly Ser Ala Ile Tyr Gly Ser Ser His Ser Trp Ser
            180                 185                 190

Asp Ala Leu Arg Ser Phe Ser Gly Gly Gln Leu Ala Ser Gly Pro Asp
        195                 200                 205

Pro Ala Phe Pro Arg Asp Ser Gln Asn Pro Leu Leu Met Trp Ala Ala
    210                 215                 220

Pro Asp Pro Ala Thr Gly Gln Asn Gly Pro Arg Gly Leu Tyr Ala Phe
225                 230                 235                 240

Gly Ala Glu Arg Gly Asn Arg Glu Pro Phe Leu Gln Ala Leu Gly Leu
                245                 250                 255
```

-continued

Leu Trp Phe Arg Tyr His Asn Leu Trp Ala Gln Arg Leu Ala Arg Gln
            260                 265                 270

His Pro Asp Trp Glu Asp Glu Leu Phe Gln His Ala Arg Lys Arg
        275                 280                 285

Val Ile Ala Thr Tyr Gln Asn Ile Ala Val Tyr Glu Trp Leu Pro Ser
    290                 295                 300

Phe Leu Gln Lys Thr Leu Pro Glu Tyr Thr Gly Tyr Arg Pro Phe Leu
305                 310                 315                 320

Asp Pro Ser Ile Ser Pro Glu Phe Val Val Ala Ser Glu Gln Phe Phe
                325                 330                 335

Ser Thr Met Val Pro Pro Gly Val Tyr Met Arg Asn Ala Ser Cys His
            340                 345                 350

Phe Arg Lys Val Leu Asn Lys Gly Phe Gln Ser Ser Gln Ala Leu Arg
        355                 360                 365

Val Cys Asn Asn Tyr Trp Ile Arg Glu Asn Pro Asn Leu Asn Ser Thr
370                 375                 380

Gln Glu Val Asn Glu Leu Leu Leu Gly Met Ala Ser Gln Ile Ser Glu
385                 390                 395                 400

Leu Glu Asp Asn Ile Val Val Glu Asp Leu Arg Asp Tyr Trp Pro Gly
                405                 410                 415

Pro Gly Lys Phe Ser Arg Thr Asp Tyr Val Ala Ser Ser Ile Gln Arg
        420                 425                 430

Gly Arg Asp Met Gly Leu Pro Ser Tyr Ser Gln Ala Leu Leu Ala Phe
            435                 440                 445

Gly Leu Asp Ile Pro Arg Asn Trp Ser Asp Leu Asn Pro Asn Val Asp
        450                 455                 460

Pro Gln Val Leu Glu Ala Thr Ala Ala Leu Tyr Asn Gln Asp Leu Ser
465                 470                 475                 480

Gln Leu Glu Leu Leu Leu Gly Leu Leu Glu Ser His Gly Asp Pro
                485                 490                 495

Gly Pro Leu Phe Ser Ala Ile Val Leu Asp Gln Phe Val Arg Leu Arg
        500                 505                 510

Asp Gly Asp Arg Tyr Trp Phe Glu Asn Thr Arg Asn Gly Leu Phe Ser
    515                 520                 525

Lys Lys Glu Ile Glu Asp Ile Arg Asn Thr Thr Leu Arg Asp Val Leu
    530                 535                 540

Val Ala Val Ile Asn Ile Asp Pro Ser Ala Leu Gln Pro Asn Val Phe
545                 550                 555                 560

Val Trp His Lys Gly Ala Pro Cys Pro Gln Pro Lys Gln Leu Thr Thr
                565                 570                 575

Asp Gly Leu Pro Gln Cys Ala Pro Leu Thr Val Leu Asp Phe Phe Glu
        580                 585                 590

Gly Ser Ser Pro Gly Phe Ala Ile Thr Ile Ala Leu Cys Cys Leu
        595                 600                 605

Pro Leu Val Ser Leu Leu Ser Gly Val Val Ala Tyr Phe Arg Gly
    610                 615                 620

Arg Glu His Lys Lys Leu Gln Lys Lys Leu Lys Glu Ser Val Lys Lys
625                 630                 635                 640

Glu Ala Ala Lys Asp Gly Val Pro Ala Met Glu Trp Pro Gly Pro Lys
                645                 650                 655

Glu Arg Ser Ser Pro Ile Ile Ile Gln Leu Leu Ser Asp Arg Cys Leu
        660                 665                 670

-continued

```
Gln Val Leu Asn Arg His Leu Thr Val Leu Arg Val Gln Leu Gln
            675                 680                 685
Pro Leu Gln Gln Val Asn Leu Ile Leu Ser Asn Asn Arg Gly Cys Arg
690                 695                 700
Thr Leu Leu Leu Lys Ile Pro Lys Glu Tyr Asp Leu Val Leu Leu Phe
705                 710                 715                 720
Ser Ser Glu Glu Glu Arg Gly Ala Phe Val Gln Gln Leu Trp Asp Phe
                725                 730                 735
Cys Val Arg Trp Ala Leu Gly Leu His Val Ala Glu Met Ser Glu Lys
                740                 745                 750
Glu Leu Phe Arg Lys Ala Val Thr Lys Gln Gln Arg Glu Arg Ile Leu
            755                 760                 765
Glu Ile Phe Phe Arg His Leu Phe Ala Gln Val Leu Asp Ile Asn Gln
            770                 775                 780
Ala Asp Ala Gly Thr Leu Pro Leu Asp Ser Ser Gln Lys Val Arg Glu
785                 790                 795                 800
Ala Leu Thr Cys Glu Leu Ser Arg Ala Glu Phe Ala Glu Ser Leu Gly
                805                 810                 815
Leu Lys Pro Gln Asp Met Phe Val Glu Ser Met Phe Ser Leu Ala Asp
            820                 825                 830
Lys Asp Gly Asn Gly Tyr Leu Ser Phe Arg Glu Phe Leu Asp Ile Leu
            835                 840                 845
Val Val Phe Met Lys Gly Ser Pro Glu Asp Lys Ser Arg Leu Met Phe
850                 855                 860
Thr Met Tyr Asp Leu Asp Glu Asn Gly Phe Leu Ser Lys Asp Glu Phe
865                 870                 875                 880
Phe Thr Met Met Arg Ser Phe Ile Glu Ile Ser Asn Asn Cys Leu Ser
                885                 890                 895
Lys Ala Gln Leu Ala Glu Val Val Glu Ser Met Phe Arg Glu Ser Gly
                900                 905                 910
Phe Gln Asp Lys Glu Glu Leu Thr Trp Glu Asp Phe His Phe Met Leu
            915                 920                 925
Arg Asp His Asp Ser Glu Leu Arg Phe Thr Gln Leu Cys Val Lys Gly
            930                 935                 940
Gly Gly Gly Gly Gly Asn Gly Ile Arg Asp Ile Phe Lys Gln Asn Ile
945                 950                 955                 960
Ser Cys Arg Val Ser Phe Ile Thr Arg Thr Pro Gly Glu Arg Ser His
                965                 970                 975
Pro Gln Gly Leu Gly Pro Val Pro Glu Ala Pro Glu Leu Gly Gly
            980                 985                 990
Pro Gly Leu Lys Lys Arg Phe Gly Lys Lys Ala Ala Val Pro Thr Pro
            995                 1000                1005
Arg Leu Tyr Thr Glu Ala Leu Gln Glu Lys Met Gln Arg Gly Phe Leu
            1010                1015                1020
Ala Gln Lys Leu Gln Gln Tyr Lys Arg Phe Val Glu Asn Tyr Arg Arg
1025                1030                1035                1040
His Ile Val Cys Val Ala Ile Phe Ser Ala Ile Cys Val Gly Val Phe
                1045                1050                1055
Ala Asp Arg Ala Tyr Tyr Tyr Gly Phe Ala Leu Pro Pro Ser Asp Ile
            1060                1065                1070
Ala Gln Thr Thr Leu Val Gly Ile Ile Leu Ser Arg Gly Thr Ala Ala
            1075                1080                1085
```

-continued

Ser Val Ser Phe Met Phe Ser Tyr Ile Leu Leu Thr Met Cys Arg Asn
    1090                1095                1100

Leu Ile Thr Phe Leu Arg Glu Thr Phe Leu Asn Arg Tyr Val Pro Phe
1105                1110                1115                1120

Asp Ala Ala Val Asp Phe His Arg Trp Ile Ala Met Ala Ala Val Val
            1125                1130                1135

Leu Ala Ile Leu His Ser Ala Gly His Ala Val Asn Val Tyr Ile Phe
        1140                1145                1150

Ser Val Ser Pro Leu Ser Leu Leu Ala Cys Ile Phe Pro Asn Val Phe
        1155                1160                1165

Val Asn Asp Gly Ser Lys Leu Pro Gln Lys Phe Tyr Trp Trp Phe Phe
    1170                1175                1180

Gln Thr Val Pro Gly Met Thr Gly Val Leu Leu Leu Val Leu Ala
1185                1190                1195                1200

Ile Met Tyr Val Phe Ala Ser His His Phe Arg Arg Arg Ser Phe Arg
            1205                1210                1215

Gly Phe Trp Leu Thr His His Leu Tyr Ile Leu Leu Tyr Ala Leu Leu
            1220                1225                1230

Ile Ile His Gly Ser Tyr Ala Leu Ile Gln Leu Pro Thr Phe His Ile
        1235                1240                1245

Tyr Phe Leu Val Pro Ala Ile Ile Tyr Gly Gly Asp Lys Leu Val Ser
    1250                1255                1260

Leu Ser Arg Lys Lys Val Glu Ile Ser Val Val Lys Ala Glu Leu Leu
1265                1270                1275                1280

Pro Ser Gly Val Thr Tyr Leu Gln Phe Gln Arg Pro Gln Gly Phe Glu
            1285                1290                1295

Tyr Lys Ser Gly Gln Trp Val Arg Ile Ala Cys Leu Ala Leu Gly Thr
        1300                1305                1310

Thr Glu Tyr His Pro Phe Thr Leu Thr Ser Ala Pro His Glu Asp Thr
        1315                1320                1325

Leu Ser Leu His Ile Arg Ala Val Gly Pro Trp Thr Thr Arg Leu Arg
    1330                1335                1340

Glu Ile Tyr Ser Ser Pro Lys Gly Asn Gly Cys Ala Gly Tyr Pro Lys
1345                1350                1355                1360

Leu Tyr Leu Asp Gly Pro Phe Gly Glu Gly His Gln Glu Trp His Lys
            1365                1370                1375

Phe Glu Val Ser Val Leu Val Gly Gly Gly Ile Gly Val Thr Pro Phe
            1380                1385                1390

Ala Ser Ile Leu Lys Asp Leu Val Phe Lys Ser Ser Leu Gly Ser Gln
        1395                1400                1405

Met Leu Cys Lys Lys Ile Tyr Phe Ile Trp Val Thr Arg Thr Gln Arg
    1410                1415                1420

Gln Phe Glu Trp Leu Ala Asp Ile Ile Gln Glu Val Glu Glu Asn Asp
1425                1430                1435                1440

His Gln Asp Leu Val Ser Val His Ile Tyr Val Thr Gln Leu Ala Glu
            1445                1450                1455

Lys Phe Asp Leu Arg Thr Thr Met Leu Tyr Ile Cys Glu Arg His Phe
        1460                1465                1470

Gln Lys Val Leu Asn Arg Ser Leu Phe Thr Gly Leu Arg Ser Ile Thr
        1475                1480                1485

His Phe Gly Arg Pro Pro Phe Glu Pro Phe Phe Asn Ser Leu Gln Glu
    1490                1495                1500

Val His Pro Gln Val Arg Lys Ile Gly Val Phe Ser Cys Gly Pro Pro
1505                1510                1515                1520

Gly Met Thr Lys Asn Val Glu Lys Ala Cys Gln Leu Val Asn Arg Gln
            1525                1530                1535

Asp Arg Ala His Phe Met His His Tyr Glu Asn Phe
        1540                1545

<210> SEQ ID NO 15
<211> LENGTH: 1676
<212> TYPE: DNA
<213> ORGANISM: Homo sapiens

<400> SEQUENCE: 15

```
agccttatgg attggattcg actgaccaaa agtggaaagg atctaacggg attaaaaggc      60
aggttaattg aagtaactga agaagaactt aagaaacaca acaaaaaaga tgattgttgg     120
atatgcataa gaggtttcgt ttataatgtc agcccttata tggagtatca tcctggtgga     180
gaagatgaac taatgagagc agcaggatca gatggtactg aacttttga tcaggttcat      240
cgttgggtca attatgaatc catgctgaaa gaatgcctgg ttggcagaat ggccattaaa     300
cctgctgttc tgaaagacta cgtgaggag gaaaagaaag tcttaaatgg catgcttccc      360
aagagccaag tgacagatac acttgccaaa gaaggtccta gttatccaag ctatgattgg     420
ttccaaacag actctttagt caccattgcc atatatacta aacagaagga tatcaattta     480
gactcaatta tagttgatca tcagaatgat tcctttagag cagaaacaat tattaaggat     540
tgtttatatc ttatacatat tgggctaagc catgaggttc aggaagattt ttctgtgcgg     600
gttgttgaga gtgtgggaaa atagagatt gttctacaaa aaaagagaa tacttcttgg      660
gactttcttg gccatcccct gaagaatcat aattcactta ttccaaggaa agatacaggt     720
ttgtactaca gaaagtgcca gttaatttcc aaggaagatg ttactcatga tacgaggctt     780
ttctgtttga tgctgccacc aagcactcat cttcaagtgc ccattgggca acatgtttac     840
ctcaagctac ctattacagg tacagaaata gtaaagccat atacacctgt atctggttcc     900
ttactctcag agttcaagga accagttctt cccaacaata aatacatcta cttttttgata    960
aaaatctatc ccactggact cttcacacca gagcttgatc gtcttcagat tggagatttt    1020
gtttctgtaa gcagtcctga gggcaatttt aaaatatcca agttccaaga attagaagat    1080
ctcttttttgt tggcagctgg aacaggcttc acaccaatgg ttaaaatact gaattatgct    1140
ttgactgata tacccagtct caggaaagtg aagctgatgt tcttcaataa aacagaagat    1200
gatataattt ggagaagcca attggagaaa ttagcattta aagataaaag actggatgtt    1260
gaatttgttc tctcagcacc tatttctgaa tggaatggca acagggaca tatttcacca    1320
gctcttcttt ctgaattttt gaaaagaaat ttggacaaat ccaagttct cgtctgcatt    1380
tgtggaccag tgccatttac agaacaagga gtaaggttgc tgcatgatct caactttttcc    1440
aaaaatgaga tccatagttt tacagcataa tgaagagctg tcattgtcct ttattcaact    1500
agtttatcta aatttgtgat tgcttagggt ttttaagag aacattttg tacataacaa      1560
aaggttaact agaatccagc cttcagtttc ttaaatgaaa tcaaatgttc cttcagtaca    1620
ggtaacttct tggctttctt ttgtaccaca acttatttta ctactgatat ttgacc         1676
```

<210> SEQ ID NO 16
<211> LENGTH: 487
<212> TYPE: PRT
<213> ORGANISM: Homo sapiens

<400> SEQUENCE: 16

```
Met Asp Trp Ile Arg Leu Thr Lys Ser Gly Lys Asp Leu Thr Gly Leu
1               5                   10                  15

Lys Gly Arg Leu Ile Glu Val Thr Glu Glu Leu Lys Lys His Asn
            20                  25                  30

Lys Lys Asp Asp Cys Trp Ile Cys Ile Arg Gly Phe Val Tyr Asn Val
            35                  40                  45

Ser Pro Tyr Met Glu Tyr His Pro Gly Gly Glu Asp Glu Leu Met Arg
    50                  55                  60

Ala Ala Gly Ser Asp Gly Thr Glu Leu Phe Asp Gln Val His Arg Trp
65                  70                  75                  80

Val Asn Tyr Glu Ser Met Leu Lys Glu Cys Leu Val Gly Arg Met Ala
                85                  90                  95

Ile Lys Pro Ala Val Leu Lys Asp Tyr Arg Glu Glu Lys Lys Val
            100                 105                 110

Leu Asn Gly Met Leu Pro Lys Ser Gln Val Thr Asp Thr Leu Ala Lys
            115                 120                 125

Glu Gly Pro Ser Tyr Pro Ser Tyr Asp Trp Phe Gln Thr Asp Ser Leu
            130                 135                 140

Val Thr Ile Ala Ile Tyr Thr Lys Gln Lys Asp Ile Asn Leu Asp Ser
145                 150                 155                 160

Ile Ile Val Asp His Gln Asn Asp Ser Phe Arg Ala Glu Thr Ile Ile
                165                 170                 175

Lys Asp Cys Leu Tyr Leu Ile His Ile Gly Leu Ser His Glu Val Gln
            180                 185                 190

Glu Asp Phe Ser Val Arg Val Val Glu Ser Val Gly Lys Ile Glu Ile
            195                 200                 205

Val Leu Gln Lys Lys Glu Asn Thr Ser Trp Asp Phe Leu Gly His Pro
210                 215                 220

Leu Lys Asn His Asn Ser Leu Ile Pro Arg Lys Asp Thr Gly Leu Tyr
225                 230                 235                 240

Tyr Arg Lys Cys Gln Leu Ile Ser Lys Glu Asp Val Thr His Asp Thr
                245                 250                 255

Arg Leu Phe Cys Leu Met Leu Pro Pro Ser Thr His Leu Gln Val Pro
            260                 265                 270

Ile Gly Gln His Val Tyr Leu Lys Leu Pro Ile Thr Gly Thr Glu Ile
            275                 280                 285

Val Lys Pro Tyr Thr Pro Val Ser Gly Ser Leu Leu Ser Glu Phe Lys
            290                 295                 300

Glu Pro Val Leu Pro Asn Asn Lys Tyr Ile Tyr Phe Leu Ile Lys Ile
305                 310                 315                 320

Tyr Pro Thr Gly Leu Phe Thr Pro Glu Leu Asp Arg Leu Gln Ile Gly
                325                 330                 335

Asp Phe Val Ser Val Ser Ser Pro Glu Gly Asn Phe Lys Ile Ser Lys
            340                 345                 350

Phe Gln Glu Leu Glu Asp Leu Phe Leu Ala Ala Gly Thr Gly Phe
            355                 360                 365

Thr Pro Met Val Lys Ile Leu Asn Tyr Ala Leu Thr Asp Ile Pro Ser
370                 375                 380

Leu Arg Lys Val Lys Leu Met Phe Phe Asn Lys Thr Glu Asp Asp Ile
385                 390                 395                 400

Ile Trp Arg Ser Gln Leu Glu Lys Leu Ala Phe Lys Asp Lys Arg Leu
                405                 410                 415
```

```
Asp Val Glu Phe Val Leu Ser Ala Pro Ile Ser Glu Trp Asn Gly Lys
            420                 425                 430

Gln Gly His Ile Ser Pro Ala Leu Leu Ser Glu Phe Leu Lys Arg Asn
        435                 440                 445

Leu Asp Lys Ser Lys Val Leu Val Cys Ile Cys Gly Pro Val Pro Phe
    450                 455                 460

Thr Glu Gln Gly Val Arg Leu Leu His Asp Leu Asn Phe Ser Lys Asn
465                 470                 475                 480

Glu Ile His Ser Phe Thr Ala
                485

<210> SEQ ID NO 17
<211> LENGTH: 1340
<212> TYPE: DNA
<213> ORGANISM: Homo sapiens

<400> SEQUENCE: 17
ccacccagtc atggggaca ccttcatccg tcacatcgcc ctgctgggct ttgagaagcg      60
cttcgtaccc agccagcact atgtgtacat gttcctggtg aaatggcagg acctgtcgga     120
gaaggtggtc taccggcgct tcaccgagat ctacgagtta cataaaacct aaaagaaat     180 gttccctatt gaggcagggg cgatcaatcc agagaacagg atcatccccc acctcccagc     240
tcccaagtgg tttgacgggc agcgggccgc cgagaaccgc cagggcacac ttaccgagta     300
ctgcagcacg ctcatgagcc tgcccaccaa gatctcccgc tgtccccacc tcctcgactt     360
cttcaaggtg cgccctgatg acctcaagct ccccacggac aaccagacaa aaaagccaga     420
gacatacttg atgcccaaag atggcaagag taccgcgaca gacatcaccg gccccatcat     480
cctgcagacg taccgcgcca ttgccgacta cgagaagacc tcgggctccg agatggctct     540
gtccacgggg gacgtggtgg aggtcgtgga agagcgag agcggttggt ggttctgtca     600
gatgaaagca aagcgaggct ggatcccagc atccttcctc gagcccctgg acagtcctga     660
cgagacggaa gaccctgagc ccaactatgc aggtgagcca tacgtcgcca tcaaggccta     720
cactgctgtg gaggggacg aggtgtccct gctcgagggt gaagctgttg aggtcattca     780
caagctcctg gacggctggt gggtcatcag gaaagacgac gtcacaggct actttccgtc     840
catgtacctg caaaagtcgg ggcaagacgt gtcccaggcc aacgccaga tcaagcgggg     900 ggcgccgccc cgcaggtcgt ccatccgcaa cgcgcacagc atccatcagc ggtcgcggaa     960
gcgcctcagc caggacgcct atcgccgcaa cagcgtccgt tttctgcagc agcgacgccg    1020
ccaggcgcgg ccgggaccgc agagcccgg gagcccgctc gaggaggagc ggcagacgca    1080
gcgctctaaa ccgcagccgg cggtgccccc gcggccgagc gccgacctca tcctgaaccg    1140
ctgcagcgag agcaccaagc ggaagctggc gtctgccgtc tgaggctgga gcgcagtccc    1200
cagctagcgt ctcggccctt gccgcccgt gcctgtacat acgtgttcta tagagcctgg    1260
cgtctggacg ccgagggcag ccccgacccc tgtccagcgc ggctcccgcc accctcaata    1320
aatgttgctt ggagtggaag                                                1340

<210> SEQ ID NO 18
<211> LENGTH: 390
<212> TYPE: PRT
<213> ORGANISM: Homo sapiens

<400> SEQUENCE: 18

Met Gly Asp Thr Phe Ile Arg His Ile Ala Leu Leu Gly Phe Glu Lys
1               5                   10                  15
```

```
Arg Phe Val Pro Ser Gln His Tyr Val Tyr Met Phe Leu Val Lys Trp
            20                  25                  30

Gln Asp Leu Ser Glu Lys Val Tyr Arg Arg Phe Thr Glu Ile Tyr
        35                  40                  45

Glu Phe His Lys Thr Leu Lys Glu Met Phe Pro Ile Glu Ala Gly Ala
 50                  55                  60

Ile Asn Pro Glu Asn Arg Ile Ile Pro His Leu Pro Ala Pro Lys Trp
 65                  70                  75                  80

Phe Asp Gly Gln Arg Ala Ala Glu Asn Arg Gln Gly Thr Leu Thr Glu
                85                  90                  95

Tyr Cys Ser Thr Leu Met Ser Leu Pro Thr Lys Ile Ser Arg Cys Pro
                100                 105                 110

His Leu Leu Asp Phe Phe Lys Val Arg Pro Asp Asp Leu Lys Leu Pro
            115                 120                 125

Thr Asp Asn Gln Thr Lys Lys Pro Glu Thr Tyr Leu Met Pro Lys Asp
130                 135                 140

Gly Lys Ser Thr Ala Thr Asp Ile Thr Gly Pro Ile Ile Leu Gln Thr
145                 150                 155                 160

Tyr Arg Ala Ile Ala Asp Tyr Glu Lys Thr Ser Gly Ser Glu Met Ala
                165                 170                 175

Leu Ser Thr Gly Asp Val Val Glu Val Val Glu Lys Ser Glu Ser Gly
            180                 185                 190

Trp Trp Phe Cys Gln Met Lys Ala Lys Arg Gly Trp Ile Pro Ala Ser
            195                 200                 205

Phe Leu Glu Pro Leu Asp Ser Pro Asp Glu Thr Glu Asp Pro Glu Pro
210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Glu Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
            275                 280                 285

Gln Ala Gln Arg Gln Ile Lys Arg Gly Ala Pro Pro Arg Arg Ser Ser
        290                 295                 300

Ile Arg Asn Ala His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335

Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
370                 375                 380

Lys Leu Ala Ser Ala Val
385                 390

<210> SEQ ID NO 19
<211> LENGTH: 2206
<212> TYPE: DNA
<213> ORGANISM: Homo sapiens
```

<400> SEQUENCE: 19

```
ctagtctttc agccttcagg ctgttttgg cttgaagctc tcttggcctc ctagtttcta        60
cctaatcatg tccctggtgg aggccatcag cctctggaat gaaggggtgc tggcagcgga       120
caagaaggac tggaagggag ccctggatgc cttcagtgcc gtccaggacc cccactcccg       180
gatttgcttc aacattggct gcatgtacac tatcctgaag aacatgactg aagcagagaa       240
ggcctttacc agaagcatta accgagacaa gcacttggca gtggcttact ccaacgagg        300
gatgctctac taccagacag agaaatatga tttggctatc aaagaccta aagaagcctt        360
gattcagctt cgagggaacc agctgataga ctataagatc ctggggctcc agttcaagct       420
gttttgcctgt gaggtgttat ataacattgc tttcatgtat gccaagaagg aggaatggaa      480
aaaagctgaa gaacagttag cattggccac gagcatgaag tctgagccca gacattccaa       540
aatcgacaag gcgatggagt gtgtctggaa gcagaagcta tatgagccag tggtgatccc       600
tgtgggcaag ctgtttcgac caaatgagag acaagtggct cagctggcca agaaggatta       660
cctaggcaag gcgacggtcg tggcatctgt ggtggatcaa gacagtttct ctgggtttgc       720
ccctctgcaa ccacaggcag ctgagcctcc acccagaccg aaaacccag agatcttcag       780
ggctctggaa ggggaggctc accgtgtgct atttgggttt gtgcctgaga caaaagaaga      840
gctccaggtc atgccaggga acattgtctt tgtcttgaag aagggcaatg ataactgggc       900
cacggtcatg ttcaacgggc agaaggggct tgttccctgc aactaccttg aaccagttga       960
gttgcggatc caccctcagc agcagcccca ggaggaaagc tctccgcagt ccgacatccc      1020
agctcctcct agttccaaag ccccctggaaa accccagctg tcaccaggcc agaaacaaaa     1080
agaagagcct aaggaagtga agctcagtgt tcccatgccc tacacactca aggtgcacta      1140
caagtacacg gtagtcatga agactcagcc cgggctcccc tacagccagg tccgggacat      1200
ggtgtctaag aaactggagc tccggctgga acacactaag ctgagctatc ggcctcggga      1260
cagcaatgag ctggtgcccc tttcagaaga cagcatgaag gatgcctggg gccaggtgaa      1320
aaactactgc ctgactctgt ggtgtgagaa cacagtgggt gaccaaggct ttccagatga     1380
acccaaggaa agtgaaaaag ctgatgctaa taaccagaca acagaacctc agcttaagaa     1440
aggcagccaa gtggaggcac tcttcagtta tgaggctacc caaccagagg acctggagtt     1500
tcaggaaggg gatataatcc tggtgttatc aaaggtgaat gaagaatggc tggaagggga     1560
gtgcaaaggg aaggtgggca ttttccccaa agttttgtt gaagactgcg caactacaga     1620
tttgaaagc actcggagag aagtctagga tgtttcacaa actacaaagc tgaagaaaat      1680
gaagccctat tacttgtttg taagatttag caccccttctg ctgtatactg tactgagaca     1740
ttacagtttg gaagtgttaa ctatttattc cctgttaaaa tttaacctac tagacaatga     1800
tgtgagtacc aggatgatt tcctggggca cagtgggtga ggagatgggg acaggtgaat     1860
ggaggagtta ggggagagga aaagtggatg gaagtgtctg gaaagggcac gagagagtct    1920
tccaggtact gatcctgttt cttgctctga gtgctagcta gccagctgtg ttcacactgt    1980
aaacattcat caagctgtac atttggtgca cttttctgtg tcataccaca ataaaaaaaa    2040
acctatcatc atcttacaaa aacaagacac ccaagtccag gcccaaggag taagtacaaa    2100
tattcctgtt tctgaaccat tactgtaatt ggctcttaag gcttgaagta accttatagg    2160
ttactcataa ggcatataca aataaacttg tttgttttct ttttc                    2206
```

-continued

<210> SEQ ID NO 20
<211> LENGTH: 526
<212> TYPE: PRT
<213> ORGANISM: Homo sapiens

<400> SEQUENCE: 20

```
Met Ser Leu Val Glu Ala Ile Ser Leu Trp Asn Glu Gly Val Leu Ala
1               5                   10                  15

Ala Asp Lys Lys Asp Trp Lys Gly Ala Leu Asp Ala Phe Ser Ala Val
            20                  25                  30

Gln Asp Pro His Ser Arg Ile Cys Phe Asn Ile Gly Cys Met Tyr Thr
        35                  40                  45

Ile Leu Lys Asn Met Thr Glu Ala Glu Lys Ala Phe Thr Arg Ser Ile
50                  55                  60

Asn Arg Asp Lys His Leu Ala Val Ala Tyr Phe Gln Arg Gly Met Leu
65                  70                  75                  80

Tyr Tyr Gln Thr Glu Lys Tyr Asp Leu Ala Ile Lys Asp Leu Lys Glu
                85                  90                  95

Ala Leu Ile Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
        115                 120                 125

Phe Met Tyr Ala Lys Lys Glu Glu Trp Lys Lys Ala Glu Glu Gln Leu
    130                 135                 140

Ala Leu Ala Thr Ser Met Lys Ser Glu Pro Arg His Ser Lys Ile Asp
145                 150                 155                 160

Lys Ala Met Glu Cys Val Trp Lys Gln Lys Leu Tyr Glu Pro Val Val
                165                 170                 175

Ile Pro Val Gly Lys Leu Phe Arg Pro Asn Glu Arg Gln Val Ala Gln
            180                 185                 190

Leu Ala Lys Lys Asp Tyr Leu Gly Lys Ala Thr Val Val Ala Ser Val
        195                 200                 205

Val Asp Gln Asp Ser Phe Ser Gly Phe Ala Pro Leu Gln Pro Gln Ala
    210                 215                 220

Ala Glu Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Lys
                245                 250                 255

Glu Glu Leu Gln Val Met Pro Gly Asn Ile Val Phe Val Leu Lys Lys
            260                 265                 270

Gly Asn Asp Asn Trp Ala Thr Val Met Phe Asn Gly Gln Lys Gly Leu
        275                 280                 285

Val Pro Cys Asn Tyr Leu Glu Pro Val Glu Leu Arg Ile His Pro Gln
    290                 295                 300

Gln Gln Pro Gln Glu Glu Ser Ser Pro Gln Ser Asp Ile Pro Ala Pro
305                 310                 315                 320

Pro Ser Ser Lys Ala Pro Gly Lys Pro Gln Leu Ser Pro Gly Gln Lys
                325                 330                 335

Gln Lys Glu Glu Pro Lys Glu Val Lys Leu Ser Val Pro Met Pro Tyr
            340                 345                 350

Thr Leu Lys Val His Tyr Lys Tyr Thr Val Val Met Lys Thr Gln Pro
        355                 360                 365

Gly Leu Pro Tyr Ser Gln Val Arg Asp Met Val Ser Lys Lys Leu Glu
    370                 375                 380
```

-continued

| | | | | | | | | | | | |
|---|---|---|---|---|---|---|---|---|---|---|---|
|Leu|Arg|Leu|Glu|His|Thr|Lys|Leu|Ser|Tyr|Arg|Pro|Arg|Asp|Ser|Asn|
|385| | | |390| | | |395| | | |400|

Glu Leu Val Pro Leu Ser Glu Asp Ser Met Lys Asp Ala Trp Gly Gln
               405               410              415

Val Lys Asn Tyr Cys Leu Thr Leu Trp Cys Glu Asn Thr Val Gly Asp
            420               425               430

Gln Gly Phe Pro Asp Glu Pro Lys Glu Ser Lys Ala Asp Ala Asn
        435               440               445

Asn Gln Thr Thr Glu Pro Gln Leu Lys Lys Gly Ser Gln Val Glu Ala
            450               455               460

Leu Phe Ser Tyr Glu Ala Thr Gln Pro Glu Asp Leu Glu Phe Gln Glu
465               470               475               480

Gly Asp Ile Ile Leu Val Leu Ser Lys Val Asn Glu Glu Trp Leu Glu
              485               490               495

Gly Glu Cys Lys Gly Lys Val Gly Ile Phe Pro Lys Val Phe Val Glu
        500               505               510

Asp Cys Ala Thr Thr Asp Leu Glu Ser Thr Arg Arg Glu Val
        515               520             525

<210> SEQ ID NO 21
<211> LENGTH: 1301
<212> TYPE: DNA
<213> ORGANISM: Homo sapiens

<400> SEQUENCE: 21

```
agactctcca cctgctccct gggaccatcg cccaccatgg ctgtggccca gcagctgcgg      60
gccgagagtg actttgaaca gcttccggat gatgttgcca tctcggccaa cattgctgac     120
atcgaggaga agagaggctt caccagccac tttgttttcg tcatcgaggt gaagacaaaa     180
ggaggatcca agtacctcat ctaccgccgc taccgccagt ccatgctttt gcagagcaag     240
ctggaggagc gcttcgggcc agacagcaag agcagtgccc tggcctgtac cctgcccaca     300
ctcccagcca agtctacgt gggtgtgaaa caggagatcg ccgagatgcg gatacctgcc     360
ctcaacgcct acatgaagag cctgctcagc ctgccggtct gggtgctgat ggatgaggac     420
gtccggatct tcttttacca gtcgccctat gactcagagc aggtgcccca ggcactccgc     480
cggctccgcc cgcgcacccg gaaagtcaag agcgtgtccc acagggcaa cagcgttgac     540
cgcatggcag ctccgagagc agaggctcta tttgacttca ctggaaacag caaactggag     600
ctgaatttca agctggaga tgtgatcttc tcctcagtc ggatcaacaa agactggctg     660
gagggcactg tccggggagc cacgggcatc ttccctctct ccttcgtgaa gatcctcaaa     720
gacttccctg aggaggacga ccccaccaac tggctgcgtt gctactacta cgaagacacc     780
atcagcacca tcaagtctgt ggcctgggag ggaggggcct gtccagcctt cctgccatcc     840
ctacgaccac cgcccctcac atcaccttct catgggtccc tctcccactc caaagccccc     900
agtggctccc agatgagcca caatgctgta caagccatc aacgtccagg gtggcctggc     960
cagcctcatt cccctttccc ccaccccaca ccccacttcc agcctgatgc ctccttactc    1020
cagcctgtca ccccccttagg gacatcgcgg tggaggaaga tctcagcagc actcccctat    1080
tgaaagacct gctggagctc acaaggcggg agttccagag agaggacata gctctgaatt    1140
accgggacgc tgagggggat ctggttcggc tgctgtcgga tgaggacgta gcgctcatgg    1200
tgcggcaggc tcgtggcctc ccctcccaga agcgcctctt ccctggaag ctgcacatca    1260
cgcagaagga caactacagg gtctacaaca cgatgccatg a                        1301
```

```
<210> SEQ ID NO 22
<211> LENGTH: 348
<212> TYPE: PRT
<213> ORGANISM: Homo sapiens

<400> SEQUENCE: 22
```

Met Ala Val Ala Gln Gln Leu Arg Ala Glu Ser Asp Phe Glu Gln Leu
1               5                   10                  15

Pro Asp Asp Val Ala Ile Ser Ala Asn Ile Ala Asp Ile Glu Glu Lys
            20                  25                  30

Arg Gly Phe Thr Ser His Phe Val Phe Val Ile Glu Val Lys Thr Lys
        35                  40                  45

Gly Gly Ser Lys Tyr Leu Ile Tyr Arg Arg Tyr Arg Gln Phe His Ala
    50                  55                  60

Leu Gln Ser Lys Leu Glu Glu Arg Phe Gly Pro Asp Ser Lys Ser Ser
65                  70                  75                  80

Ala Leu Ala Cys Thr Leu Pro Thr Leu Pro Ala Lys Val Tyr Val Gly
                85                  90                  95

Val Lys Gln Glu Ile Ala Glu Met Arg Ile Pro Ala Leu Asn Ala Tyr
            100                 105                 110

Met Lys Ser Leu Leu Ser Leu Pro Val Trp Val Leu Met Asp Glu Asp
        115                 120                 125

Val Arg Ile Phe Phe Tyr Gln Ser Pro Tyr Asp Ser Glu Gln Val Pro
    130                 135                 140

Gln Ala Leu Arg Arg Leu Arg Pro Arg Thr Arg Lys Val Lys Ser Val
145                 150                 155                 160

Ser Pro Gln Gly Asn Ser Val Asp Arg Met Ala Ala Pro Arg Ala Glu
                165                 170                 175

Ala Leu Phe Asp Phe Thr Gly Asn Ser Lys Leu Glu Leu Asn Phe Lys
            180                 185                 190

Ala Gly Asp Val Ile Phe Leu Leu Ser Arg Ile Asn Lys Asp Trp Leu
        195                 200                 205

Glu Gly Thr Val Arg Gly Ala Thr Gly Ile Phe Pro Leu Ser Phe Val
    210                 215                 220

Lys Ile Leu Lys Asp Phe Pro Glu Glu Asp Asp Pro Thr Asn Trp Leu
225                 230                 235                 240

Arg Cys Tyr Tyr Tyr Glu Asp Thr Ile Ser Thr Ile Lys Ser Val Ala
                245                 250                 255

Trp Glu Gly Gly Ala Cys Pro Ala Phe Leu Pro Ser Leu Arg Pro Pro
            260                 265                 270

Pro Leu Thr Ser Pro Ser His Gly Ser Leu Ser His Ser Lys Ala Pro
        275                 280                 285

Ser Gly Ser Gln Met Ser His Asn Ala Val Thr Ser His Gln Arg Pro
    290                 295                 300

Gly Trp Pro Gly Gln Pro His Ser Pro Phe Pro His Pro Thr Pro His
305                 310                 315                 320

Phe Gln Pro Asp Ala Ser Leu Leu Gln Pro Val Thr Pro Leu Gly Thr
                325                 330                 335

Ser Arg Trp Arg Lys Ile Ser Ala Ala Leu Pro Tyr
            340                 345

```
<210> SEQ ID NO 23
<211> LENGTH: 28567
<212> TYPE: DNA
<213> ORGANISM: Homo sapiens
```

<400> SEQUENCE: 23

```
gtttcaccat gttggtgagg ctggtctcaa actcctgaac ttgtgatcca cccacctggg      60
ccgcccaacc aaagtgctgg gatgacagac gtgagccact gcgcccagcc accacaggtt     120
cctcttttt tttttttttt ttgagacggg gtctcgctct gactccaggc tggagtgcag     180
tggcgccatc tgggctcact gaaaccaccg cctcccaggt tcaagagatt ctcctgcctc     240
aggctcctga gtagctggaa ctacaggcgc gcgcctccac gccctgctaa tctaattttt     300
gtattttag tagagacggg gtttcaccat gttggccagg atggtctcga tctcttgacc     360
ttgtgatccg ccctcctcgg cctcccaaag tgctgggttt acaggcttga gccaccgcgc     420
cctgtctgac aggttcctcg ttttgtttt tgttttttt tttgagacgg agtttcgctc     480
ttgtcgccca ggctggagtg caatagcagg atctcggctc actgcaacca ctgcctcccg     540
ggttgaagtg attcacctgc ctcagcctcc tgagtagctg ggattacagg cgcccaccac     600
cacgccccgt taatttttg tattttatt agagacagtg tttcaccatg ttggccaggc     660
tggtcttgaa ctcgtgacct caggtgatcc gcccgcctca gcctcccaaa gtgttgggat     720
tacggacgtg agccaccgcg ccgagctgac aggttcctct taaagccctg agtcccaggg     780
aagggacctg caggcccggc cacgcccagg ccgctttagc gcgcaagatg gcggcatgca     840
cgccccgcgg ccggagccga gtgggcccga gcgcttccga gcattcccga agtccagaga     900
aactccggga gcggcgcggg cgggagcggt cggccgggag cggccccgcc cggaacctgg     960
gagcggcggc gccggcgcgg gggaggggag gccggatgtg agtggagcgg ccatttcctg    1020
tttctctgca gttttcctca gctttgggtg gtggccgctg ccgggcatcg gcttccagtc    1080
cgcggagggc gaggcggcgt ggacagcggc cccggcaccc agcgccccgc cgcccgcaag    1140
ccgcgcgccc gtccgccgcg ccccgagccc gccgcttcct atctcagcgc cctgccgccg    1200
ccgccgcggc ccagcgagcg gccctgatgc aggccatcaa gtgtgtggtg gtgggagacg    1260
ggtgagtgcg cggccggggc cgggctggag gccgcgggat cgggcgcgga gggggttgg     1320
gcccggactg gggcccaggc aggccggcgt ccgcgcggtc tcgcgtaggc ggtgggcctg    1380
ggcctgtgtc gcggggcggg ggccgcggcg ggcgccccca ccggaccctg acggcccggg    1440
cggcgcgtgc ctggttccgg ctctcgatgg aggagggcct cgccgctcgc cggctagagg    1500
gaaaagtgaa ctccacccctc cggctttctt cccggacgcc gcccgccgcc ctcctcggga    1560
gcgctcgtag agcaagcgct cttggagatt ttgaccattt ttccaaaaag ggaccctta     1620
tttttttgc atgaacctct cgatcccctt ttgagaattg ggttgggaac gcggcggtca    1680
agtcgatcat atttgatgca tgcttgattg tacgggccgc tttggtgccc ccaaactttt    1740
cttaaaaaa atttttttt catagacggg gtctcgctgt gttgcccagg ccggtctcga    1800
actcctgggt tcaagcaatc ctcccatccc agcctccaaa atgctgggat tacaggcgtg    1860
tgccaccacg cctggctaat cttaaaagt tttttgtaga aatgggggtct cactgtgttg    1920
tccaggctgg tctcgaattc ctgcgctcaa gtgattctcc tgcctctcag cctccaaaag    1980
cgctggggtg acaccgcgcc cggcctctca acttatttc gacaggtttt ttgacttaca    2040
cttctgccac tgttaggatt cttaaaattg ttttcgccct ttccgtggag aaagttttga    2100
agatgctggc tgggaggagc cggctgtaat ggggactgt tttttctttt ctttctttct     2160
tttttttttt taaacaacgt ggtgtggtca ttgacaaaaa aactgttctt tgcttaacgc    2220
gttaggtatg ggatgtagca gaactggccc cctgtgactc caggcattgc ttttcatgat    2280
tgtccgtgat ggttacaggc cctagaggaa gacaaaactt gtcttatgca gtttttttct    2340
```

-continued

```
cccatagaaa caagaatctc agtgtaaccc gagcaaaatc gcgcgtctca gcgttgcttg    2400
tataggttag tgttagcgag gaagaattac taccagttta atcaaactca atgcaactgg    2460
tacatgttgc agtaaagtcc aaggaaagtt ctggcatcac ggttaactgg attgatattc    2520
ttcaaactta tcattaggac agattttggt tcttgcaatt cagatgcaag aaggataatt    2580
agacagctga ttttgtaag atgcccatct gtcggatttg tcttggaagt gtgaaggagt    2640
attagagtat gtaggctatt caggcttttt tttttttttt ttttttttg agacggagtt    2700 tcactctgtt gcccaggctg gagtgcagtg gcacgatttc ggctcactac aacctccgcc    2760
tcccaggttc aagcgatcct cctgcctcag tgtccttagt agctgggatt acaggcacgc    2820
gccaccgtgt ccggctaatt tttgtatttt ttagtagaga cggggtttca ccatgttggc    2880
ctggctggtc tcgaattcct gacctcaggt gatccacccg cctgggtctc ccagagtgtt    2940
gggattacag gcgtaagcca cggcgcccgg cccaattttt ttttttttc tttctttttt    3000 tttttttttg agacggggtc tcactctgtc gcccaggctg gagtgcaatg gcgcgatctc    3060
tgctcctgca acctctgcct cccgggttca agcgattctc gtgccttagt ctcccaagta    3120
gctgggatta caggcgcaag ccaccatgcc cagctaattt gtttttttt tttttttttg    3180 tattttttg gtggagacgg agtttcacca tgttggtgag gctggtctca aactcctgac    3240
cctcaagtga tccgcccgcc tcggcctgtt tttttttttt tttttttta agtcatattg    3300 ctgataatta tttgaaaatt tctaaaacta aacataagc atagcagata cgtttattta    3360
atactaaccg attgtggacc tctgctgttt gaattggctg ttttatctag tcaaataact    3420
tgttgaatgt catggaatct ggaccgtccc ttcaaatccc caccccaccg cttacatggg    3480
gtaaccctaa gcacatcccc cacctcccaa gagaggcggt tcaatgggag gtcaacaaga    3540
ctaaacaaga tgttggttat taactacctc gcaggtgccc cttgctgaat gcttagtaaa    3600
tgccaggtac tgttattgcg gtttctacta ctgagactct gtgagggagt attaggctta    3660
aaagtctgtg gccttgagtt ttcagtctgt ttttttttt taattagtta tgagcatttg    3720
aacaagcaca gttatttttt aatactatgt ttagtattga tgttgactac agctaagtga    3780
tattagaagt gaaatgtacc tggccaggtc aggtggctca cacctgtaac ccagcatttt    3840
gggaggccaa ggtgggtgga tcactagagc ttaggagttc aagaccagcc tgggcaacat    3900
ggcgagaccc tgtctctgct aaaaatacaa aaattagcta ggtgtagaca catgtgcctg    3960
tagtcccagc tactcgggag gctaaggtgg gaggatcgct tgaaacccag gaggtggagg    4020
ttgtagtgag ctgagattgt gccattgcac tccagcccgt gcgacagagt gagaccttgt    4080
ctcaaaaaag caaaaacaaa actattaga gatacgtctt tggccgggca cggtagctca    4140
agcctgtaat cccagcactt tgggaggccg aggtgggcgg ttcacctgag gtcaggagtt    4200
tgagaccagt ctggccaata tggcgaaacc tcgtctctac taaaaataga aaattagct    4260 gggcacgcct gtaatcctag ctattcagga ggttgaggca ggagaatcgc ttgaacttgg    4320
gaggtggagg ttgcagtgag ccaagattgt accattgcac tccagcttgg gtgacagagg    4380
gaaactgtct ttttttgttt gtttgttttt aaaggagata catcttcatc tgttcctgct    4440
ttgacccttt gcctggacca tggcagtgtc ctttcaggct gtacgtccct ccatcctgcc    4500
ctcctgtgcc tctgcttaca ctgggctctt aaggaaactc ctgctccttg tctcatcatc    4560
cctagggatg gttctgtctt atcatttcta gaattggatg ccttgccatc ttgtttgctc    4620
cttaactctg catacagggc tgtgtaaata attccttcat gaaatctct atttcaatct    4680 tctgggatga gtttttttcct tctgggaccc tgactgatag agactgataa tacacccgta    4740
```

```
tgaaaatatg tctgccaggt gcggtggctc atgcctgtaa tctcagcact ttgggaggcc    4800
gaggcaggcg gatcacctga ggtcaggagc tcgagaccag cctggccaac atggcaaaac    4860
cctgtctcta ctaaaagtac aaaaattagc cgggcgtggt ggtgggcgcc tgtaatccca    4920
gctactcagg atgctgaggc aggagaatca cttgaacccg gaaggcggaa gttgcagtga    4980
gctgagattg tgtcactgca ctccagcctg ggcgacaaga gcaaggctct gtcttgaaaa    5040
aaaaagaaaa aaagtcagaa ataatttgca aagcatgtta gaaaattcta gatttcctga    5100
atagcaattt aattgagatt ggccaagaaa tattacatag ggttgatact cttttattct    5160
aagatagtcc tttctgagca tggggtctat aattttttt tcctccacct tactgctgcc    5220
ccacctttta actttcactt agtggacctt tgccccaaga ttttctctca gcttttccta    5280
ggtaagacag catcacccgg gcgcgatggc tcatgcctgt aatcccagaa ctttgggagg    5340
ccaaggcagg cggattgcct gaagtcagga gttcgagacc agtctggcca atatggtgaa    5400
accctgtctc tactaaaaat acaaaaaaat tagccaagga tggtgggggg cgcctgtaat    5460
cctagctact cgggaggctg aggcagggga attgtttgaa tcaagggagg tggaagttgc    5520
agtgagccaa tatcgtgcca ctgcactcca gcctgggtaa cagagtgaga ctccgtctca    5580
aaaaggaaaa aaagacagc atcttacatt caggtattta taaacaactt ttattattta    5640
tttgttttta tttatattg gctcactgca gcctccacct cctgggttca agtgattctc    5700
ctgcgtcagc ctcccaagta gctggaacta cacgtgcctg ctaccatgcc gaggtaattt    5760
tttttttttt tttttttttg agaaggagtt ttcgcccttt ttgcaaaggt tggagtgcag    5820
tggtgcgatc tcggctcact gcaacctcct cctcctgggt tcaagcgatt ctcctgcctc    5880
agcttgtcga gtaggtggga ttacagtcac gctccaccac actgactaat ttcgtatttt    5940
taatagagac gaggtttctc cttgttagcc aggttggtct caaacgcctg acctcaggtt    6000
atccacctgc cttagcctct caaaaagtac tgggattaca ggcatgagcc actacgcctg    6060 gcaattttt gtattttttaa tagagacagg gttccaccat gttgaccagg ttggtttcga    6120
actcctgacc ttaggcgatc tgcccgcctt ggcctcccaa agtgctggga ttatgggcgt    6180
gagccatcgt ccctggccta acaacagtt ttattatttt atttttttatt tttttattgc    6240 ttattactat tttttgagat ggagtctcgc tctgtcaccc aggccggggt gcagtggcat    6300
gatatgggct catggcaacc tctgcctcct gggttcaagc agttctcctg ctttggcctc    6360
ccaaagtgat ggaattacag gcccgagcca ctgcgcccgg ccacaactat tttaatagtg    6420
ttgttttggt gttggttgat taaaggaatg ggaacgaatg acttgaagcc ctctctgttt    6480
cactctttat acaaagtgga gtccagattg ggctagtggc ctgtctagcc caatgtctga    6540
cttggacata cattactgtc caggagtttc ttagctgaat gtgaaaaatg ccttccgtga    6600
catcatcctt acaggaacat tctttacatt tattctttac ttctgttgaa cggtggtggc    6660
gtgaaccatg aatttgttta agcttttcag ctgttttgtg tgttttcctc tcaaggcatg    6720
gggtttcata tttttgacct gtggtaaagg tatttgaatt ctgcactggc ctccaaatgt    6780
aggtgtagta tatggctctg atctttgttg atgattttat acataatgtg gtttttttc    6840 ttgataagcc aaaaaaatta tacataatgt gtgtgtgtgt gtgtgtttta atttcaaatg    6900
atagttacag taaaagtttg gagttgggct aagtgggagg agcatcagga agccatttttt   6960 agaaacctta aattcacccct ttataacttt ctgtcttttt gcattagtca tctgatacct    7020
tagtactgcc tacttttttca catctccatc actacgtagc tcttaaaatt gtagtcttcc    7080
ttgaaaggag atgttttttgt caagagtctt tgccaccaag gcaggattgc atgtgatcag    7140
```

```
taggaatatt ttcctgcaat gtcttaatat gaaaaatttc aaacagacta gtggaaagca    7200
ttgtacagtc aacatgcaca tacccatggc ctggattcta tgacagtatt ttgctctact    7260
tgttcatttt gctgtatttg ctttatcatg tcttcctgtt atcagaggga accttttaag    7320
aggatttata gaggagttga ttttgttttt tgttttgttt tgttttgctc tttttgaggt    7380
ggagtcttgc tctgttgccc aggctggagt gcaatggcat gatctctgct cactgcaatc    7440
tccgcatccc aggttcaggc gattctcctg cctcagcctc ctgagtagct gggcttacag    7500
gcacccacca ccatgcctgg ctaattttg tattcttagt tgagacaggt ttcaccatct     7560
tggccaggct ggtctggaac tcctgacctc aggtgatcca cctgcctcgg cctcccaaag    7620
tgatgggatt acaggcgtca gccaccatgc ccggcctgat tttgaaaaag aatagggact    7680
gtgtgcagtt acatataaat tcttattttt gaactcttgt gtgttcagct ggcttgtatc    7740
aactacacca gggttagcct tgattctgga agggtggatt cagacttcag ctcagttgta    7800
catagtgtct tcagcctaag tgagaaactt tatgcactat cttaattttt tgaagcttct    7860
agtggtaata attgctggct tttttttttt tttttggta gaaacagagt cttgctctgt     7920
cgccaggctg gagtgcagtg gcacgaaatc agctcactgc aacctctgcc tcccaggttc    7980
aagcaattct cctgcctcag cctcctgagt agctgagatt acaggcgtgt gccaccacac    8040
ccagctaatt tcttttgtat tttagtagag acggggtttc actgtgctgc ccaggctggt    8100
cttgaactcc taaggtcaga cagtccgccc accttgccct cctaaagtgc taggattaca    8160
ggcatgagcc accgtgcctg gcttatggct agctttcttt acattgattg tgaagtcaga    8220
tattggtagt agaacatcat aattttagat tgggttttgt gtttatttag cactgcacta    8280
ctctagtggt gtattttct ggacagattt tatctgcata gttaacgcag ttatatataa      8340
ggcctaccgt tacagaatcc ccataccttg tttgtcagtg taaatcgagg accttcatgc    8400
gaggtctttta atttattcaa taagtaggaa tatatatttg acagttacta aattctactg    8460
ccttgtcctt aagatctaca tactttttttt tgtttttga gtcagagagt ctcgctctgt     8520
tgctcaggct ggagtgcagt gatgcgatct cagctcactg caacctctac cccgtggcct    8580
caagcgatac ttctgcctca gcctcctgag tagctgggat tacaggcgcc tgccaccaca    8640
ctcagctaat ttttttgtatt tttaatagag atgcagtttc gctgtgttgg tcagtctggt    8700
ctcgaactcc tggcctgaag tgatccaccc gccttggcct cttgctggga ttacagggaa    8760
gagccactgc gcctggccaa gatctactca ctttttagaca gcaatatatg ctctgtattt    8820
tggtttgcaa ttgtaattgt cattggaaga gtttggctt tctgtcctga gatcaacgtg      8880
tctttaaaag aaggcagtgc agaaagttgt tattttttga gcttcttgga tcttttattt    8940
ttttaacgtg aggaaattcc tagcgtttct agatttgttg attgtgcttt taagttttgg    9000
tttatagatt tcaggaagta acactaaagt ttaccctact ctcctcaaaa agtaagtaaa    9060
aagttctctt ggctgggcgt ggtggctcac gcctgtaacc ccagcacttt gggaggccga    9120
tggggtggat ctcctgaggt caggaattcg agaccagtct ggccaacatg caaaaccct     9180
gtctctactg aaaatacaac aacaaaaaaa aattagctgg atgtggtggt gcttacgtgt    9240
agtcccagct acttgggagg ctgaggcagg agaattgttc gaacccagca ggcagaggtt    9300
gtggtaagcc aggattgcac cattgggctc cagcctggaa gacagagcca agactccgtc    9360
ttaaagttct cttaatggaa aaatgaagaa cataatagca acataagtta tttgctttca    9420
ttgtggttat ttctacagga cagggcaggg gaagcacaga taggttaaaa aaaattgtag    9480
catcatgagc tagggggaaa tccaatgtag aaatggcatg aactttcttc cagccgactc    9540
```

-continued

```
atgttcgttt cctagagtga tgacattgct cgatgattga aaagaggttg aactgagcag    9600
ttaattatat aaagttagaa attccaaaga agtagtaact accagaaatt ctccagcagt    9660
atcagtcaag acttgtggcc aaatacggct tccattcttc atgagggaaa ggccatggaa    9720
aggctgtcac attcccagt gcagatgttg acttggtttg tggaagcgca gcgtggacaa     9780
ggaatgaata tacactaata ggagtggaat aacctttttc ttttacctat ttgaataaat    9840
taagtaaaag ttttaatcag aagacttaaa gaggagtcga tttatctttt tgattgcact    9900
aagcttaaat ataaggttgc actttaagaa ttctgtagtt taataatcat attcttataa    9960
gacatagatt tgtaacaaat agtgattggt aataaaattt cagtcagtat cagattatgc   10020
cagtaccttg aatttcttcc cggttgagcc tttctcagct aaagatgtca ttcaggaaag   10080
gaagtttaga ggattttaga cacagctggt tgcctttata ttagtagttt tgttcctcat   10140
atacatagag acttaggaca gaatagtaaa agaagtgata atgacatttt atcataacag   10200
tcaaaacctt catagcagct tatccttgac actgagtggc aactattgtt aaggttttta   10260
cacaaccttt atcttttttt tttttttttt tttttttga gacggagttt   10320
tgctcttgtt gcccaggctg gagtgcaatg gcgcaatctc ggctcactgc aacttccgcc   10380
tcccgggttc aagcgactct cctgcttcag cctcccgagt agctgggatt acaggcatgc   10440
acgcccggct aattttgtat ttttagtaga gggggtttc tccatgttgg tcaggctctt    10500
ctcgaattcc tgacctcagg tgatccgccc gccttggcct cccaaagtgc tgggattaca   10560
tgtgtgagcc accgagccca gccaacccttt atcattttta aaaggtccc ttagagcctt    10620
aggctccact ttcttcctca gctgccacat ccaaaccatg ggtaagcgat gcttgatctg   10680
cctccaagtt caagcagtcc aggaaacagc ccactatgt tcactgtcca gtccccattc    10740
ttggtccagg ccaccatgga tggctcctgg actgtagcaa cagcttccat gtgtgtctgc   10800
cttgactgag tccctggcgt cctcaggctt cctgccacac tgcagttgga ggcttcttct   10860
aaaatccagt gctttctggg caatttaaaa cctgtgactt tccaagtagg atctagtccc   10920
catgtcctta acaagaagag gtaacgtatt tccctatgcc actgcccact tattttttta   10980
ttgttgagat gggatcgtgc tttgtcacct aggctgggtg gagtggtgtg atcacagctc   11040
actgctgccc tgaattcctg ggctgaaggg atcctcttgc ttcagcctcc tgagtagctg   11100
ggactacagg caagagccac cacttatttt tgaatttttt gtggaaacaa ggtctcccta   11160
tgttgcccag gctggtcttg aactcctggg ctcagcgatc ctcccacctc aggcccctgt   11220
gctgggatta tagcctcctg tgctgggatt acaggcctaa gccactgcac caggctttta   11280
tttttttaatt taaaaaaatt tatttttttg agacagggtc tcactttgtc cctcagactg   11340
gatgcactgg tgcaatcttg tttcactgca gccttgacct ccctcctggg ttcaagtgat   11400
cctcgtgcct cagcccccca agtagctgag actactgctg cacaccgcca cacccaccta   11460
atttttgtat ttttagtaga gaacgggttt ctccatgttg gccagctgg tcttgaactc     11520
ctgggctcaa gcgatccacc cacctcagcc tcccaaagtg ctaggattac aggcatgagc   11580
caccatgcct ggcctaaaaa tattttttttc agctctagaa atgttagctc ttttgctgta   11640
catttccaga gctgctttaa taatgacagt tatcacacgc ataatttcat gtgatgattg   11700
cattcttaat ttttaaattt aacaactgca cttacttcat gaggtcttgt tcattgatac   11760
atctttagca cctagtgtgc ttctggtgta gcacacggtt gatataaatt gaaattgaat   11820
taatgctcac agtagtttgg ggatggagct ggtagttctg cattaatttt gcaggtgaaa   11880
aaaaaggca tgaggaagtt gaaacttgcc aaaaaaataca gccagtacgt gctagaattg   11940
```

```
gccctgggtc tcaaatctgg gcttctgact ccaaagctta ggctcctgct catacaggtt   12000
tattttcaca ttctaagctt ttaacgaaat gtatgtccaa tgagtcattt ctgtttagaa   12060
agcctttagg agttggaagc tacttcctgg tgatgtaatg tttgactctc taaagtcttt   12120
ggaatgggga gttccaactt tgttaagcc ctcaataatg tcatgagtga atgaatattg    12180
gcaagactgg ctgggcctgt aatctgcctt gagtgtgagg gaaaatggaa aagcgcttaa   12240
ctttatggtg aattctaatt tatagtagtt gagattgaac gacaaaaatc ttaaaattat   12300
gatgctgatg tgtcattgtg accttggtaa actgacagca cagcagagag aagggctcat   12360
taaggagagc acttggctaa ctgaaccctc aggatgccag agacttgaat tctcatgtaa   12420
gcccttaagc ttgccttgtc aatgctgtaa aaattggaga cctttatgtt ttgctaatga   12480
tgtggtgacc ttagttatta ggtgatagcc tcttgaaaaa cattccaggt ggtttgggaga  12540 ctttcagcca ccactcttct gcctggcggc acactggtaa tattaggatt agtctctacc   12600
cattgccagt tgtgcaggtg gtgctccttt ctctgaagta tttctacaca cttctctgtt   12660
tggcaagttt aactcccatc gtctctgagc tgttaattaa atgtctggga tgtattgtga   12720
tagtccctgc ttatagactt atggtgctgt gtgaggattg gggctggggg aggtggcatt   12780
taaatacagc tgaatcaatg tgatggcagt tacgtgtggt agtttattga ctaagcactt   12840
tctctcaaga gaacagtcat tgctgattgc catagggggag ctgtaggga tgtggtggga   12900 ttttgagctg tcccacttaa ggcagcagaa taagttactt aaagaggaag gctgtgtttg   12960
tatattagtg ttaattaaaa tacctttagg ctgggtgtgg tggctccagc ctgtaatccc   13020
agcactttgg gaggtccagg tgggcggatc acttgaggtc aggagttcga gaccagcctg   13080
gccaacatgc gaaaaccca tctctactaa aaatacaaaa aaattatcca ggcgtggtgg    13140
tggacagctg taatcccagc tacttgggag gctgaggcag gagaatcgct tgaacctggg   13200
aggcagaggt tgcagtgagc caagatggtg cctctgcact gcactccagc tggggcgaca   13260
gcacgagact cggtctcaaa aaaaaaaaa aagaaaaaa aagaaaaaaa gaaaatatct     13320
tcaggatcaa acttaagatt cttgatgaga ggctctacag atgttcacag aagagacgtg   13380 aagtttaaa atcttgtttc tcttgagtct tgtagctagg tgacaactgt ttcttgacta    13440
ttaatgctaa caccgggtac ctaaacagaa tgtgatggct cctgactcta tctttctgag   13500
aaattctagt ttgtttactt taaatttcag ggtaccaatg tgtatgtggt gataaagggt   13560
tatagaaaac atttttcttta atgctaagta tgtgatgtat atgccttgat ttttttctc    13620 tagaaattat tttaacttaa tagtgaaagc taagattaca ttcatgttga ctaagcaacc   13680 tttttctct ttctcttag agctgtaggt aaaacttgcc tactgatcag ttacacaacc     13740
aatgcatttc ctggagaata tatccctact gtgtaagtat cttaaattgg gaattaacct   13800
gtttgtgtta cgggtttcac atttctttga ccatttgttt tgctgtaaag ccatctttaa   13860
tcctcatatg aacagatact aattttttct taaacattca ctgaaaccta attataaggt   13920
atattaggct tttaaaaaat agggctgggg gtggtgatct cagcactttg ggagactgag   13980
gcgggtggat caactgaggg tcaggagttc gagaccagca tggtcaacgt gatgaaaccc   14040
catctctact aaaaatacaa aaaattagcc aggtgtggtg gcgggtgcct gtaatcccac   14100
atacttggga ggctgaggca ggagaatcac tcgaaccgtg gaggcggagg ttgcagtgag   14160
ccaagatcac gccactgcac tccagcctgg gcaatgagag cgaaactcca tctcaaaaga   14220 aaaaaaaaa agaaacttag ggtaatataa acttttcaca actttgctag ttgattttta   14280
gacatccaga aagcaaactt taactgtctg tgaggtcacag agactggatg atgttaaaga  14340
```

```
aaaccatagt tggacacaag aactctgacc aaaagtctga tcagaaacag tccttgtcag   14400
tgcacgagtt tcagatacac tggctttctg ggaactggaa agggaaagat tccattacgt   14460
tttaattggc cttttctgat aagtcatcag ttggttacat gtccgcattg aggtgtaggg   14520
ctttggaatt gaaacttggg tgtgtgtgtt gaaggggaa tgggagggtg gaattggcta    14580
ttgaattgct tactccctat aggcagcaga attgggtgga gacaggaaag tgctgctctg   14640
gtgatgggtt acccgggagc gcacgtagct gagcctcata atgcaccatc ctgcagctgc   14700
tgtgagtcct ccctgtgcag gctggggagg tgtcgcctcc tccccacctg tgttcacctc   14760
ctcaggcaca acacacaccc aggtgctctc tgaagtgtcg tacccatgtt tttgttgttg   14820
ttgttgttgt tttccttttt tttttttttt tttggagtta gtctctctct cttgcccagg   14880
atggagtgct gtgatgcgat ctcagctcac tgcagcgtct gcctcctggg ttcaagtgat   14940
tctctgcctc agcctcccag gtagctgtga ttacaggcat acaccaccac acctggctaa   15000
ttttttgttc tttagtagag acgggtttca ccatgttggc caggttggtc tcaaactcct   15060
gacctcaggt gatctgccca cttcagcctc ccaaagtgct gggattacag gcgtgagcca   15120
cggcacccat ttttactgt aagtggaatc atgctgtccc tgttgtccta aatttatggg    15180
ggagattttc cttatctaca tatgtagata aaggtttaat cattaatgat taatgatttt   15240
gaagtactat aactgattta acccactggt cacttggact cttggtgtta acaaacattg   15300
ctgggttcag tgttgtccct tatgtctttg tgtacacttg atagattatt agaagcaaaa   15360
tcgtgccaaa tcaaaagaca atggatgttt taaattttgg tagatacagc tgggcgtgat   15420
tgctcacgcc tgtaatccca gcactttggg aggccaagac ggaaggatca cttgaggtca   15480
ggagttcgag accaacctgg ccaacatgtt aaaaccccca cctctgctaa aaatacagta   15540
gttagccggg tgtggtggtg cactcctgta gtcccagcta ctcaggaggc tgaggcatga   15600
gaattgcttg aacccgggaa gcagaggttg cagtgagcca agattgtgcc actgcacttc   15660
agcctgggta acagagtgag actctgtctc ccaaaaaaaa aaaaaaatta aaaaattatt   15720
ttttggtaga taactaccaa attgctgtct ataaagctgt cactttgctg gccttgactt   15780
aagtggcctc ttagtacaca ctgccattaa cgtgggttga agttatctaa ccgttttcat   15840
ttccaatcac agatgtggtt aaaatctttt gaattttttt tttttttaat taaaaaagtt   15900
tgctcacgcc tgtaatccca gcacttgggg aggctgagct gggcggatca ctgaggtaag   15960
gagtttgaga ccaacttggc caagatggtg aaaccctgtc tctactaaaa atacaaaaat   16020
tagctgggca tggtggcaca tgactataat cccagctatt cgggaggctg aggcaggagg   16080
attgcttgaa cctgggaggt ggaggttgca gtgagccaag attgtgcctc tgcactccag   16140
cctgggcaac agaacaagac attgtctcca aaaagaaaa aaaaaatatg tgttttgta    16200
gagctatgtt ttgctatatt gcccaggctg tcttgaaga cctggcctca ggtgattctc    16260
caccttggtc tcccgaagtg ttgggattac aggcgtgagc caccacacct ggctcttttg   16320
aatgtttact gtacattttt agtctcttgt gaattgtctg tttaaatctt ttgtattttt   16380
ctactgaaat ttttttcttac tgatggaaca tttccttcct tccttccctc cctccctctc   16440
tccctccctt cctccctcc tttcttccct ccctcctcct ctcctccct ctctccctcc     16500
ttccctcctc tcctactcct tccctccttc cctccttcct tctcctttct tttccctcc    16560
ctcccttgct ccctccctcc ctcccttttt ttttttttt tttttgaga tggggtcttg    16620
cagtattgcc caggccggac ttgaagtact ggtccttcca cctcagccta ttgagtagca   16680
tgctccactg cacgtagcct gatggaacgt tttgtaaata atcctcagtc tgtcatttgt   16740
```

```
ctttgtactt cattatggtg tcttctgcca tatagaaatt tagcatttaa tgtaaataat    16800
accaccttac ccgggcacgg tggctcacac ctgtaattcc agcactttgg gaagctgagg    16860
tgggcgcatt atgaggtcag gagatcaaga ccagcctgat caacatggtg aaaccccatc    16920
tctactaaaa atacaaaaat taaccgggca tggtggcgtg cacctgtaat cccagctcct    16980
caggaggctg aggcaggaga atcacttgaa cccaggaggt ggaggttgca gtgagccgag    17040
atcgcaccac tgcactccag cctgggtgac agtgagattc tgtctcaaaa aaaaaataat    17100
aataataatg ataataccac ctctccctca gaattgtatg ttgtacttag aaaggccttt    17160
cctacttaaa taatgcaaaa gtatgctcta gtattttttt ctaggatttt tgtggctaaa    17220
atttttatct ttaattcatt taggacttat ttttggtata gaatgaggca aggacctgat    17280
tcttttttccc ttatggggaa aaaagtcac aatactattt atccaataat tttttcttta    17340
tggaaatata attaacatgt ccatcaccat cacacctttt ctttcttctt cttctttttt    17400
cttgagaccg agtttcgcac ttgttgccca ggccggagtg cagtggcgca acttggccca    17460
ctgcaacctc tgcttcccgg gttcaagcga ttctcttgcc tcagcctccc aagtagctgg    17520
gactacaggt gcctgtcacc acgccctggc taattttttgc attttttagta gacacaaagt    17580
ttcgtcatgt tggccaggct ggtctcgaac tcttgacctc aggtgatccg cccacctcgg    17640
cctcccaaag tgctgggatt acaggcgtga gccaccgtgc ccagcctctg ctttttatta    17700
tattttttcct tttttttttt ttcttttttg ccttcctgtg cagaggaaac actattttct    17760
tctaaagctt ggtttctgct gaccagtagc aattttttaac atcagtctga tttccctctg    17820
tcagcctata ggctttgctg ggttatctct cctgactaat ttgtgtagca acttcacatg    17880
aatttaaaca tttgtatcat cagtttaacac tcactttgaa aatgttattg ggaggcttgt    17940
taagtcaggt gtattttgtg tgactgctct acactcaggc cttctggaaa ccctgcagag    18000
ggtagctcta gtggccagct agctctcttg ctgaaaatga gcaacataag tacatgaaaa    18060
acccaacaag taggatttga aagcggggct aattgtaccc ttatttcttc tggggataaa    18120
agtcttaaac tttgtttaaa gtaaaatgtt tttattttctg acggtgattt gtttcactta    18180
aatagcttgt tgtttgtttc tttcatttct cttaagtttt gggttgggtt tggtttgttt    18240
cccgcaagtt ttgcccgtgc cgccttcctc cttgtgcctg cagggacatt tgctggtgtg    18300
gcagcctcca ggcccgtccc cagccttttt cttggcacac cttctctagg atggctggga    18360
cagtgactta gcttctacac ctgtgactaa ccattttcat tccattctac agctttgaca    18420
attattctgc caatgttatg gtagatggaa aaccggtgaa tctgggctta tgggatacag    18480
ctggacaaga agattatgac agattacgcc ccctatccta tccgcaaaca gtaaggattg    18540
cagctgactt ttaatgtgtc ttttagagta tataattctc gagcgcttaa ttagtgcatg    18600
ttacctatgg acttgcttat attgccatca tttgggtatt gagtaaatag caaacagggt    18660
gggattggtt ccatgtaaac atcccccctag atgcaagccc aggggttttg tgttttgagc    18720
gttaccagct gttccattgt tgggcatttt acagtcttcc atttagcttt agaataaccg    18780
tatgaaagag ctactttttg ttttttgcaaa ccagttttta acaccaatta gtttgaaggc    18840
aggtttgctg tgtgacattt ttgtaccaca gaatcaaatt aggcagttaa gattcaggtt    18900
tctttaaacc aagttagtaa ctaatctcac aggtttaata catttttttcc cacaaaatac    18960
ataaatttgta tggattttgt gaaccataca atagaaccta aatttattca atgtagattg    19020
aagttttggt tttgtaaaat gtatccactg tgtctaatca gaaaaaaaag tttacttttg    19080
cttctgtatc agacaactaa gtgatttatt taccaaagct aattagagca gtagctggtg    19140
```

-continued

```
aaaatgggta cttagaagac attgttgtcg ttaaaagtta cttttcttta agcagcggtt      19200
ttacttgtgt atcatttgct tatcttgtta catgtttgtt cttcatttttt aaaagtatct    19260 ttggaagcaa aagttaaata tgcttgagat tccttgggtt gataacctgt gtgcatgtcc     19320
tagctctgtg acttcaggca ggcttcatcc tctctccagt ctttgcctgt ttccttgtag     19380
ggtgagatga gtacgtgtca cgcacgcata acagtcctgg gcacatagca cacactgtgg    19440
ggccagccgc tgtcagaatt ctcctgttcc tcagtgtgcg ggtgggtcgg cctaaagagt    19500
gctgctttcc acgttgtgcc caaatgagtg gaagttgtgt ggtgctcagc acacctgggt     19560
tggccggagg gattggggtt ggggttgggt tgaggtcagg aagacatcct agagaaaggc    19620
tggctttgag ccctgattga tgatgaggca gcctgtgatt gattcaacca gtacttcgtt    19680 gtaggggta atatggtga aataacttag tggttaagtc tgctgtatta aaatcagtc       19740 tataatcccc agacaattca aattcttcag tatcttagga aactcttcta tacccagtgg   19800
atgtttaata attcagattg taaatggatt taaaaacata ctggctggta gagtaggaga    19860
cttcagccca ctggacacat gtggaagggt gtggtgtcat tctgagaaac aagagccacc   19920
ctgctgtgac tcaggggta ccgggcaggg tgaggcctct ctaaggaagg cctcacagta   19980
agtcaagggt gacttggcag gagtcccact ttgtgttctg aggaacacac agataaggaa   20040
agagaactct cctcagcttg aacaaagctg tagagtgtga cgcctggtat caaagtaggt   20100
gttgtcctca tagggctaga acttaaactt catgtttcct ctgtgtgaga ctgtggactg   20160 cttttcctata aaatatttga ggagcaaggg agggagtggg acatggttct tgccctcagg 20220
tagttcacag aaaagtccca taaactgtgt aagacaccct gtgctagcaa gggggtgagc   20280
cgggcgctta aggagcaaga ggggcgagca cccacccagc agtggaagca ttcctgtctg   20340
gactccttca gagataagga aattatcttg acaactcagg ggcaggccac agatgctcag   20400
ataccagtgt ctggaaggtc tcatcccttt gagccacact gtcctaagaa gaactggatc   20460
tggtagtaac atgctggcac ctgggtctct tgttgataaa ggggaaacct ctaaattttg   20520
tactacatgg aatgtggtcc ctgattgctg gctctgtggt ctgcagacct gttgatgtag   20580
ctcatccaag actgcttaga cactctcctg aaggaccagt tggaagattt cttatctagg   20640
gtgtcctaaa aagagatgtt acatttcttg tggtcattta acattggcat cctctctatt    20700
gggcagctct gtcggctaag tctgttcaga ccattcattt cttcttcgtt ctccaaagat   20760
ggtgagcagg tagtcgccat tcttagttga aattgcccctt caggttttta tttcccgaat 20820
tacgtaatcc ttacattatt ttctcttgaa aatctttgct aagttctgca tactcatctt   20880
cagttgctat gcacagaatc aagtcttgtc agagtaacgc tcaagtccag catcttccct   20940
tgtgtagatc acctgtatt tattgcctgc ttgtaccagc attggtggtg tgagtgggag   21000
cctaagtgac ctgtcagtgt cacagcgagt cctgagccct gtgtgtgtcc tgagactcag   21060
gctgtgcagc gggttcgctg agatgctgag cctccatgtt ggggtcagcc aggacccag    21120 tgcgtcatgc cagttgtttc attttctctc taggctaaaa gttgttgttg ttgttgttgt   21180
tgtttgagac agagtttcgc tcttgttgcc aggctggagt gcaatgggtg tgatcttggc   21240
tcactgcaac ctccgcttcc caggttcaag tgactttccc gccctagtct ctcaagtagc   21300
tgggactaca ggcatgtgct accatgcctg gctaattttg ttttgtattt tatttttttt  21360
gagacagagc gagactctgt ctcaaaaaaa aaaagaaaa caagaaaaa agaaaagctt    21420 gagtgagatg aaattaaaat aattttctca ttttgagaca gggtctcgct ctgtcaccca  21480
gactggagtg cagtgtcaca atctcgcctc actgcaacct ccacctcccg ggttcaagca  21540
```

```
gttctctgcc tcagcctccc gagtagctgg gattacaggt gcctgccacc atgcccggct   21600
aattttttgt attttttagta gacacagggt ttcaccatct tggccaggtt ggccttgaac   21660
tcctgacctc gtgatccacc tgcctcggcc tcccaaggtg ttgggattag aggcgtgagc   21720
gcttttctta aaagagttcc agggttctat gttggaagag cgagtttgtc agttttatt   21780 ggaacaaaga aatgaattga cagcattgtg ataaacactg gaagtgtcac ttctaaaatt   21840
tgtccatggc tgaaagtggt ggctcatgcc tgtaatccca gcacgttggg aagccaaggt   21900
gggtggagca cctgaggtca agagtttgag accagcctgg ccaacatggt gaaacctggt   21960
ctctactaaa aatacaaaaa attagctggg cgtggtggtg tgtgcctgta gtcccagcta   22020
cttgggaggc taaggcagga gaatcgcttg aacccaggag gcagaggttg cagtgagctg   22080
agatctcacc attgcactcc agcctgggca acagagcaag actccgtctc aaaaacgctt   22140
gtccttaagg ggtggcttcc cccagaccta caaagtagcc cagaattgga ggtcttagtg   22200
tcagcaacag tgctgatttt gataatgcaa gtctgtacat tcaaaccagt ctcccagaac   22260
taggtggaag ataggaacat ttctgcatag gagacttgga atgttctggc agcattaaaa   22320
ccctgaggcc cggctatgtt ctgggagagc cctttggcag gcatcattta cagacgggtc   22380
cttttcctgt atgctgtggc ttcaactagg ctgtgtctga gaactcggat ggagcacttg   22440
aaagtgcccg tggctcccgc ctgcctttgc ggtaagggac agtgcagaac atctccggct   22500
gtgccagctg ttgtagattc tggtgggtgc tgccatggga ggaggagcac gttgttgccc   22560
cccctcagga tctccctgac ctctgtcttc accatcgttg aacttaacgc ctgcttttga   22620
ccaggtagcg tggagtgttt cagtggcatt tgtcatcgaa gatatgttag aatctattgt   22680
atgcttttgg atctctccgg agggttaaga caaaattcta ataaagaatc gataagaggt   22740
tatattgatt tttgttgtcc tcagtctgta ctaaactcaa accaagttct catgcattac   22800
taggttggag aaacgtacgg taaggatata acctcccggg gcaaagacaa gccgattgcc   22860
gtatgtaaaa ctttcagtcc acttcagttt caagctttct ctgttctctc atttcacttc   22920
gttttcctag gatttttat taagcctcaa gctccttgag tgtttatat ttaattcact   22980 caaggttggg gttttgcttg atgaaataaa cttcattaga gtgtgatagt ttacccaccg   23040
gcttgaatta aagcagtttg tgaactgtga tcttctcctc ccaagtgaaa ggagggggaca   23100 gtgagagggc ccctctcctg gctggttgga gatgcagata tggagactcc tcccggaagc   23160
ccacctggct gtgagccgag ccggagcagg accaaccttg ttgccggggc cttctttctc   23220
cgcttgggtg tcccgtgtgg tggggctgtc tgggcgtggc tgtgcagtgc tgctgagcta   23280
accccaccgt gcttgagatg gtgtgctggg tgccgcggtg attcttggac gagcttgtgc   23340
atgcgccagc actcttcaaa tgccagttat aaaaagctgt tgtgtgggat gtttctttcc   23400
ctttcaggta caaggtatca gctggagggt tgaaagtgta gcttgggaat tgtgtgcatt   23460
tcataaagta gcataattgc cttttttccag gagaatattt tagaaatcta gcatttttaga   23520 attcttgggc atttttaaat acaggtgaat atttgaattt ggtttgacac aaaatacaga   23580
atggatgaag catgcagatg tttggcgtgt gccccgaagc accctctact ctgtcctctg   23640
cacccaccct ttgcgcctct gcgtcagcca cagctgcccc gggagcgagt tctcctgagg   23700
ccctggctgt gctgactcta gggcagcgtg agggtggttg tcagctgtga aggtgccact   23760
tacacactaa gtcctccttc cttgtggagg aagggctca agtagcaaat attggagccc   23820
ccgcttggtg ctgggagctg tgacaggcag ctcctgaaga agcagtttaa ttggaaccag   23880
tgaccatcta aaactgtttg tactctaaac cagatttac agaaatattg gaatcatacc   23940
```

```
tttatacttg attttttctt tttagatagt taggcgtaaa ggaagcctcc tgagggtctg    24000
gtctgatcct cctgatcctt gaagagcttc cagcatcatt ctcccttcat gctccccatt    24060
ttcataagta actggtggct tgacatgctg ggtttggttt gggagccctc tgacaaactg    24120
aaagggtgga tcaggaagcg tctgaccaca ccactggtag acacgctctg cgtccaacaa    24180
gtccttccca gcaacatgta gaaagcaaag tgcatgcttc attctaaggt tgttgtctaa    24240
atgtttccct gtgtttcctt tttgtaggat gtgttcttaa tttgcttttc ccttgtgagt    24300
cctgcatcat ttgaaaatgt ccgtgcaaag gtaggtgggg atttaaaatg tgtatgtaag    24360
ttatagaatg atcctctcag aaataaatac tttaaaatat cacttagcct aggaatttt     24420 agttatttaa attggtttta gcaatttgct acttaggtac atgattgggt ttttttttt     24480 cttttgagac ggaggtctca ctctgttgtg tccaggctgg agttgtactg gtgacatcag    24540
agctcactgt agccttgaac tcctgggctc aaacagttct cctgcccag cctcctgagt     24600 tgctgggacc ataaatgtgc accaccatgc gtggctaatc ttaaaagaat ttttgtatgg    24660
ctggttttgt agaccctggc ttgtctcaaa ctcctgggtt gaagtgatct ttcagcttca    24720
gcctcccaaa gtggtgggat tatagctgtg agccactgca tctggcccat cagcagttta    24780
ttttatttat ttattttga gagagtcttt ttttttgctt ttgttttttgt tttgagatg    24840 gagtttcact cttgttgccc aggctggagt gcagtgacgc aatcttggct cactgcaact    24900
tccgcctcct gggttcaagt gattctcatg cctcagcctc ccgagtagct gggattacag    24960
gcatgcacca ccacgcccgg ctaatttttgt atttttagta gaaatgtggt ttctccacgt    25020
cagtcaggct ggtctcgaac tcccgacctc aggtgatccg cgcgtctcgg cctcccaaag    25080
tgctgggatt acaggcgtgg gccaccgtgc ccggctgaga cagaatcttg cgctgtcatc    25140
caagctggag tgcagtggca caatcttggg tcactgcaac ctcccccctcc cggttcaagc    25200 aattctcctg cctcagcctt cttagtagct gggattacag gtgcccgaca acacacctgg    25260
ctaatttttg tacttttagt agagacgggg tttcaccatg tttgccaggc tggtctcgaa    25320
cccctggcct caagtgatcc acccgccgca gactcccaga gtgctgggat tcaggtgtg     25380 agccactatg cccggcctaa tacgtggatt tttaaagctt caggttctgg ttcagaagtt    25440
tcctgggtct cattaaaata atgaggcact cagaattggt ctaataaaaa taacgaccat    25500
ttctttctac tccagtctct ttcacaaact tcttagtgaa aatgacaagt gaggcccttc    25560
agtaggggca ttttcagtgg agataatagc ggcagacctg agaccttggg ctaggtagtt    25620
tattctcatt tctgaacaga tgatgaattt tctcagatga ccctaagaaa ttgttttacc    25680
aaaaacaaag tgatctattt gctttgggag gaactcccct cctttttgtttt ctcttccctt   25740 ccccccctcc cctgcggttg tagagcccgt tctgtccggt cgtggttctg tccagccatg    25800
atccgggagt cctagcttgc taatggaaca cctgagatgt tccttatggc tcaaggcttg    25860
aattgaaggt gggaaccacc tgaagcctcc gtggggaggc cttgcctgag gttaggtgtc    25920
tggcatgagt gccgccggct gggtgtgatt taggtgaagg acatctgtaa aggagcgtgt    25980
cacaacctct gttccttctt cacatctagt ggtatcctga ggtgcggcac cactgtccca    26040
acactcccat catcctagtg ggaactaaac ttgatcttag ggatgataaa gacacgatcg    26100
agaaactgaa ggagaagaag ctgactccca tcacctatcc gcagggtcta gccatggcta    26160
aggagattgg tatggaatcc tgtgtttttc ctcctccttg tacctctttt attgtagtga    26220
cagagactgg agtccagtct gggaaaggag ggtgtgtgtc tcccactcag ggcctggtgt    26280
actcttgggg aaccagctgg caaggccctg tgggtcttaa cgtcagcgtt ggaaggtgga    26340
```

```
agcagggctg ggagccggca gaaggcgccc gggccccagg agctgcctcc cgctggtggt  26400
gtgatcagaa gagagtgggg tcgagtgtac attgccgtgt ggtcgtgttt cctgtaggtg  26460
ctgtaaaata cctggagtgc tcggcgctca cacagcgagg cctcaagaca gtgtttgacg  26520
aagcgatccg agcagtcctc tgcccgcctc ccgtgaagaa gaggaagaga aaatgcctgc  26580
tgttgtaaat gtctcagccc ctcgttcttg gtcctgtccc ttggaacctt tgtacgcttt  26640
gctcaaaaaa aaacaaaaaa aaaaaacaaa aaaaaaaaac aacggtggag ccttcgcact  26700
caatgccaac ttttttgttac agattaattt ttccataaaa ccattttttg aaccaatcag  26760
taattttaag gttttgtttg ttctaaatgt aagagttcag actcacattc tattaaaatt  26820
tagccctaaa atgacaagcc ttcttaaagc cttatttttc aaaagcgccc ccccattct  26880
tgttcagatt aagagttgcc aaaatacctt ctgaactaca ctgcattgtt gtgccgagaa  26940
caccgagcac tgaactttgc aaagaccttc gtctttgaga agacggtagc ttctgcagtt  27000
aggaggtgca gacacttgct ctcctatgta gttctcagat gcgtaaagca gaacagcctc  27060
ccgaatgaag cgttgccatt gaactcacca gtgagttagc agcacgtgtt cccgacataa  27120
cattgtactg taatggagtg agcgtagcag ctcagctctt tggatcagtc tttgtgattt  27180
catagcgagt tttctgacca gcttttgcgg agattttgaa cagaactgct atttcctcta  27240
atgaagaatt ctgtttagct gtgggtgtgc cgggtgggt gtgtgtgatc aaaggacaaa  27300
gacagtattt tgacaaaata cgaagtggag atttacacta cattgtacaa ggaatgaaag  27360
tgtcacgggt aaaaactcta aaaggttaat ttctgtcaaa tgcagtagat gatgaaagaa  27420
aggttggtat tatcaggaaa tgttttctta agcttttcct ttctcttaca cctgccatgc  27480
ctccccaaat tgggcattta attcatcttt aaactggttg ttctgttagt cgctaactta  27540
gtaagtgctt tcttataga accccttctg actgagcaat atgcctcctt gtattataaa  27600
atctttctga taatgcatta gaaggttttt ttgtcgatta gtaaaagtgc tttccatgtt  27660
actttattca gagctaataa gtgctttcct tagttttcta gtaactaggt gtaaaaatca  27720
tgtgttgcag ctttatagtt tttaaaatat tttagataat tcttaaacta tgaaccttct  27780
taacatcact gtcttgccag attaccgaca ctgtcacttg accaatactg accctcttta  27840
cctcgcccac gcggacacac gcctcctgta gtcgctttgc ctattgatgt tcctttgggt  27900
ctgtgaggtt ctgtaaactg tgctagtgct gacgatgttc tgtacaactt aactcactgg  27960
cgagaataca gcgtgggacc cttcagccac tacaacagaa tttttttaaat tgacagttgc  28020
agaattgtgg agtgttttta cattgatctt ttgctaatgc aattagcatt atgttttgca  28080
tgtatgactt aataaatcct tgaatcatac gactggtaat actggtgttt tgagacttg  28140
atgaacaagt tcctggtgtg tgtttgtttg ccttgcttta aagtcctggg ttgttggaga  28200
cagtcatttt caatgcgtgt ctccacacag gagggacagg gagtgccacc tccaggggag  28260
aactgggtga gcccaaatac ggcaggagtg gaggtgacat tcatgtttgg acctgtcgaa  28320
cagtggcgaa gctctgaggg agaagcgcct atcgggtgt gtgtgcacat cctggcccag  28380
agctaggggc tgaagatgga gatgttggga ccctagactg gccctggaag agtagaggtt  28440
ggtgaaccac atgcccttaa gatccttttcc agaggctgag tgcgtggctt acgcctctaa  28500
gcccgacgct tgggaggct gacacaggag gagcgcttaa gcccaggagt tctagaccag  28560
cctggac                                                          28567
```

<210> SEQ ID NO 24
<211> LENGTH: 211
<212> TYPE: PRT
<213> ORGANISM: Homo sapiens

<400> SEQUENCE: 24

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Val Gly Glu Thr Tyr
65                  70                  75                  80

Gly Lys Asp Ile Thr Ser Arg Gly Lys Asp Lys Pro Ile Ala Asp Val
                85                  90                  95

Phe Leu Ile Cys Phe Ser Leu Val Ser Pro Ala Ser Phe Glu Asn Val
                100                 105                 110

Arg Ala Lys Trp Tyr Pro Glu Val Arg His His Cys Pro Asn Thr Pro
                115                 120                 125

Ile Ile Leu Val Gly Thr Lys Leu Asp Leu Arg Asp Asp Lys Asp Thr
                130                 135                 140

Ile Glu Lys Leu Lys Glu Lys Lys Leu Thr Pro Ile Thr Tyr Pro Gln
145                 150                 155                 160

Gly Leu Ala Met Ala Lys Glu Ile Gly Ala Val Lys Tyr Leu Glu Cys
                165                 170                 175

Ser Ala Leu Thr Gln Arg Gly Leu Lys Thr Val Phe Asp Glu Ala Ile
                180                 185                 190

Arg Ala Val Leu Cys Pro Pro Val Lys Arg Lys Arg Lys Cys
                195                 200                 205

Leu Leu Leu
    210
```

<210> SEQ ID NO 25
<211> LENGTH: 192
<212> TYPE: PRT
<213> ORGANISM: Homo sapiens

<400> SEQUENCE: 25

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110
```

```
Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
                180                 185                 190
```

<210> SEQ ID NO 26
<211> LENGTH: 579
<212> TYPE: DNA
<213> ORGANISM: Homo sapiens

<400> SEQUENCE: 26

```
atgcaggcca tcaagtgtgt ggtggtggga gatggggccg tgggcaagac ctgccttctc    60
atcagctaca ccaccaacgc ctttcccgga gagtacatcc ccaccgtgtt tgacaactat   120
tcagccaatg tgatggtgga cagcaagcca gtgaacctgg ggctgtggga cactgctggg   180
caggaggact acgaccgtct ccggccgctc tcctatccac agacggacgt cttcctcatc   240
tgcttctccc tcgtcagccc agcctcttat gagaacgtcc gcgccaagtg gttcccagaa   300
gtgcggcacc actgccccag cacacccatc atcctggtgg gcaccaagct ggacctgcgg   360
gacgacaagg acaccatcga gaaactgaag gagaagaagc tggctcccat cacctacccg   420
cagggcctgg cactggccaa ggagattgac tcggtgaaat acctggagtg ctcagccctc   480
acccagagag gcctgaaaac cgtgttcgac gaggccatcc gggccgtgct gtgccctcag   540
cccacgcggc agcagaagcg cgcctgcagc ctcctctag                          579
```

<210> SEQ ID NO 27
<211> LENGTH: 192
<212> TYPE: PRT
<213> ORGANISM: Homo sapiens

<400> SEQUENCE: 27

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
            35                  40                  45

Lys Pro Val Asn Leu Gly Leu Trp Asp Thr Ala Gly Gln Glu Asp Tyr
50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
            115                 120                 125

Leu Lys Glu Lys Lys Leu Ala Pro Ile Thr Tyr Pro Gln Gly Leu Ala
130                 135                 140
```

```
-continued

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Ala Cys Ser Leu Leu
            180                 185                 190
```